US 6,743,581 B1

(12) United States Patent
Vo-Dinh

(10) Patent No.: US 6,743,581 B1
(45) Date of Patent: Jun. 1, 2004

(54) MULTIFUNCTIONAL AND MULTISPECTRAL BIOSENSOR DEVICES AND METHODS OF USE

(75) Inventor: Tuan Vo-Dinh, Knoxville, TN (US)

(73) Assignee: UT-Battelle, LC, Oak Ridge, TN (US)

( * ) Notice: Subject to any disclaimer, the term of this patent is extended or adjusted under 35 U.S.C. 154(b) by 0 days.

(21) Appl. No.: 09/890,047

(22) PCT Filed: Jan. 25, 2000

(86) PCT No.: PCT/US00/02051

§ 371 (c)(1),
(2), (4) Date: Apr. 29, 2002

(87) PCT Pub. No.: WO00/43552

PCT Pub. Date: Jul. 27, 2000

Related U.S. Application Data

(63) Continuation-in-part of application No. 09/236,758, filed on Jan. 25, 1999, now abandoned.

(51) Int. Cl.$^7$ .............................. C12Q 1/68; C12M 1/36; G01N 15/02; C07H 21/04; C07K 5/00
(52) U.S. Cl. .......................... 435/6; 435/7.1; 435/174; 435/283.1; 435/287.2; 435/288.7; 435/320.1; 435/325; 422/68.1; 422/82.05; 422/82.01; 356/335; 356/346; 536/23.1; 536/24.3; 530/300; 530/350
(58) Field of Search ....................... 435/6, 7.1, 174, 435/283.1, 287.2, 288.7, 320.1, 325, 4; 422/68.1, 82.05, 82.01; 356/335, 346; 536/23.1, 24.3; 530/300, 350

(56) References Cited

U.S. PATENT DOCUMENTS 5,658,732 A   8/1997  Ebersole et al.
6,159,681 A * 12/2000 Zebala ........................... 435/4
6,197,503 B1 * 3/2001 Vo-Dinh et al. ................ 435/6
6,207,369 B1 * 3/2001 Wohlstadter et al. ........... 435/6
6,448,064 B1 * 9/2002 Vo-Dinh et al. ......... 435/287.2

FOREIGN PATENT DOCUMENTS

WO   WO93/22678   11/1993
WO   WO99/27140    6/1999

OTHER PUBLICATIONS

Egholm et al ("PNA hybridizes to complementary oligonucleotides obeying the Watson–Crick hydrogen–bonding rules" Nature, 1993, 365: 566–568).*

International Search Report for International Application No. PCT/US00/02051 dated Jul. 28, 2000.

* cited by examiner

Primary Examiner—B. J. Forman
(74) Attorney, Agent, or Firm—Akerman Senterfitt

(57) ABSTRACT

An integrated biosensor system for the simultaneously detection of a plurality of different types of targets includes at least one sampling platform, the sampling platform including a plurality of receptors for binding to the targets. The plurality of receptors include at least one protein receptor and at least one nucleic acid receptor. At least one excitation source of electromagnetic radiation at a first frequency is provided for irradiating the receptors, wherein electromagnetic radiation at a second frequency different from the first frequency is emitted in response to irradiating when at least one of the different types of targets are bound to the receptor probes. An integrated circuit detector system having a plurality of detection channels is also provided for detecting electromagnetic radiation at said second frequency, the detection channels each including at least one detector.

28 Claims, 10 Drawing Sheets

DOUBLE - STRANDED DNA

HYBRIDIZATION PRINCIPLE

MULTIFUNCTIONAL AND MULTISPECTRAL BIOSENSOR DEVICES AND METHODS OF USE

CROSS-REFERENCE TO RELATED APPLICATIONS

This application claims the benefit of International Application PCT/US00/02051 filed on Jan. 25, 2000 which is a CIP of U.S. patent application Ser. No. 09/236,758 filed on Jan. 25, 1999, now abandoned, the entirety of each being specifically incorporated herein in its entirety.

STATEMENT REGARDING FEDERALLY SPONSORED RESEARCH OR DEVELOPMENT

The United States Government has certain rights in the present invention pursuant to Grant DE-AC05-96OR22464 from the United States Department of Energy.

FIELD OF THE INVENTION

This present invention provides an advanced mutifunctional biochip (AMB) that combines integrated circuit elements, electro-optical excitation and detection systems, and molecular receptor probes in a self-contained integrated microdevice. Methods for the use of such devices in the detection and quantitation of biomolecules, and their application to diagnostic and therapeutic regimens are also provided.

DESCRIPTION OF RELATED ART

Living systems possess exquisite recognition elements (e.g., antibody, enzyme, gene probes, etc.), often referred to as bioreceptors, which allow specific identification and detection of complex chemical and biological species. Biosensors exploit this powerful molecular recognition capability of bioreceptors. Due to the exquisite specificity of the DNA hybridization process, there is an increasing interest in the development of DNA bioreceptor-based analytical systems (Kumar et al., 1994; Eggers et al., 1994; Schena et al., 1995; Vo-Dinh et al., 1994; Stevenson et al., 1994; Isola et al., 1996; Alarie et al., 1992; Vo-Dinh et al., 1987a; 1987b; Vo-Dinh et al., 1991; Saiki et al., 1988; Graham et al., 1992; Steffan and Atlas, 1991; Vogelstein and Kinzler, 1992; Sambrook et al., 1989; Vo-Dinh et al., 1998a; 1998b; Isola et al., 1998; http://www.Affymetryx.com; http://www.Nanogen.com).

Most biosensors previously reported are based on fiber optic probes, glass and silica plates used as the probe substrates which are externally connected to a photo sensing system, which generally consists of a conventional detection device, such as a photomultiplier, or a charge-coupled device (CCD). In general, the sampling platform containing the probes is small (the sampling platform is often referred as to a "DNA chip" or "gene chip"), but the entire device containing excitation laser sources and detection systems (often a confocal microscope system) is relatively large, e.g. table-top size systems (e.g., the Affymetrix system). Nanogen has also developed a biochip system, but this device is mainly designed to move DNA with electric field manipulation, and has been used only for DNA samples. Until now, there is no truly integrated biochip system that comprises probes, samplers, detector as well as amplifier and logic circuitry on board and that is capable of multi-function diagnostics capability.

There is a strong interest in the development of non-radioactive bioreceptor probes using DNA, enzymes, and/or antibody probes for use in a wide variety of diagnostic and quantitative applications, such as identification of the causal agents of infectious disease, diagnosis and therapy of a variety of medical conditions, and detection of biomolecules in samples from industry, biotechnology, and the environment. The use of such techniques in the areas of agriculture, genetic engineering, agribiotechnology, and bioremediation is also contemplated to facilitate the detection and quantitation of a variety of macromolecules, including those of biological and microbiological origins.

One type of devices, often referred to as a "biochip" combines semiconductor detection system with biotechnology-based probes, and has received increasing interest. The inventor has developed a variety of self-contained biochip devices and systems (e.g., U.S. patent application Ser. No. 08/979,672, filed Nov. 26, 1997; Intl. Pat. Appl. Ser. No. PCT/US98/25294, filed Nov. 25, 1998, and U.S. patent application Ser. No. 09/236,758, filed Jan. 25, 1999, the entire contents of each of which is incorporated herein by reference in its entirety). While such biochips (as well as other currently available biochip devices) have several detection channels, they are, however, designed to use only one specific type of bioreceptor at a time, and are therefore unsuitable for simultaneous multidetection of a plurality of species. While these earlier biochip systems may be used for detecting either an individual or a plurality of a particular biochemical species on a single chip at the same time (e.g., in detecting one or more polynucleotides or in detecting one or more polypeptides, they were not devised to detect multiple biochemical species at the same time on the same chip (i.e. the simultaneous detection of polypeptides and polynucleotides on a single chip).

DEFICIENCIES IN THE PRIOR ART

Until now, most DNA biosensors previously reported are based on fiber optic probes, glass and silica plates used as the probe substrates which are externally connected to a photo sensing system, which generally consists of a conventional detection device, such as a photomultiplier, or a charge-coupled device (CCD). Although the probes on the sampling platform are small (often referred to as a 'DNA chip' or 'gene chip'), the entire device containing excitation laser sources and detection systems (often a confocal microscope system) is relatively large, e.g., tabletop size systems. Although these systems have demonstrated their usefulness in genomics research and analysis, they are laboratory-oriented and involve relatively expensive equipment.

There is a critical demand for a rapid, simple, cost-effective technique for screening samples, such as blood or other clinical samples, for the presence of biomolecules (including polynucleotides, polypeptides, etc.) to assist in the diagnosis and treatment of medical diseases, including those caused by infectious pathogens, and the like, as well as provide efficient means for quantitating such molecules in pathology and forensics samples. The development of inexpensive screening analyses that would permit simultaneous analyses of multiple biological molecules would allow rapid detection and improved treatments of many illnesses, facilitate improvements in quality control and manufacturing, as well as provide rapid, affordable devices for detection of biomolecules in the areas of environmental contamination and remediation processes.

The development of rapid and effective screening tests for simultaneous assay of two or more different types of molecules (e.g., detecting antibodies and polynucleotides in a sample on a single biochip) would also reduce the cost of diagnostic testing services, biochemical analyses and assay systems, as well as overall costs in the health care industry. For example, a critical factor in medical diagnostics is rapid, selective, and sensitive detection of biochemical substances (protein, metabolites, nucleic acids), biological species or living systems (bacteria, virus or related components) at ultra-trace levels in biological samples (e.g., tissues, blood and other bodily fluids). To achieve the required level of sensitivity and specificity in detection, it is often necessary to use a biosensor that is capable to identify and differentiate a large number of biochemical constituents in complex samples. The development of a cost-effective biochip alternative to simultaneous quantitation of pluralities of differing biological molecules would be a revolutionary advance in the fields of analytical chemistry and medicine.

To that end, there is currently a strong need for a truly advanced multifunctional biochip system that comprises the necessary probes, samplers, detectors, amplifier and logic circuitry on a single biochip useful in the detection of pluralities of different biomolecular targets. Such a system would be useful in many environments, including inter alia, diagnostic laboratories, environmental sites, remediation or hazardous materials clean-up sites, physicians' offices, health care clinics, hospitals, and even mobile analytical chemistry devices.

Likewise, there is also a need to extend the application of biochip-based sensors to the detection and quantitation of macromolecules other than polypeptides and DNAs. The development of sensors useful in the detection of molecules such as RNAs, peptide-nucleic acids (PNAs), ribozymes, antibodies, enzymes, and peptide fragments, would represent a significant advance in the art and provide new methods and devices for the detection of molecules of biological importance. Furthermore, because of recent advances in the molecular sciences, the ability to detect and quantitate biomimetics, and new classes of biologically-active molecules such as DNA adaptamers, aptamers, cyclodextrins, dendrimers, molecular imprints, and the like would benefit from the creation of biochip-based apparatus capable of detecting and quantitating these, and other biologically- and medically-relevant macromolecules.

There is also a distinct need for development of advanced multifunctional devices that permit the rapid, large-scale and cost effective analysis of pluralities of heterogeneous macromolecules, and permit the development of methods for detecting and quantitating multiple molecular species in mixed biological samples.

SUMMARY OF THE INVENTION

This present invention overcomes these and other limitations in the prior art by providing for the first time, an advanced multifunctional biochip (AMB) that is capable of simultaneous detection of two or more different biological macromolecules (or "targets"). These macromolecules may comprise a plurality of polynucleotides (including DNAs, PNAs and/or RNAs), a plurality of polypeptides, peptides, and/or proteins; a plurality of enzymes, antibodies, and/or receptors or antigens); a plurality of pathogens, organisms, microorganisms, and/or viruses, etc.); or a plurality of cells, cell types, tissues, organelles, organs, fluids, and/or other intracellular or extracellular components of a living cell. Alternatively, the biological macromolecules may be a combination of any of these or other biological compounds that may be detected using an AMB that comprises a plurality of receptor probes, orbiomimetic probes on a single device. Such design permits the simultaneous or sequential detection of a variety of targets using a single biochip device, and as such provides methods of detecting and quantitating a number of diverse biochemical compounds using a single device.

Operating Principle of the AMB Device

Biochip System

Biosensors and biochips involve two essential functions that integrate "biological recognition" and "sensing." The basic principle of an optical biosensor is to detect this molecular recognition and to transform it into an optical signal using a transducer. The biochip is a biosensor that involves the combination of integrated circuit elements, electro-optics excitation/detection system, and bioreceptor probes into a self-contained and integrated microdevice. An illustrative medical biochip device of the present invention may include: 1) an excitation light source, 2) a bioprobe, 3) a sampling platform, 4) one or more sensing elements, and 5) a signal amplification and treatment system. FIG. 1A, FIG. 1B, and FIG. 1C show schematic diagrams of the AMB device having different types of probes (polypeptides, antibody, nucleic acids, enzymes, tissues, organelles, and other receptor probes). Different possible embodiments of the AMB are schematically shown in FIG. 1A and FIG. 1B.

Biological Probes

The biochip has a unique multifunctional diagnostic capability due to the different types of bioprobes: polynucleotides such as PNA, RNA or DNA; polypeptides, such as proteins, peptides, antibodies, enzymes, and receptors; as well as tissues, organelles, and other receptor probes.

DNA Probes

Recently there has been an increasing interest in biosensor technology. Biosensors combine two important concepts that integrate "biological recognition" and "sensing." The basic principle of a biosensor is to detect this molecular recognition and to transform it into another type of signal using a transducer. The selected transducer may produce either an optical signal (i.e. optical biosensors) or an electrochemical signal (i.e. electrochemical biosensors). The bioreceptor may consist of an enzyme, an antibody, a gene fragment, a chemoreceptor, a tissue, an organelle or a microorganism.

The operation of gene probes is based on the hybridization process. Hybridization involves the joining of a single strand of nucleic acid with a complementary probe sequence (FIG. 2). Hybridization of a nucleic acid probe to DNA biotargets (e.g., gene sequences, bacteria, viral DNA) offers a very high degree of accuracy for identifying DNA sequences complementary to that of the probe. Nucleic acids strands tend to be paired to their complements in the corresponding double-stranded structure. Therefore, a single-stranded DNA molecule will seek out its complement in a complex mixture of DNA containing large numbers of other nucleic acid molecules. Hence, nucleic acid probe (i.e. gene probe) detection methods are very specific to DNA sequences. Factors affecting the hybridization or re-association of two complementary DNA strands include temperature, contact time, salt concentration, the degree of mismatch between the base pairs, as well as the length and concentration of the target and probe sequence(s).

Probes Based on cDNAs

The AMB device can also be used to monitor gene expression using cDNA probes. Genes, which are contained within in the DNA of a cell's nucleus, contain codes that essentially are recipes for tens of thousands of proteins. The code-containing regions of the gene (exons), however, are often separated by much non-coding DNA (introns). A cDNA molecule is a laboratory-made version of a gene that contains only its information-rich regions; these molecules provide a way for genome researchers to fast-forward through the genome to biologically important areas.

cDNA molecules are made using molecules of RNA (similar to DNA) obtained from living cells. In the cell, expression of the information from DNA into a protein first requires transcription of DNA into nuclear RNA molecules. These nuclear RNAs have non-coding regions that are processed out in the course of forming cytoplasmic RNAs (messenger RNAs). Because mRNAs are too fragile to withstand laboratory manipulations, scientists make sturdy double-stranded copies called complementary (or copy) DNA, or cDNAs.

All DNA clones derived from a particular tissue constitute a library of clones representing the genes that were expressed when the source tissue was harvested. The analysis of libraries from many different tissues, obtained under a variety of physiological conditions, will be necessary to decipher the organ-specific patterns of gene expression.

Antibody Probes

Antibodies are the product of immune system cells (B cells) when those cells are exposed to antigenic substances or molecules. The antibodies produced following antigen exposure have recognition/binding sites for specific molecular structures (or substructures) of the antigen. Just as specific configurations of a unique key enable it to enter a specific lock, so in an analogous manner, an antigen-specific antibody "fits" its unique antigen. Thus, an antigen-specific antibody interacts with its unique antigen in a highly specific manner, so that the total three-dimensional biochemical conformation of antigen and antibody are complementary. This molecular recognition feature of antibodies is the key to their usefulness in immnunosensors; molecular structural recognition allows one to develop antibodies that can bind specifically to chemicals, biomolecules, microorganism components, etc. Such antibodies may then be used as specific "probes" to identify an analyte of interest that is often present in extremely small amounts, among a myriad of other chemical substances. Another property of antibodies of great importance to their role in immunosensors is the strength or avidity/affinity of the antigen-antibody interaction. Since the antigen-antibody surfaces lie in close proximity to one another, a variety of molecular interactions may take place and the overall strength of such interactions can be considerable, with correspondingly highly favorable association and equilibrium constants.

General immunoassay measurement strategies can be divided into three categories: direct, competitive (Tromberg et al., 1987), and sandwich assays (Vo-Dinh et al., 1987a; 1987b). FIG. 3 shows a schematic of the three strategies. Direct assays are performed by simply incubating the naturally fluorescent antigens with excess amounts of antigens. The sensitivity is directly proportional to the amount of antibody present and the response is directly proportional to the amount of antigen present. In competitive assays, fluorescent-labeled antigen is used to compete with unlabeled (non-fluorescent) antigen for a limited number of antibody binding sites. Antibody-bound antigen (labeled and unlabeled) is separated from free antigen and the fluorescence of the antibody-bound labeled antigen is measured. The signal intensity of the bound phase is inversely proportional to the concentration of the unlabeled antigen. The higher the fluorescent signal, the lower the unlabeled antigen concentration. Sandwich assays are performed by incubating the antigens with a primary (first) antibody that is present in excess concentrations. The antibody-antigen complex is then incubated with a second fluorescently labeled antibody that binds to the first antibody. Unbound labeled antibody is rinsed away and the bound labeled antibody is measured. Sensitivity is related to the amount of primary antibodies present with the response proportional to the antigen concentration.

Multichannel Sampling Platform

Immobilization of bioprobes on a multiarray (e.g., those of up to about 100 or about 200, or about 400, or even about 1000 or so channels) sampling platform can be performed onto a transducer detection surface to ensure optimal contact and maximum detection. When immobilized onto a substrate, the bioprobes are stabilized and, therefore, can be reused repetitively. In one illustrative embodiment, the hybridization is performed on an immobilized target or a probe molecule attached on a solid surface such as a nitrocellulose, a nylon membrane or a glass plate using one of the well-known methods for binding a nucleic acid molecule to a particular substrate or support. The method most commonly used for binding bioprobes to glass involves silanization of the glass surface followed by activation with carbodiimide or glutaraidehyde. Immobilization of the bioreceptor probes onto a substrate or membrane and subsequently attaching the membrane to the transducer detection surface is another approach that can be used.

Integrated Electro-optic Microchip System

The instrumental system developed for this work involved integrated electro-optic sensing photodetectors for the biosensor microchips. The inventor has developed the design of the electro-optic systems for the microchip detection elements, the fabrication of which is possible partly through the capability of fabricating multiple optical sensing elements and microelectronics on a single integrated circuit (IC). An example of such integration is a two-dimensional array of optical detector amplifiers integrated on a single IC chip.

The detailed design of an illustrative electro-optic microchip has been described in (U.S. patent application Ser. No. 08/979,672, incorporated herein by reference in its entirety). An important element in the development of the biochip involves the design and development of an IC electro-optic system for the microchip detection elements using the CMOS technology. With this technology, highly integrated biosensors are made possible partly through the capability of fabricating multiple optical sensing elements and microelectronics on a single IC. A two-dimensional array of optical detector-amplifiers was integrated on a single IC chip. Such an integrated microchip system is not currently available commercially.

The inventor and others have developed two types of biochips, one using phototransistors (Vo-Dinh et al., 1998a; 1998b) and the other using photodiode systems (Vo-Dinh, 1998a; 1998b). Exemplary biochip IC systems based on photodiode circuitry typically comprise 16 channels (e.g., in a 4×4 array), or larger (e.g., a 100-channel system that comprises a 10×10 array). The biochips include a large-area, n-well integrated amplifier-photodiode array that has been designed as a single, custom integrated circuit (IC), fabricated for the biochip. This IC device is coupled to the multiarray sampling platform and is designed for monitoring very low light levels. The individual photodiodes have 900-$\mu$m square size and are arrayed on a 1-mm spacing grid. The photodiodes and the accompanying electronic circuitry were fabricated using a standard 1.2-micron n-well CMOS process. The use of this type of standard process allows the production of photodiodes and phototransistors as well as other numerous types of analog and digital circuitry in a single IC chip. This feature is the main advantage of the CMOS technology in comparison to other detector technologies such as charge-coupled devices or charge-injection devices. The photodiodes themselves are produced using the n-well structure that is generally used to make resistors or as the body material for transistors. Since the anode of the diode is the p-type substrate material, which is common to every circuit on the IC chip, only the cathode is available for monitoring the photocurrent and the photodiode is constrained to operate with a reverse bias.

The inventor has designed an analog multiplexer that allows any of the elements in the array to be alternately connected to a single amplifier. Optionally each photodiode could be supplied with its own amplifier. The multiplexer for a 4×4-array device may, therefore, be made from 16 cells. Each cell has two CMOS switches that are controlled by the output of the address decoder cell. Each cell has a unique 4-bit address. One switch is open only when it is being addressed while the other switches are closed. This process connects the addressed diode to one amplifier while all the others are connected in parallel to the other amplifier. This arrangement allows connecting a 4×4 (or 10×10) array of light sources (different fluorescent probes, for example) to the photodiode array and reading out the signal levels sequentially. With some modification, a parallel reading system may also be utilized. Using a single photodiode detector would require mechanical motion to scan the source array. The additional switches and amplifier serve to correctly bias and capture the charge generated by the other photodiodes. The additional amplifier and switches allow the IC to be used as a single, large area (nearly 4 mm$^2$) photodetector.

The integrated circuit biochips of the present invention also further comprise an integrated circuit that includes an optical transducer and associated optics and circuitry for generating an electrical signal in response to light or other radiation indicative of the presence of a target biological species, particularly a nucleic acid. The chip may also include a support for inmmobilizing a bioprobe, which is preferably a nucleic acid. In particular embodiments, a target nucleic acid may be tagged or labeled with a substance that emits a detectable signal; for example, luminescence. Alternatively, the bioprobe attached to the immobilized bioprobe may be tagged or labeled with a substance that emits a detectable or altered signal when combined with the target nucleic acid. The tagged or labeled species may be fluorescent, phosphorescent, or otherwise luminescent, or it may emit Raman energy or it may absorb energy.

The highly integrated biosensors of the present invention are advantageous in part because of fabricating multiple optical sensing elements and microelectronics on a single integrated circuit, and further combining the chip in preferred embodiments with a plurality of molecular hybridization probes (Geiger et al., 1990; Aubert et al., 1998). When the probes selectively bind to a targeted species, a signal is generated that is picked up by the chip. The signal may then be processed in several ways, depending on the nature of the signal.

In one aspect, the present invention concerns an integrated system that includes (1) a targeted nucleic acid sequence in combination with a biological probe which is modified to receive light or other radiation of a first frequency and thereby to emit light or other radiation of a different frequency than the first frequency, and (2) to detect the emitted radiation by means of a phototransducer. The target nucleic acid is typically a uniquely characteristic gene sequence of a pathogen such as a fungus, bacteria, or virus, or other distinct nucleic acid species such as may be found in mutant mammalian cells or in individuals with inherited errors of metabolism. The target nucleic acid is modified or labeled to include a tag or label that emits a signal upon exposure to an incident light or other radiation.

The target nucleic acid may be immobilized onto the integrated microchip that also supports a phototransducer and related detection circuitry. Alternatively, a gene probe may be immobilized onto a membrane or filter that is then attached to the microchip or to the detector surface itself. This approach avoids the need to bind the bioreceptor directly to the transducer and thus is attractive for simplifying large-scale production.

In one preferred embodiment of the invention, light of a highly directional or focused nature is impinged on a target nucleic that inherently or by virtue of an appropriate tag or label will emit a detectable signal upon irradiation. The irradiation may be provided by a suitable light source, such as a laser beam or a light-emitting diode (LED). With Raman, fluorescence or phosphorescence detection modes, the incident light is further kept separate from the emitted light using different light paths and/or appropriate optical filters to block the incident light from the detector.

For example, in the detection of a polynucleotide, one or more target nucleic acid sequence(s) are preferably hybridized with a nucleic acid sequence that is selected for that purpose (bioprobe). The selected bioprobe(s) are immobilized on a suitable substrate, either on the biochip itself or on a membrane type material that is then contacted or attached to the chip surface. The bioprobe may be labeled with a tag that is capable of emitting light or other non-radioactive energy. Upon hybridization with a target nucleic acid sequence, the hybrid product can be irradiated with light of suitable wavelength to emit a signal in proportion to the amount of target nucleic acid hybridized. The labeled bioprobe may comprise a labeled molecular bioreceptor. Known receptors are advantageous to use because of their known ability to selectively bind with the target nucleic acid sequence. In certain particular examples, the bioreceptor itself may exhibit changes in light emission when its cognate is bound.

In certain applications, it may be desirable to increase the amount of biotarget when only trace quantities are present in a sample. For example, the disclosed biochips are compatible for use with polymerase chain reaction (PCR™), a well-known technique used in amplifying polynucleotide sequences.

There are several methods for selectively identifying biological species, including antibody detection and assay as in the well-known enzyme-linked immuno-suppressant assays (ELISAs) employing molecular hybridization techniques. Generally speaking, it is possible to identify sequence-specific nucleic acid segments, and to design sequences complementary to those segments, thereby creating a specific probe for a target cell, such as different pathogen cells or even mammalian cells that have mutated from their normal counterparts. In principle, one can design complementary sequences to any identified nucleic acid segment. In many instances, unique sequences specific to an organism may be used as probes for a particular organism or cell type. The quantitative phenotypic analysis of yeast deletion mutants, for example, has utilized unique nucleic acid sequence identifiers to analyze deletion strains by hybridization with tagged probes using a high-density parallel array (Shoemaker et al., 1996).

Hybridization involves joining a single strand of nucleic acid with a complementary probe sequence. Hybridization of a nucleic acid probe to nucleic acid sequences such as gene sequences from bacteria, or viral DNA offers a very high degree of accuracy for identifying nucleic acid sequences complementary to that of the probe. Nucleic acid strands tend to be paired to their complements in double-stranded structures. Thus, a single-stranded DNA molecule will seek out its complement in a complex mixture of DNA containing large numbers of other nucleic acid molecules. Hence, nucleic acid probe (e.g., gene probe) detection methods are very specific to DNA sequences. Factors affecting the hybridization or reassociation of two complementary DNA strands include temperature, contact time, salt concentration, the degree of mismatch between the base pairs, and the length and concentration of the target and probe sequences. In perhaps the simplest procedure, hybridization is performed on an immobilized target or a probe molecule attached on a solid surface such as a nitrocellulose or nylon membrane or a glass plate.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DESCRIPTION OF ILLUSTRATIVE EMBODIMENTS

SOME ADVANTAGES OF THE INVENTION

Figure 1A:
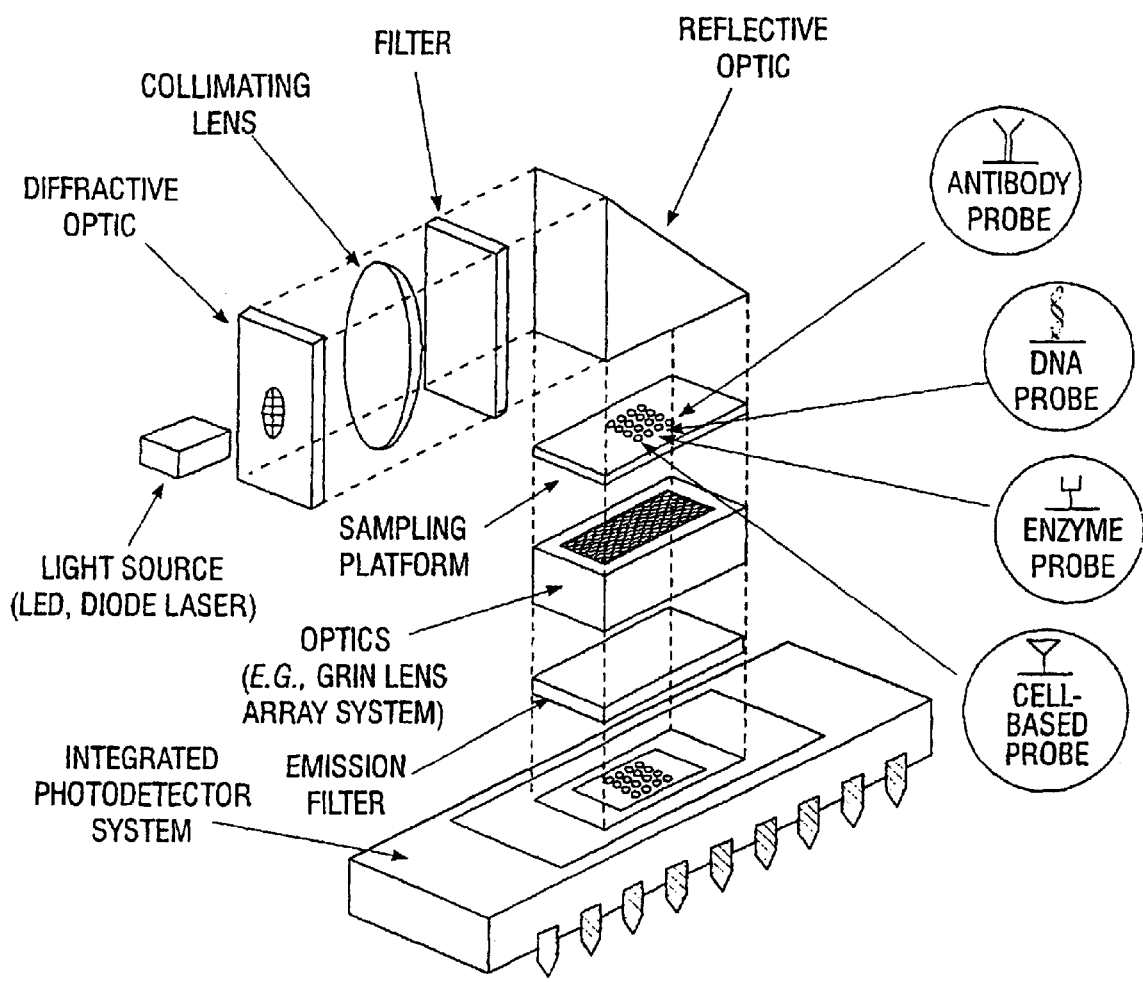
FIG. 1A illustrates a schematic diagram of an exploded view of one example of the advanced multifunctional biochip device of the invention.
Figure 1B:
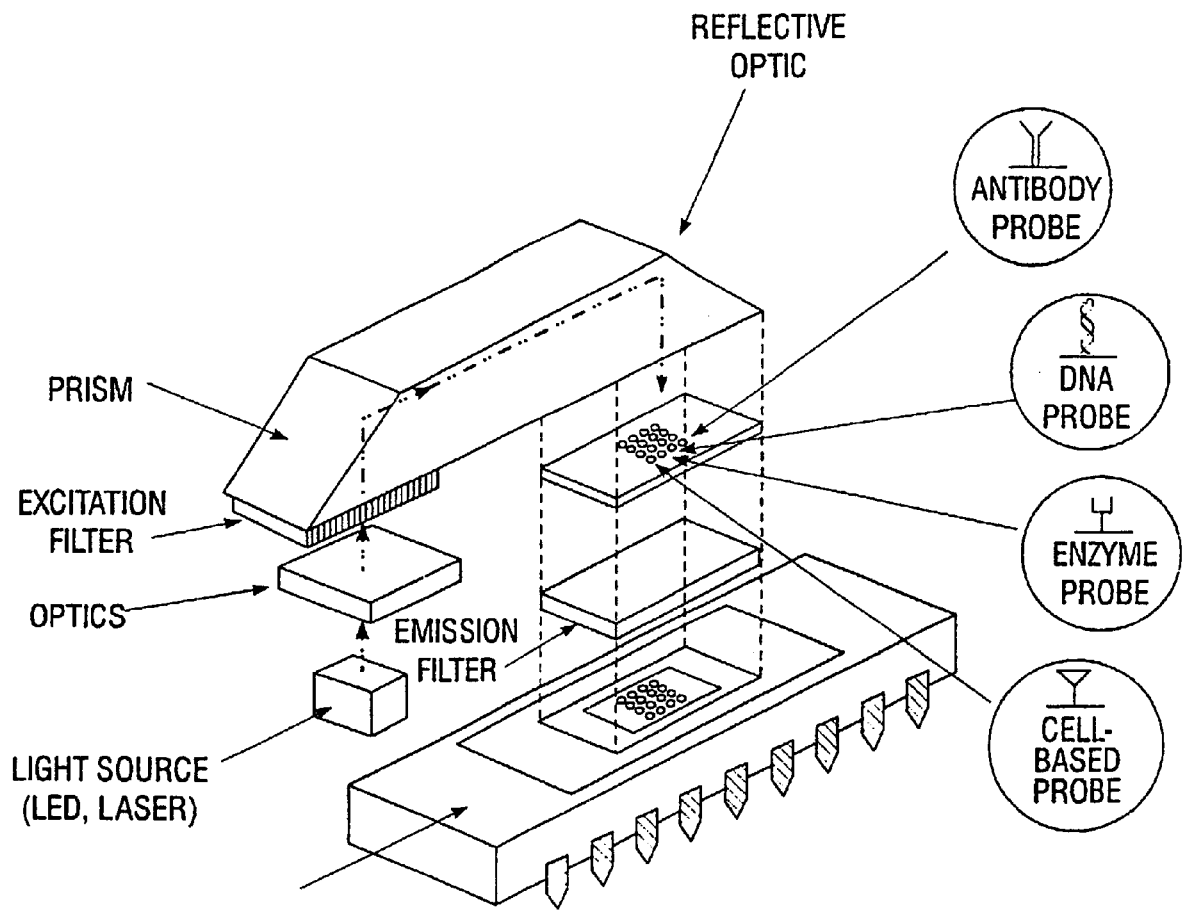
FIG. 1B illustrates a schematic diagram of one possible configuration utilizing a prism to convert an optical signal into an electrical signal suitable for data digitization and capture by a computer.
Figures 1, 1C:
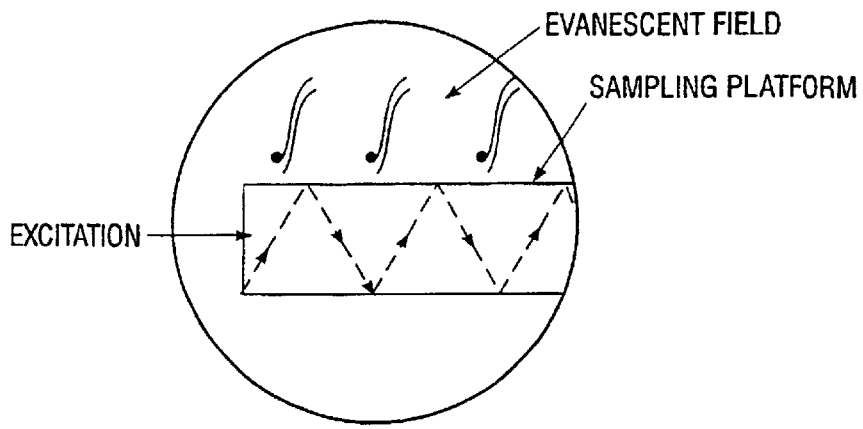
FIG. 1C and FIG. 1C-1 illustrates a schematic diagram of an exploded view of another example of the advanced multifunctional biochip device of the invention that uses a laser or an integrated light emitting diode (LED) light source and phototransistor detection device.
Figure 1C:
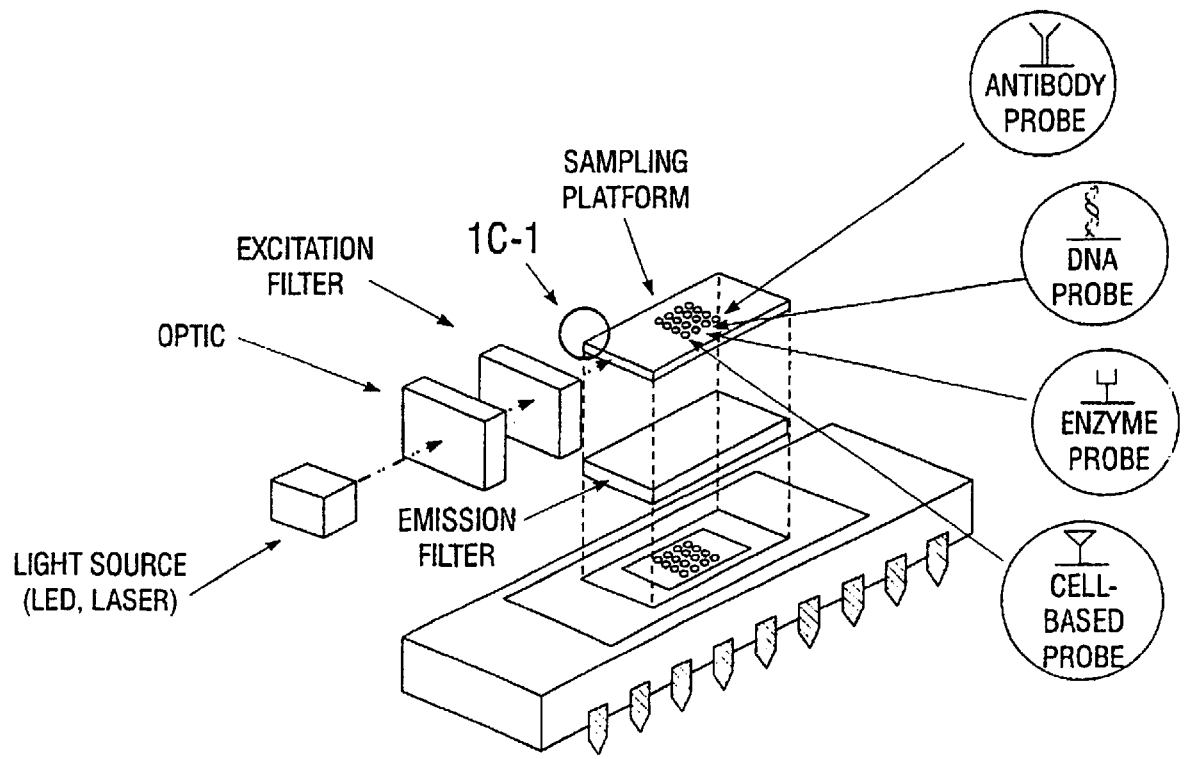
Figure 2A:
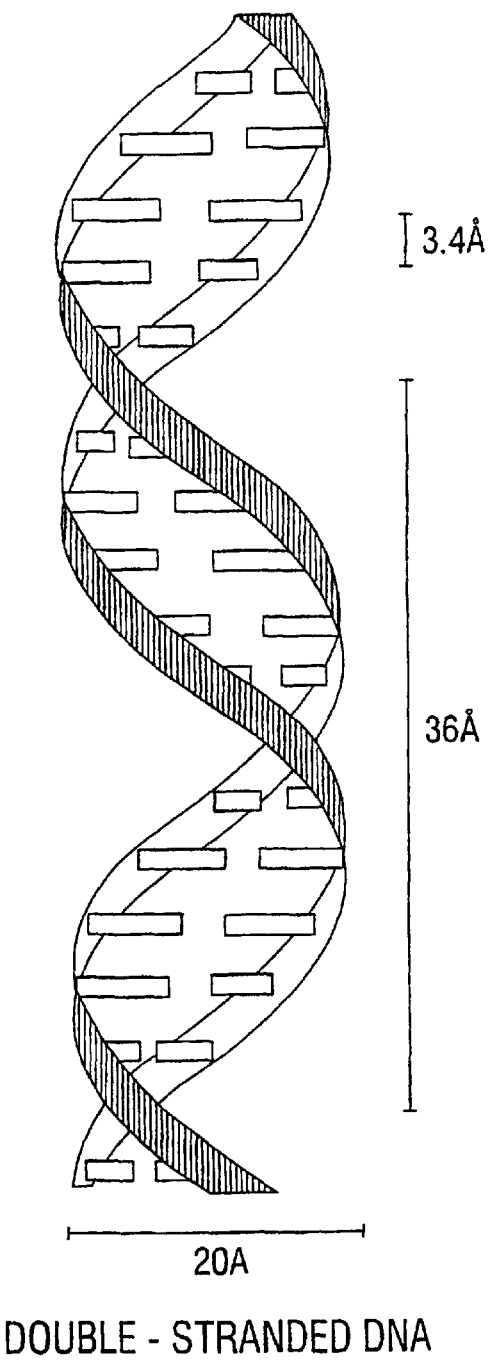
FIG. 2 illustrates schematically the principle of nucleic acid hybridization that permits the use of nucleic acid sequences as "probes" in the AMB device to detect corresponding complementary "target" sequences in a sample.
Figure 2B:
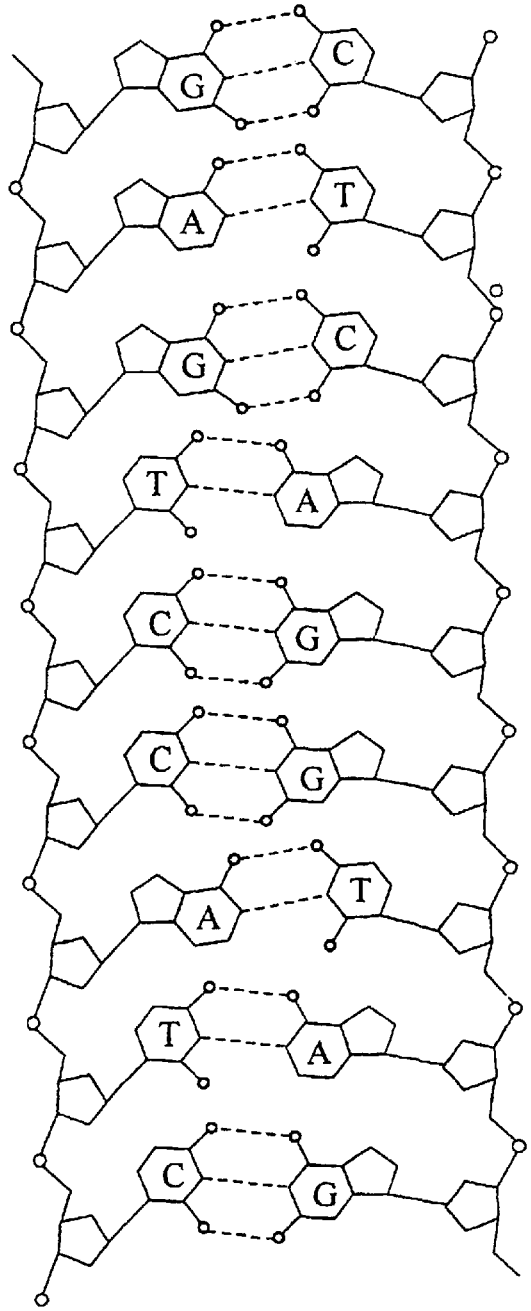
Figure 3:
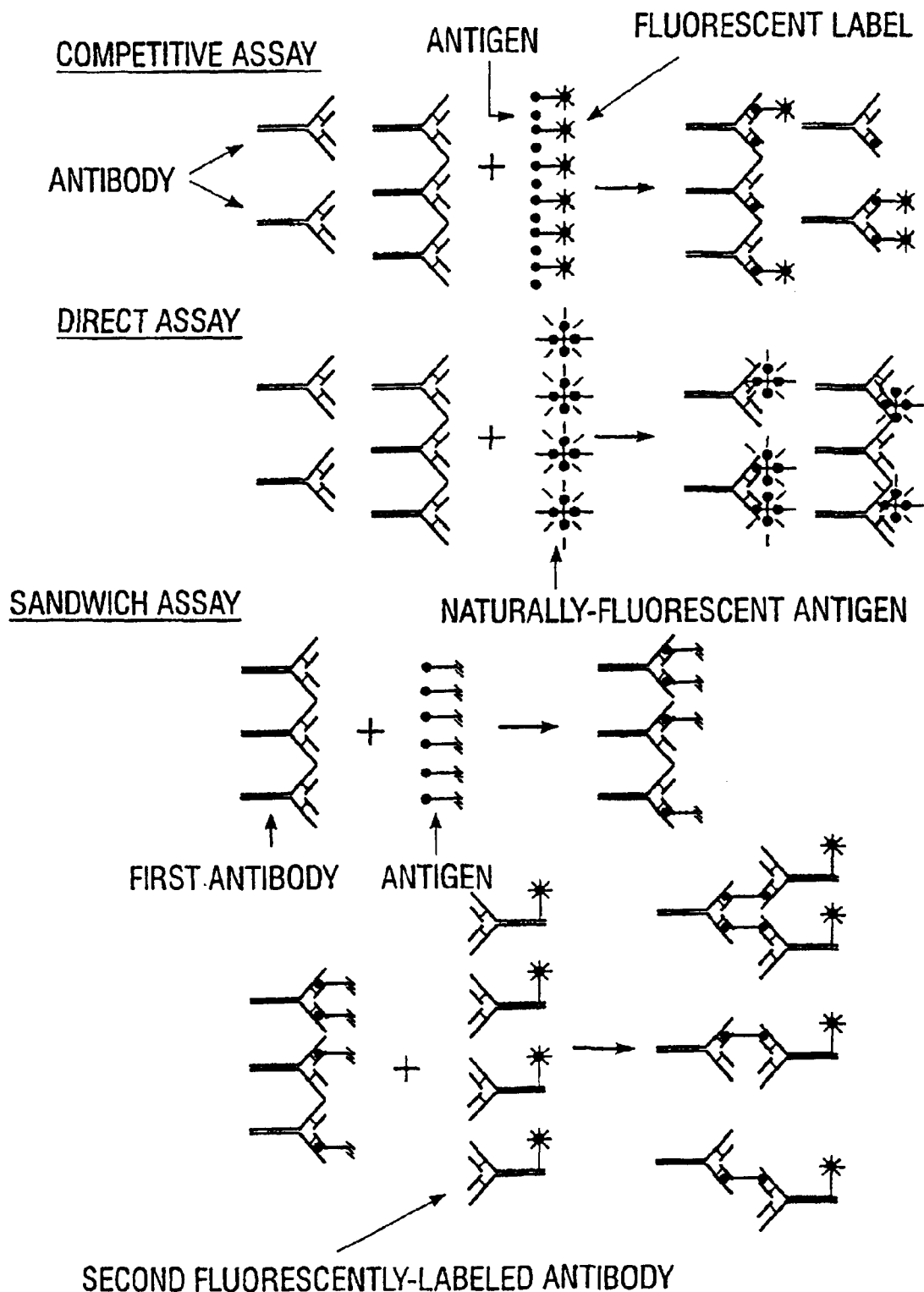
FIG. 3 illustrates various methods for immunosensing using competitive, direct, or sandwich assays.

The advanced multifunctional biochip system of the present invention offers a unique combination of performance capabilities and analytical features of merit not available in any other analysis system currently available. With its multichannel and multifunctional capabilities, the advanced biochip technology is the only current system that allows simultaneous detection of multiple biomolecular targets simultaneously. The AMB devices of the present invention find utility in a wide variety of applications, and particularly in the areas of medical diagnostics, gene identification, and mapping, polynucleotide sequencing, environmental bioremediation, and related biotechnology applications.

The present biochip also offers several advantages in size, performance, fabrication, analysis and production cost. The small sizes of the probes (microliter to nanoliter) minimize sample requirement and reduce reagent and waste requirement. Highly integrated systems lead to a reduction in noise, and an increase in signal due to the improved efficiency of sample collection and the reduction of interfaces. The capability of large-scale production using low-cost IC technology is an important advantage. The assembly process of various components is made simple by integration of several elements on a single chip. For medical applications, this cost advantage will allow the development of extremely low cost, disposable biochips that can be used for in-home medical diagnostics of diseases without the need of sending samples to a laboratory for analysis.

Designs and Operating Principle of Multifunctional Biochips

Two fundamental operating principles of a biosensor are: (1) 'biological recognition' and (2) 'sensing'. The basic principle of a biosensor is to detect this molecular recognition and to transform it into another type of signal using a transducer. There are different types of transducers that may produce either an optical signal (i.e. optical biosensors) or an electrochemical signal (i.e. electrochemical biosensors), or a mass-based signal (e.g., microbalances, surface-acoustic wave devices, micro-cantilevers). There are also different types of bioreceptors that may consist of an enzyme, an antibody, a nucleic acid fragment, a chemoreceptor, a tissue, an organelle or a microorganism. Sometimes a synthetic molecule, often called biomimetic receptor (e.g., synthetic antibody, molecular imprint) can be used to mimic the properties of is biological receptors.

The inventor previously developed an integrated polynucleotide detection biochip that incorporates selected nucleic acid probe(s) and a detection system into a single, self-contained microdevice. This biochip involves the combination of integrated circuit elements, electro-optics excitation/detection system, and DNA-based bioreceptor probes into a self-contained and integrated microdevice. A basic DNA biochip includes: (1) excitation light source with related optics; (2) a bioprobe; (3) a sampling platform and delivery system; (4) an optical detector with associated optics and dispersive device; and (5) a signal amplification/treatment system.

Construction of a DNA biochip involves integration of several basic elements of very different natures. The basic steps include: (a) selection or development of the bioreceptor; (b) selection of the excitation source; (c) selection or development of the transducer; and (d) integration of the excitation source-bioreceptor-transducer system.

The development of the DNA biochip comprises three major elements. The first element involves the development of a bioreceptor probe system: a micro-array of DNA probes on a multiarray sampling platform. The second element is focused on the development of non-radioactive methods for optical detection: the fluorescence technique. The third element involves the development of an integrated electro-optic IC system on a single chip for biosensing: photodiode-amplifier microchip using the CMOS technology.

Operating Principle of Polynucleotide Probes: Molecular Hybridization

Whereas the use of immunological probes is based on antibody-antigen reactions, the operation of gene probes is based on the hybridization process, which is one of the most powerful and useful techniques in molecular genetics. Hybridization involves the joining of a single strand of nucleic acid with a complementary probe sequence. Hybridization of a nucleic acid probe to DNA biotargets (e.g., gene sequences, bacteria, viral DNA, p53 cancer gene mutation etc.) offers a very high degree of accuracy for identifying DNA sequences complementary to that of the probe. Nucleic acids strands tend to be paired to their sequence complements (i.e. adenine-thymine, guanine-cytosine pairing) in the corresponding double-stranded structure. A single-stranded DNA molecule will seek out its complement in a complex mixture of DNA containing large numbers of other nucleic acid molecules. Various types of gene probes have been developed that are labeled with fluorescent (Isola et al., 1996; Vo-Dinh et al., 1998a; 1998b) or Raman labels (Vo-Dinh et al., 1998a; 1998b; Isola et al., 1998).

Micro-sampling Platform

DNA probes can be directly or indirectly immobilized onto the biochip transducer's sensing element to ensure optimal contact and maximum detection. When immobilized onto a substrate, the gene probes can be reused repeatedly. In one embodiment, hybridization is performed on an immobilized target or a probe molecule attached on a solid surface. DNA can be bound to different types of support materials using several methods. The method commonly used for binding DNA to glass involves silanization of the glass surface followed by activation with carbodiimide or glutaraldehyde.

Another embodiment involves immobilizing the gene probes onto a membrane platform that is placed on the transducer detection surface. In this manner, there is no need to bind the bioreceptor onto the biochip transducer, which may facilitate easier large-scale production.

In still another embodiment, 5'-terminal protecting groups are selectively removed from growing polynucleotide chains in pre-defined regions of a support (such as glass) by controlled exposure to light through a photolithographic mask (Fodor et al., 1991; McGall et al., 1997). This method may be used to fabricate polynucleotide probe arrays with densities as high as about $10^6$ unique probe sequences per $cm^2$.

Plastic plates (often used in multi-well format) suitable for direct adsorption of DNA can be used to develop sampling platforms for the biochip. Chemically activated plates suitable to bind DNA by covalent linkage are also commercially available for use (CoStar, Cambridge, Mass.). Multiarrays of sample spots are produced, and liquid solutions of DNA are dispensed onto the sampling platform using a pneumatic Picopump (World Precision Instruments, Sarasota, Fla.). The Picopump is capable of producing regular microspots with diameter size range of 500–800 $\mu m$, which can be selected to match the size of the biochip detector elements. The DNA sample is loaded into a small diameter glass capillary, which is held a few millimeters above the sampling platform. The membrane is held in place on a vacuum flask fitted with a metal mesh frit. The vacuum procedure served two important purposes. First the vacuum applied to the membrane improves the reproducibility of the spotting by maintaining the membrane flat against the metal mesh surface. The vacuum procedure also has a shortening effect on the sample drying process, which decreased the sample spot size by preventing the spread of sample though the sampling platform. The biochip forma can be designed to be compatible to polymerase chain reaction (PCR™), which is an important technique allowing replication of defined DNA sequences, thereby amplifying the detection of these sequences.

Biosensor Probes

The development of biosensor technologies for detection of trace quantities of biological species in complex systems is important for many biomedical and environmental applications. Spectroscopic chemical sensors and biosensors have been developed using laser induced fluorescence, room temperature phosphorescence, surface enhanced Raman spectroscopy, antibody based immunofluorescence and gene probe Raman sensing methods, including gene probes having surface-enhanced Raman scattering labels to enhance the selectivity and sensitivity of chemical sensors and biosensors (Vo-Dinh et al., 1994).

The present invention uses spectroscopic techniques such as luminescence with visible and near-infrared (NIR) labels is a useful detection scheme for gene biosensors without having the limitation of radioactive methods.

Non-radioactive probes, particularly gene probes, are desirable because of their selectivity in addition to avoiding the hazards involved with radioactive materials. Recognition and detection of biological species is based on the principle that cell specific nucleic acid sequences can be specifically recognized and can be combined with a receptor that specifically binds with that species. Such receptors include, for example, antibodies, enzymes, cells, bacterial probes, complementary nucleic acids, or nucleic acids that selectively hybridize with a cell-specific nucleic acid sequence. Receptors may be found and employed in the form of organelles, tissue components, chemoreceptors or even whole cells or microorganisms. Other types of receptors may include biomimetic materials such as cyclodextrins, molecular imprint materials, etc.

Gene probes operate on a hybridization process. Hybridization involves joining of a single strand of nucleic acid with a complementary probe sequence. Hybridization of a nucleic acid probe to a biotarget such as bacterial or viral DNA or RNA or selected gene segments, offers a high degree of accuracy for identifying nucleic acid sequences complementary to the probe. Nucleic acid strands tend to be paired with complementary strands, such as is typically found in double-stranded DNA structures. Therefore, a single-stranded DNA (or RNA) will seek out its complement in a complex mixture of DNA containing large numbers of other nucleic acid molecules. Nucleic acid probe or gene probe detection methods are specific to DNA sequences. Factors affecting the hybridization or reassociation of two complementary DNA strands include temperature, contact time, salt concentration, the degree of mismatch between the base pairs, and the length and concentration of the target and probe sequences.

Peptide Nucleic Acid Compositions

In certain embodiments, the inventor contemplates the use of peptide nucleic acids (PNAs) in the practice of the methods of the invention. PNAs are DNA mimics in which the nucleobases are attached to a pseudopeptide backbone (Good and Nielsen, 1997). PNAs can be utilized in a number of methods that traditionally have employed RNAs or DNAs. Often PNA sequences perform better in techniques than the corresponding RNA or DNA sequences and have utilities that are not inherent to RNA or DNA. An excellent review of PNA including methods of making, characteristics of, and methods of using, is provided by Corey (1997) and is incorporated herein by reference.

Methods of Making PNAs

According to Corey, PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass., USA). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

Modifications can be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Rusckowski et al., 1997). U.S. Pat. No. 5,700,922 discusses PNA-DNA-PNA chimeric molecules and their uses in diagnostics, modulating protein in organisms, and treatment of conditions susceptible to therapeutics.

Physical Properties of PNAS

In contrast to DNA and RNA, which contain negatively charged linkages, the backbone of a PNA is neutral. In spite of this dramatic alteration, PNAs recognize complementary DNA and RNA by Watson-Crick pairing (Egholm et al, 1993), validating the initial modeling by Nielsen et al., (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al., have shown that support-bound PNAs can be used to detect hybridization events (Wang et al., 1996a; 1996b).

As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996a; 1996b; Carlsson et al., 1996; Thiede et al., 1996; Webb and Hurskainen, 1996; Perry-O'Keefe et al., 1996).

Antibody Compositions and Methods of Making

In particular embodiments, the inventor contemplates the use of antibodies, either monoclonal or polyclonal that bind to one or more selected polypeptides and that may be employed as a reporter molecule for the detection of particular target polypeptides. Alternatively, the use of labeled polypeptide antigens to detect particular target antibodies in a given sample having specificity for the labeled antigen is also contemplated by the inventor to be useful in the identification of particular antigen:antibody pairs. Means for preparing and characterizing antibodies are well known in the art (see, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified polypeptide or peptide. The immunizing composition is administered in a manner effective to stimulate antibody-producing cells. Rodents such as mice and rats are preferred animals, however, the use of rabbit, sheep, or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

ELISAs

The techniques of ELISAs may be used in conjunction with the invention, when the product of interest to be detected is a polypeptide, and the detector substrate on the chip is an antibody. Alternatively, ELISA techniques may be utilized when the detector substrate on the chip is a polypeptide and the product of interest to be detected is an antibody having binding specificity for the detector polypeptide or peptide antigen. In both embodiments, either the antibody or the polypeptide may be fluorescently labeled for detection by the biochip system.

In an ELISA assay, proteins or peptides incorporating antigenic sequences are immobilized onto a selected surface, preferably a surface exhibiting a protein affinity such as a polystyrene support. After washing to remove incompletely adsorbed material, it is desirable to bind or coat the support with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or a particular clinical or biological sample to be tested in a manner conducive to immune complex (antigen/antibody) formation. Such conditions preferably include diluting the antisera with diluents such as BSA, bovine gamma globulin (BGG) and phosphate buffered saline (PBS)Tween®. These added agents also tend to assist in the reduction of nonspecific background. The layered antisera is then allowed to incubate for from about 2 to about 4 hr, at temperatures preferably on the order of about 25° C. to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the presence and quantitation of the immunocomplex formation may then be determined using the biochip system.

Template-dependent Amplification

A number of template dependent processes are available to amplify selected polynucleotide sequences in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase (QβR) described in Intl. Pat. Appl. Publ. No. PCT/US87/00880, (specifically incorporated herein by reference in its entirety), may also be used as still another amplification method in the present invention. In this method, a replicative sequence of RNA that has a region complementary to that of a target is added to a sample in the presence of an RNA polymerase. The polymerase will copy the replicative sequence, which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids that involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Still other amplification methods have been described in Great Britain Pat. Appl. No. 2 202 328, and in Intl. Pat. Appl. Publ. No. PCT/US89/01025 (each of which is incorporated herein by reference in its entirety). These may also be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released and is then bound by excess probe. Cleavage of the labeled probe signals the presence of the target sequence.

Other nucleic acid amplification procedures include transcription-based amplification systems (TAS) (Kwoh et al., 1989; Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has target-specific sequences. Following polymerization, DNA/RNA hybrids are digested with RNase H while double stranded DNA molecules are heat denatured again. In either case the single stranded DNA is made fully double stranded by addition of second target polypeptide-specific primer, followed by polymerization. The double stranded DNA molecules are then multiply transcribed by a polymerase such as 17 or SP6. In an isothermal cyclic reaction, the RNAs are reverse transcribed into double stranded DNA, and transcribed once against with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase 1), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR™" (Ohara, et al. 1989) which are well known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of polynucleotide sequences of the present invention.

Ribozymes

Ribozymes are enzymatic RNA molecules that cleave particular mRNA species. In certain embodiments, the inventor contemplates the selection and utilization of ribozymes capable of cleaving RNA segments, and the resulting detection of such mRNAs or ribozymes utilizing the methods and the integrated circuit biochips of the present invention.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992); examples of hairpin motifs are described by Hampel et al. (Eur. Pat. EP 0360257), Hampel and Tritz (1989), Hampel et al. (1990) and Cech et al. (U.S. Pat. No. 5,631,359; an example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described by Cech et al. (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Oligonucleotide Synthesis Methods

The nucleotide segments that are used as probes according to the invention may be synthesized using chemical synthesizers and standard procedures. In the use of the nucleotide segments as probes, the particular probe is labeled with any suitable label known to those skilled in the art, including the non-radioactive labels employed with the present biosensor devices. A probe labeled with a detectable label can be constructed from a nucleotide sequence complementary to the DNA sample using standard methodologies. The probe and sample can then be combined in a hybridization buffer solution and held at an appropriate temperature until annealing occurs. Thereafter, the membrane or substrate to which the sample is bound is washed free of extraneous materials, leaving the sample and bound probe molecules typically detected and quantified by the biosensor device.

Non-radioactive labels include, for example, ligands such as biotin or thyroxin, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using labels having different fluorescence wavelength maxima.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed are due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, amino acid sequences can be prepared by equivalent nucleotide sequences encoding the same amino acid sequence of the protein or peptide. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein that do not alter the protein secondary structure, or if the structure is altered, the biological activity is substantially retained.

Immobilization Techniques

The bioprobes of the present invention may be directly or indirectly immobilized onto a transducer detection surface to ensure optimal contact and maximum detection. For direct immobilization, the probes are directly attached to the surface of the biosensor. However, when indirect immobilization is desired, the probes may be immobilized onto a solid support such as a substrate, a filter, or a membrane, that may be affixed to the biosensor and then removed to be re-used repeatedly. In general terms, hybridization is performed on an immobilized nucleic acid target or a probe molecule is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photo-polymers (which contain photoreactive species such as nitrenes, carbenes and ketyl radicals capable of forming covalent links with target molecules.

Binding of the bioprobe to a selected support may be accomplished by any of several means. For example, poly-nucleotides are commonly bound to glass by fire silanizing the glass surface, then activating with carbodiimide or glutaraldehyde. Alternative procedures may use reagents such as 3-glycidoxypropyltrimethoxysilane (GOP) or ami-nopropyltrimethoxysilane (APTS) with DNA linked via amino linkers incorporated either at the 3' or 5' end of the molecule during DNA synthesis. Polynucleotides may be bound directly to membranes using ultraviolet radiation. With nitrocellulose membranes, the DNA probes are spotted onto the membranes. A UV light source (Stratalinker, from Stratagene, La Jolla, Calif.) is used to iradiate DNA spots and induce cross-linking. An alternative method for cross-linking involves baking the membranes e.g., at 80° C. for two hours in vacuum.

Specific bioprobes may first be immobilized onto a membrane and then attached to a membrane in contact with a transducer detection surface. This method avoids binding the bioprobe onto the transducer and may be desirable for large-scale production. Membranes particularly suitable for this application include nitrocellulose membrane (e.g., from BioRad, Hercules, Calif.) or polyvinylidene difluoride (PVDF) (BioRad, Hercules, Calif.) or nylon membrane (Zeta-Probe, BioRad) or polystyrene base substrates (DNA.BIND™ Costar, Cambridge, Mass.).

Polynucleotide Hybridization Probes and Primers

In one embodiment, the invention provides a method for detecting particular nucleic acid sequences in a sample. The method generally involves obtaining sample nucleic acids suspected of containing the polynucleotide of interest; contacting the sample nucleic acids with a bioprobe that comprises an isolated nucleic acid segment substantially complementary to the sample nucleic acids and a suitable detection label, under conditions effective to allow hybridization of substantially complementary nucleic acids; and detecting the hybridized complementary nucleic acids thus formed.

Nucleic acid molecules having sequence regions consisting of contiguous nucleotide stretches of about 17 to about 50, or even up to and including sequences of about 100–200 nucleotides or so, identical or complementary to the target DNA sequence, are particularly contemplated as hybridization probes for use in, e.g., Southern blotting. Intermediate-sized fragments will also generally find use in hybridization embodiments, wherein the length of the contiguous complementary region may be varied, such as between about 20 and about 45, or between about 25 and about 40 or so nucleotides, but larger contiguous complementarity stretches may be used, such as those from about 200 to about 300, or from about 300 to about 400 or 500 or so nucleotides in length, according to the length complementary sequences one wishes to detect. It is even possible that longer contiguous sequence regions may be utilized including those sequences comprising at least about 600, 700, 800, 900, 1000, 1100, 1200, 1300, 1400, 1500, or more contiguous nucleotides.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one may desire to employ varying conditions of hybridization to achieve varying degrees of selectivity of probe towards target sequence. For applications requiring high selectivity, one will typically desire to employ relatively stringent conditions to form the hybrids. "High stringency" hybridization conditions, e.g., typically employ relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating particular DNA segments. Detection of DNA segments via hybridization is well known to those of skill in the art, and the teachings of U.S. Pat. Nos.

4,965,188 and 5,176,995 (each incorporated herein by reference) are exemplary of the methods of hybridization analyses. Teachings such as those found in the texts of Maloy et al., 1990; Segal, 1976; Prokop and Bajpai, 1991; and Kuby, 1994, are particularly relevant.

Of course, for some applications, for example, where one desires to detect particular target polynucleotide sequences from related species, functional equivalents, or the like, less stringent hybridization conditions will typically be needed in order to allow formation of the heteroduplex between the reporter molecule and the target polynucleotide. In these circumstances, one may desire to employ "low stringency" or "reduced stringency" hybridization conditions such as those employing from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results. Regardless of what particular combination of salts (such as NaCl or sodium citrate and the like), organic buffers (including e.g., formamide and the like), and incubation or washing temperatures are employed, the skilled artisan will readily be able to employ hybridization conditions that are "high," "medium," or "low" stringency, and will be able to interpret the results from hybridization analyses using such conditions to determine the relative homology of a target nucleic acid sequence to that of the particular polynucleotide sequence employed.

In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization within a detection well, and also in embodiments that employ direct or indirect immobilization of the detection probes onto the surface of the biochip or onto a solid phase placed in contact with a biochip. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

Enzymes

In certain embodiments of the invention, the detection of enzymes using the biochip device is contemplated. Such embodiments generally involve the use of labeled bioprobes that specifically bind to such enzymes. Likewise the invention also concerns the use of labeled enzymes as bioprobes for identifying target molecules that specifically bind to the label enzyme. Historically, a major class of enzymes that have been important in existing analytical devices is the oxidoreductases, which catalyze the oxidation of compounds using oxygen or NAD, and the hydrolases, which catalyze the hydrolysis of compounds (Alvarez-Icaza and Bilitewski, 1993). Many biosensors have exploited enzymes as the biological recognition/response system because of the range of transducible components such as protons, ions, heat, light, and electrons, as well as mass that can be exchanged as part of their catalytic mechanism (Lowe, 1989). This catalytic activity is controlled by pH, ionic strength, temperature and the presence of co-factors. Enzyme stability is usually the deciding factor in determining the lifetimes of enzyme based biosensors (typically between 1 day and 1 or 2 months (Rechnitz and Ho, 1990).

Organelles (e.g., mitochondria, chloroplasts) whole cells (e.g., bacteria) or tissue sections from animal or plant sources have been used as biocatalytic packages in biosensors for a large range of metabolites of clinical interest. Together with the numerous enzymes present are all the other necessary components needed to convert substrates into products in an environment that has been optimized by evolution (Scheller et al., 1989; Rechnitz and Ho, 1990). The major drawback of the use of such systems is their multi-enzyme behavior, which results in decreased substrate specificity. However, sometimes such behavior can work to advantage because by merely changing the external experimental conditions different substrates can be measured with the same biocatalytic material. The appropriate use of enzyme inhibitors, activators and stabilizing agents also can be used to enhance the selectivity and lifetimes of tissue based biosensors (Rechnitz and Ho, 1990).

Cell Receptors

In one embodiment, the invention concerns the detection of cells, cell surfaces, and cell receptor polypeptides using the disclosed biosensor devices. In such embodiments, the method generally involves labeling a suitable bioprobe that specifically binds to a particular cell, cell type, cell surface, cell antigen, or cell receptor, and then exposing the biosensor device to a test solution suspected of containing such a cell or cell component.

In a related embodiment, when one desires to detect biomolecules that bind to a given cell, cell type, or cell receptor, the biosensor device can employ a labeled cell or labeled cell receptor polypeptide and use that to detect specific biomolecules that interact with such cell components in a test sample.

Naturally occurring receptors are non-catalytic proteins that span cell membranes, extending into both the extracellular and intracellular spaces. They are involved in the chemical senses, such as olfaction and taste, as well as in metabolic and neural biochemical pathways. Within the organism they act as links in cell-cell communication by reversibly binding specific neuro-transmitters and hormones liberated from other cells for the purpose of conveying messages through the target cell's membrane to initiate or diminish its cellular activity. They are also the binding sites for many drugs and toxins. Two methods have been defined by which binding of a transmitter molecule to the extracellular side of the receptor leads to modification of intracellular processes.

Attempts at using neuroreceptors as the recognition element in biosensors have largely been restricted to the nicotinic acetylcholine receptor (n-AChR) that can be isolated from the electric organ of the electric eel or ray in relatively large quantities. The unavailability of other receptors for biosensor use is no doubt a reflection of the fact that they are normally only present in small amounts in tissues and are unstable once removed from their natural lipid membrane environment. However, the products of receptor DNA expression in foreign cell lines may produce proteins useful for biosensor applications, yet not fully identical to the native starting material (Wingard, 1990). The n-AChR and associated ion channel complex bind several naturally occurring toxins.

Polypeptide Antigens and Antibodies

In other embodiments, the invention concerns the detection of antigens or antibodies in a test sample. In the case of the former, the biosensor device employs one or more labeled antibodies that specifically bind to the target polypeptide antigen. Then the sensor is contacted with a solution suspected of containing the antigen. If the antigen is present in the test sample, an immune complex is formed between the target antigen and the labeled antibody, and the biosensor device may be used to quantitate the amount of antigen present based upon the intensity of the signal produced by the binding of the labeled antibody to the antigen in solution.

In the case of the latter, when it is desirable to identify in a test sample a particular antibody, one may employ a biosensor device that comprises a labeled polypeptide antigen that is specifically recognized by the target antibody. If the antibody is present in the test sample, an immune complex is formed between the target antibody and the labeled antigen, and the biosensor device may be used to quantitate the amount of antibody present based upon the intensity of the signal produced by the binding of the labeled antigen to the antibody in solution.

An antigen is any molecular species that can be recognized by an animal organism as being foreign to itself and which therefore triggers the defensive mechanism known as the immune response. This recognition has a lower molecular weight cut-off of ~10,000 Da (Van Emon and Lopez-Avila, 1992). In natural circumstances such antigens are typically proteins or lipopolysaccharides at the surfaces of viruses, bacteria and microfungi, or at the surfaces of cells and in solution in blood or tissues of other species or even of different individuals of the same species. Foreign DNA or RNA is also antigenic as is material of plant origin.

An antibody (Ab) is a molecule produced by animals in response to the antigen and which binds to the latter specifically. Antibodies to smaller molecular weight environmental contaminants such as pesticides, herbicides, microbial toxins and industrial chemicals can be made after first covalently attaching the latter to a carrier protein such as bovine serum albumin (BSA) or keyhole limpet haemocyanin (KLH) (Van Emon and Lopez-Avila, 1992). The small molecular component of the resultant conjugate, which has been modified for antigenic recognition, is known as a hapten. A host of other biotoxins of microbial, plant and animal origin are either antigenic or can be rendered antigenic by the formation of hapten-protein conjugates.

In mammals, two distinct types of molecule are involved in the recognition of antigens. These are the proteins called immunoglobulins that are present in the serum and tissue fluids, and the antigen receptors on the surface of specialized blood cells-the T-lymphocytes. It is the immunoglobulins, or antibodies, whose selective and tight binding characteristics for antigens are made use of in immunological methods of analysis. In higher animals the immunoglobulins, or antibodies, fall into five distinct classes, namely IgG, IgA, IgM, IgD and IgE. These differ from each other in size, charge, amino acid composition and carbohydrate content. They all appear to be glycoproteins but the carbohydrate content ranges from 2–3% for IgG to 12–14% for the others. The basic structure of all immunoglobulin molecules is a Y-shaped unit consisting of two identical light polypeptide chains and two identical heavy polypeptide chains linked together by disulfide bonds. The amino terminal ends of the 'arms' of the Y are characterized by sequence variability and are the antigen binding sites. IgG is the exclusive anti-toxin class of antibody. IgM is a pentamer of five Y-shaped units whose role appears to be to complex infectious organisms (Turner, 1989).

The binding of antigen to antibody at transducer surfaces can be measured directly and indirectly. Binding can be detected by conjugating the antigen or antibody to a fluorescent label (Anis et al., 1992; Ogert et al., 1992; Lee and Thompson, 1993). The biochip device of the present invention finds particular utility in the detection and quantitation of such polypeptides through the conventions of antigen-antibody interactions that are well known to those of skill in the immunological arts. In one embodiment, the biochip may be configured with one or more antigen probes. As such, the detection of the corresponding antibodies in a sample contacted with the device is then possible. Conversely, when it is desirable for the molecular probe to be an antibody, such probes may be fixed to the solid support of the device and the corresponding epitopes or antigenic peptides or polypeptides that specifically bind to such antibody probe(s) may be detected in a given sample.

Nucleic Acids

The specific sequence of bases along a strand of a DNA, RNA, or PNA and the unique complementary nature of the pairing between the base pairs (e.g., adenine and thymine (or uracil) [A:T or A:U] or cytosine and guanine [C:G]) of adjacent strands in the double helix is the basis of biodiversity. The ability of a single-stranded nucleic-acid molecule to recognize and specifically bind to (or "hybridize" to) its complementary partner in a sample has been used in genetic analyses and may also be used in the biosensor device of the invention.

In an illustrative embodiment, when one desires to detect nucleic acids in a given sample, the sample preparation might include one or more of the following steps: (a) extraction of the nucleic acid from the cells in a sample; (b) preparation of the a nucleic acid (such as DNA) in its single-stranded form; and (c) increasing the total amount of nucleic acid present in the sample by the use of a strand amplification technique such as the polymerase chain reaction (PCR™) (Saiki et al., 1985).

Another possibility is to use DNA binding proteins such as RNA polymerases, promoters, repressors and restriction enzymes, which exhibit the ability to bind to a specific DNA sequence in a double-stranded form to develop a biosensor (Kung et al., 1990; Downs, 1991). Since the preparation of the DNA in single-stranded form and its subsequent hybridization would not be required, such a method involves a shorter sample preparation time.

Detection of Microorganisms

In certain embodiments, the inventor contemplates the use of the biochip device for the detection and/or quantitation of microorganisms, including eukaryotic and prokaryotic organisms in a test sample. Such methods may be employed in the detection of bacteria, fungi, viruses, and the like. This is particularly desirable for the biosensor-based detection of pathogenic strains, species, and genera of these microorganisms. The test sample may be an industrial or production sample being analyzed as part of a quality control or manufacturing process, or alternatively may be a sample of clinical origin, such as a tissue, cell, or blood sample from a patient or animal. Typical pathogens which may be detected by the biochip device includes virtually any unicellular, multicellular, or viral organism for which a specific probe may be affixed to the biochip that is able to bind to the target pathogen or organism. For example, cell surface proteins, including coat proteins, antigens, lipopolysaccharides, and the like, have been identified for hundreds of microorganisms, and as such, provide the skilled artisan with a variety of molecular probes that may be incorporated into the biochip device and used to screen samples for the corresponding molecular target.

Viruses are small cellular parasites that cannot reproduce themselves. They attach to cells via specific receptors and this partly determines which cell types become infected. The particular cells that are infected are ultimately destroyed because of the complex biochemical disturbances accompanying the intracellular replication of the virus. Viruses contain either single-stranded or double-stranded RNA or DNA that is generally surrounded by an outer shell of one or more virus-specific proteins or glycoproteins. In some viruses there is a further external envelope that consists mainly of lipids but also contains some virus-specific proteins. It is the surface coat proteins that are the viral antigens that trigger the immune response and antibody production (Rook, 1989; Darnell et al., 1990). Viruses (and bacteria) have a large number of antigenic determinants on their surfaces and therefore each organism can bind a number of antibody units. This results in a considerable increase in stability of virus-antibody complexes over hapten-antibody complexes (up to $10^3$–$10^4$-fold depending on the antibody) (Darnell et al., 1990).

TABLE 1

EXEMPLARY PATHOGENIC ORGANISMS DETECTABLE USING THE AMB DEVICE

| Viruses | Bacteria | Fungi |
|---|---|---|
| Variola virus; reoviruses; poxvirus; lentivirus; | Rickettsia (including R. prowazecki) | Coccidioides immitis |
| Chikungunya virus; parovirus, paromyxovirus; | R. tsutsugamushi and R. rickettsia | Histoplasma capsulatum |
| Influenza viruses; | Klebsiella, Haemophilus, and Morganella spp. | Norcardia asteroides |
| Encephalitis viruses, including Western, Eastern; Russian, Spring-Summer, Japanese and Venezuelan; | Bacillus spp. (including B. anthracis) | Candida spp. |
| Calicivirus; rhinovirus; | Francisella (Pasteurella tularensis) | Microsporum gypsum |
| Dengue virus; | Pasteurella pestis | Epidermatophyton floccosum |
| Yellow fever virus; | Brucella spp. (including B. melitensis and B. suis) | |
| Herpes virus; Encephalitis virus; Rift Valley fever virus; | Coxiella burnetti Salmonella spp. (including S. typhimurium and S. paratyphi) | |
| Lassa fever virus; | Vibrio spp. (including V. cholera and V. comma) | |
| Lymphocyte choriomeningitis virus; Hemorrhagic fever viruses, including Argentine, Bolivian, Korean, and Crimean-Congo types; | Corynebacterium diphtheria Actinobacillus mallei | |
| Hantaviruses; | Pseudomonas (including P. psyringae, P. cepacia, and P. pseudomallei) | |
| Ebolavirus; | Mycobacterium tuberculosis | |
| HIV and related retroviruses | Escherichia coli | |
| Marburg virus | Shigella, and Corynebacterium spp. | |
| Hepatitis A virus | Listeria spp. (including L. monocytogenes) Legionella (including L. pneumophila) | |

Certain pathogenic bacteria synthesize and secrete exotoxins as part of the mechanism underlying the specific symptoms of the diseases that they produce. Examples of these proteins that poison or kill susceptible mammalian cells are the *Shigella dysenteria* toxin. *Staphylococcus aureus* enterotoxin, tetanus toxin and *botulinum* neurotoxin, as well as the toxins produced by *Bacillus anthracis* and *Corynebacterium diphtheriae*. Other pathogenic bacteria (including the species in Table 1) liberate toxins when they are lysed. These toxins, also known as endotoxins, are components of the bacterial cell wall and are conjugates of protein, lipid and carbohydrate. Both types of toxin are antigenic. The different types of bacteria have different cell wall structures. All types (Gram-positive (G+), gram-negative (G−) and mycobacteria) have an inner cell membrane and a peptidoglycan wall. Gram-negative bacteria also have an outer lipid bilayer in which lipopolysaccharide is sometimes found. The outer surface of the bacterium may also contain fimbriae or flagellae, or be covered by a protective capsule. Proteins and polysaccharides in these structures can act as targets for the antibody response.

Some fungi are pathogenic to man because they can invade the body tissues and proliferate there rather than because they liberate toxins. Three of these are listed in Table 1. Other fungi are dangerous to humans because of the toxins they produce and liberate into the environment A particular example of the latter is the fusarium species that produce tricothecene mycotoxins mentioned.

The inventor contemplates that in addition to bacterial species, other microorganisms may also be detected using the disclosed biosensors. For example, yeast strains may be constructed by methods similar to those disclosed herein for bacterial strains in which the yeast will emit a bioluminescent signal in response to an environmental signal or stress.

Biosensors Based on Antibodies

There is a wide range of toxins for which enzyme based and receptor based strategies are not available for the development of biosensors. However, assuming that one can obtain the appropriate antibodies, antibody based biosensors are possible for several of toxic chemicals and probably all toxins and pathogenic microorganisms listed in Table 1.

One of the continuing challenges in the development of immunosensors is to be able to immobilize the antibodies at high density on the appropriate surface whilst still maintaining their functional configuration and preventing stearic hindrance of the binding sites. This has led to the use of self-assembling long chain alkyl membrane systems (SAMSs) on glass or silica and gold surfaces. The terminal functional groups on each chain are designed to react with specific groups on antibodies or antibody fractions to form a uniform geometrical array of antigen binding sites (Bhatia et al., 1989; Zull et al., 1994; Mrksich and Whitesides, 1995).

The stability of the immobilized antibodies is also a critical factor for future immunosensor research. A problem associated with this is that if on-site preparation of the system for the capture process is required, this may take several h and methods need to be developed to speed this up. A further requirement, which is more important for immobilization on piezoelectric devices, is the need to reduce non-specific protein binding to the sensor surface (Ahluwalia et al., 1991). Perhaps one approach to this problem would be to use a SAM formed from a mixture of two long chain alkane thiolates, one with a terminal functional group for reaction with, for example, Fab-SH fragments and the other presenting a short oligomer of ethylene glycol to resist the non-specific adsorption of protein at the membrane surface (Zull et al., 1994; Mrksich and Whitesides, 1995). This mixture would allow the possibility of controlling the spacing of the covalently bound antibody fraction and optimizing specific antigen binding.

Most immunological reactions are essentially irreversible because of their large association constants ($K_a$s of $10^5$–$10^9$ $M^{-1}$). The $K_aS$ are composed of large forward [$k_1$] and small reverse [$k_1$] rate constants ranging from $10^7$ to $10^9$ $M^{-1}$ $s^{-1}$ and $10^2$ to $10^{-4}$ $s^{-1}$, respectively (Barnard and Walt, 1992). Developing antibodies with sufficiently fast antigen dissociation rates to allow reversible measurements in real time (North, 1985; Roe, 1992) could lead to continuous or at least sequential measurements of the antigen without the need to replace the antibody or reverse the binding by the use of chaotropic solutions (Blanchard et al., 1990; Wijesuriya et al., 1994). Recombinant technology will eventually allow the production of antibodies with new binding properties.

An approach that may solve the problem of irreversibility is the development of catalytic antibodies (Lerner et al., 1991; Haynes et al., 1994). Haptens designed to mimic the stercoelectronic features of transition states can induce antibodies capable of catalyzing a wide range of chemical transformations, ranging from simple hydrolyses of esters and amides to reactions that lack physiological counterparts or are normally disfavored (Lerner et al., 1991; Haynes et al., 1994). A potentiometric biosensor employing catalytic antibodies as the molecular recognition element has been described by Blackburn et al. (1990). Thus, it is conceivable that if catalytic antibodies can be obtained for toxic chemicals and toxins, then biosensors for these substances, capable of continuous unattended running and not requiring fresh supplies of sensor material, could become a reality.

Alternatively, to utilize immunoreactions effectively in sensor design, the problem of irreversibility may be circumvented by creating a reservoir that passively releases immunoreagents to the sensing region of the particular device. Controlled release polymers have been used for this purpose (Barnard and Walt, 1992).

Recently, Wallace and co-workers (see Sadik et al., 1994) have suggested that because the Ag-Ab interaction is a multi-step process (involving a variety of different molecular interactions according to the distance apart), it is possible that specificity is locked in at the early stages and irreversibility occurs at the later stages, accompanied by conformational changes. Wallace et al. have presented evidence of this specificity from pulsed amperometric measurements using a platinum electrode coated in a film of polypyrrole containing the antibody to thaumatin. During continuous pulsing of the applied potential in the presence of the antigen, rapid and reversible peaks of current were observed whose height was directly proportional to the antigen concentration. Injections of BSA and other proteins gave very much reduced responses but it is not clear how much of this was due to the difference in charge structure.

Nucleic-acid Based Biosensors

The time-consuming preparative steps in gene probe assays make it difficult for them to be considered as the basis of biosensors for the on-site detection of pathogenic microorganisms. The major time-consuming steps are the DNA isolation and amplification (PCR™) procedures and the hybridization detection step. Recently, it has been possible to grow ss-DNA on the surface of optical fibers and to detect the hybridization process with complementary ss-DNA in a sample by using the fluorescence of ethidium bromide trapped in the double-stranded regions of the bound DNA (Piunno et al., 1994). Besides, the possibility of being very sensitive and selective, such a nucleic acid-based biosensor has some advantages over antibody-based biosensors. First, it is more stable and can be stored for longer periods. Also, the probe can be repeatedly regenerated for further use by a short immersion in hot buffer. By the development of appropriate polynucleotide and polypeptide probes for the detection of microorganisms such as bacteria and fungi (Smith et al., 1994), a variety of improved methods have been developed to overcome limitations of existing procedures. Detection of hybridization has been further improved by covalently immobilizing dsDNA sensitive fluorescent dye directly onto immobilized ssDNA at the glass fiber surface (Piunno et al., 1994).

Methods for Preparing Antibodies

In another aspect, the present invention contemplates an antibody that is immunoreactive with a polypeptide. Reference to antibodies throughout the specification includes whole polyclonal and monoclonal antibodies (mAbs), and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. In a preferred embodiment, an antibody is a polyclonal antibody.

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for given polypeptides may be prepared using conventional immunization techniques, as will be generally known to those of skill in the art. A composition containing antigenic epitopes of particular polypeptides can be used to immunize one or more experimental animals, such as a rabbit or mouse, which will then proceed to produce specific antibodies against the polypeptide. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored or the animal can be used to generate mAbs (below), or both.

One of the important features provided by the present invention is a polyclonal serum that is relatively homogenous with respect to the specificity of the antibodies therein. Typically, a polyclonal antiserum is derived from a variety of different "clones," i.e. B-cells of different lineage. mAbs, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, antisera that do not react or react poorly with the native molecule.

To obtain mAbs, one would also initially immunize an experimental animal, often preferably a mouse, with a polypeptide-containing composition. After a period of time sufficient to allow antibody generation, one would obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones that can then be screened for production of antibody to the desired polypeptide.

Following immunization, spleen cells are removed and fused, using a standard fusion protocol with plasmacytoma cells to produce hybridomas secreting mAbs against a polypeptide of interest. Hybridomas that produce mAbs to the selected antigens are identified using standard techniques, such as ELISA and Western blot methods. Hybridoma clones can then be cultured in liquid media and the culture supernatants purified to provide the polypeptide of interest-specific mAbs.

Of particular utility to the present invention are antibodies tagged with a fluorescent or enzymatic molecule. Methods of tagging antibodies are well known to those of skill in the art and a large number of such antibodies are available commercially. Fluorescent tags include, but are not limited to, fluorescein, phycoerythrin, and Texas red. Enzymatic tags, include, but are not limited to, alkaline phosphatase and horseradish peroxidase.

Nucleic-acid Segments

The present invention also concerns the detection and/or quantitation of polynucleotides that can be isolated from virtually any source, including clinical samples and specimens. Such nucleic-acid segments may be naturally occurring polynucleotides, or synthesized entirely or partially in vitro using methods that are well known to those of skill in the art. Such segments may comprise genes, promoters, enhancers, or other functional elements of a nucleic acid, and may be isolatable from genomic or non-genomic sources, including chromosomes, artificial chromosomes, vectors (including phage, cosmids, plasmids, viral vectors, and the like).

Similarly, a nucleic-acid segment comprising an isolated or purified gene refers to a nucleic-acid segment or selected sequence region which may include, in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those skilled in the art, this functional term includes both genomic sequences, cDNA sequences and smaller engineered gene segments that express, or may be adapted to express proteins, polypeptides or peptides.

"Isolated substantially away from other coding sequences" means that the gene, or operon, of interest, in this case, an operon encoding a desired polypeptide, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

It will also be understood that amino acid and nucleic-acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic-acid sequences that may, for example, include various non-coding sequences flanking either of the 5' or 3' portions of the coding region or may include various internal sequences, i.e., introns, which are known to occur within genes.

The nucleic-acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic-acid fragment of almost any length may be employed, with the total length preferably being limited by the ease of preparation and use in the intended recombinant DNA protocol.

The use of and synthesis of various polynucleotide probes or primers designed to specifically hybridize to a particular nucleotide sequence of interest may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12, and so on. For a 15-mer, the probes correspond to bases 1 to 15, 2 to 16, 3 to 17, and so on. For a 20-mer, the probes correspond to bases 1 to 20, 2 to 21, 3 to 22, and so on.

It will also be understood that this invention is not limited to the particular nucleic-acid sequences that encode peptides of the present invention. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments to be detected by the devices of the present invention may also encompass biologically functional equivalent peptides. Such sequences may arise as a consequence of codon redundancy and functional equivalency that are known to occur naturally within nucleic-acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by humans may be introduced through the application of site-directed mutagenesis techniques, e.g., to introduce improvements to the particular probe or target to be tested, or to create or identify mutant, second-generation, or homologous sequences.

If desired, one may also prepare probes to detect fusion proteins or smaller peptides, e.g., where the peptide-coding regions are aligned within the same expression unit with other proteins or peptides having desired functions, such as plastid targeting signals or "tags" for purification or immunodetection purposes (e.g., proteins that may be purified by affinity chromatography and enzyme label coding regions, respectively).

Polynucleotide sequences comprised within recombinant vectors form further targets for detection using the devices of the present invention. Particularly well-known vectors are those vectors in which the coding portion of a given DNA segment, whether encoding a full-length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning or PCR™ technology, or both in connection with the compositions disclosed herein.

The ability of such nucleic-acid probes to specifically hybridize to a target polypeptide-encoding sequence enables them to be of use in detecting the presence of complementary sequences in a given sample. However, other uses are envisioned, including the use of the sequence information for the preparation of mutant species primers, or primers for use in preparing other genetic constructions. Such sequences may be detected through the use of a suitable labeled substrate (either a labeled probe, or a labeled target, or labels on both the probe and the target). Alternatively, a substrate may be detected through the use of a secondary label. For example, the detection of hybridizing polynucleotides may be accomplished by the addition of a suitable intercalating agent or other dye that fluoresces only in the presence of a duplex polynucleotide (e.g., the duplex formed by the hybridization of an unlabeled probe with an unlabeled target nucleic acid). One such dye that has widespread use in the detection of double-stranded nucleic acids is ethidium bromide.

The use of a hybridization probe of about 14, 15, 16, 17, 18, or 19 nucleotides in length allows the formation of a duplex molecule that is both stable and selective. In order to increase stability and selectivity of the hybrid molecules having contiguous complementary sequences over stretches greater than 14, 15, 16, 17, 18, or 19 bases in length are generally preferred and thereby improve the quality and degree of specific hybrid molecules obtained; however, one will generally prefer to design nucleic-acid molecules having gene-complementary stretches of 15 to 20 contiguous nucleotides, or even longer, where desired.

Of course, fragments may also be obtained by other techniques such as, e.g., by mechanical shearing or by restriction enzyme digestion. Small nucleic-acid segments or fragments may be readily prepared by, for example, directly synthesizing the fragment by chemical means, as is commonly practiced using an automated oligonucleotide synthesizer. Also, fragments may be obtained by application of nucleic-acid reproduction technology, such as the PCR™ technology of U.S. Pat. Nos. 4,683,195 and 4,683,202, each incorporated herein by reference, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one may desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt, or high temperature conditions, such as provided by about 0.02 M to about 0.15 M NaCl at temperatures of about 50° C. to about 70° C., or both. Such selective conditions tolerate little, if any, mismatch between the probe and the template or target strand, and would be particularly suitable for isolating particular polypeptide-encoding DNA segments. Detection of DNA segments via hybridization is well known to those of skill in the art, and the teachings of U.S. Pat. Nos. 4,965,188 and 5,176,995, each incorporated herein by reference, are exemplary of the methods of hybridization analyses. Teachings such as those found in the texts of Maloy et al., 1990; 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate or identify particular polypeptide-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature does. Thus, hybridization conditions can be readily manipulated, and thus will generally be a method of choice depending on the desired results.

In certain embodiments, it will be advantageous to employ nucleic-acid sequences of the present invention in combination with an appropriate means, such as a label, for determining hybridization. A wide variety of appropriate indicator means are known in the art, including fluorescent and enzymatic, which are capable of giving a detectable signal. In preferred embodiments, one will likely desire to employ a fluorescent label or an enzyme tag, such as urease, alkaline phosphatase or peroxidase. In the case of enzyme tags, colorimetric indicator substrates are known that can be employed to provide a means visible to the human eye or spectrophotometrically to identify specific hybridization with complementary nucleic-acid-containing samples. Similarly, in the case of fluorescent tags, fluorescent indicators are known that can be employed to provide a means visible to the apparatus of the present invention.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic-acid, source of nucleic-acid, size of hybridization probe, eta). After washing of the hybridized surface so as to remove nonspecifically bound probe molecules, specific hybridization is detected, or even quantitated, by means of the label. Means for probe labeling and hybrid detection of polynucleotides are well-known to those of skill in the art, as evidenced by references such as Sayler and Layton (1990) and Hill et al. (1991), each specifically incorporated herein by reference.

Methods for Preparing and Detecting Mutagenized Polynucleotides

In certain circumstances, it may be desirable to modify or alter one or more nucleotides in one or more of the particular probe or target polynucleotide sequences for the purpose of altering or changing the homology, or degree of similarity between a selected target and one or more probes. In general, the means and methods for mutagenizing a nucleic acid segment are well known to those of skill in the art. Modifications to such segments may be made by random or site-specific mutagenesis procedures. The promoter region may be modified by altering its structure through the addition or deletion of one or more nucleotides from the sequence that encodes the corresponding un-modified promoter region.

Mutagenesis may be performed in accordance with any of the techniques known in the art such as and not limited to synthesizing an oligonucleotide having one or more mutations within the sequence of a particular promoter region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector that exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired promoter region or peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting, as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide directed mutagenesis procedure" refers to template-dependent processes and vector-mediated propagation that result in an increase in the concentration of a specific nucleic-acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic-acid synthesis of an RNA or a DNA molecule wherein the sequence of the newly synthesized strand of nucleic acid is dictated by the well known rules of complementary base pairing (Watson, 1987). Typically, vector mediated methodologies involve the introduction of the nucleic-acid fragment into a DNA or RNA vector, the clonal amplification of the vector, and the recovery of the amplified nucleic-acid fragment. Examples of such methodologies are provided by U.S. Pat. No. 4,237,224, specifically incorporated herein by reference in its entirety.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

DNA Biochips for Polynucleotide Detection

Rapid, simple, cost-effective medical devices for screening multiple medical diseases and infectious pathogens are essential for early diagnosis and improved treatments of many illnesses. An important factor in medical diagnostics is rapid, selective, and sensitive detection of biochemical substances (proteins, metabolites, nucleic acids), biological species or living systems (bacteria, virus or related components) at ultratrace levels in biological samples (e.g., tissues, blood and other bodily fluids). To achieve the required level of sensitivity and specificity in detection, it is often necessary to use a biosensor that is capable of identifying and differentiating a large number of biochemical constituents in complex samples. Living systems possess exquisite recognition elements (e.g., antibody, enzyme, gene probes, etc.), often referred to as bioreceptors, which allow specific identification and detection of complex chemical and biological species. Biosensors exploit this powerful molecular recognition capability of bioreceptors. Due to the exquisite specificity of the DNA hybridization process, there is an increasing interest in the development of DNA bioreceptor-based analytical systems (Vo-Dinh et al., 1994; Isola et al., 1996; Alarie et al., 1992; Vo-Dinh et al., 1987a; 1987b; VoDinh et al., 1991; Stevenson et al., 1994). Gene probes using a novel detection scheme based on surface-enhanced Raman scattering (SERS) labels were recently developed in the inventor's laboratory to enhance both the selectivity and sensitivity of DNA biosensors (Vo-Dinh et al., 1994). A fluorescence-based fiber optic genosensor for *Mycobacterium tuberculosis* was reported (Isola et al., 1996).

This work involves the development of a new generation of biosensors based on integrated circuit (IC) microchips using DNA bioreceptors designed to detect sequence-specific genetic constituents in complex samples. The design of the integrated electro-optic system on IC microchips, photodetector elements with amplifier circuitry, and their integration and use in DNA biosensor applications are discussed. The use of IC technology could lead to the development of extremely low-cost diagnostic biochips for medical applications. Measurements using the HIV1 sequence-specific probes on the biochip device illustrate the application of the DNA biochip to the detection of a gene segment of the AIDS virus.

Integrated Circuit of the Photodiode Array Microchip

The biochip investigated in this example includes a large-area, 4×4 n-well integrated amplifier-photodiode array that has been designed as a single, custom integrated circuit (IC), fabricated for the biochip. This IC device is coupled to the multiarray sampling platform and is designed for monitoring very low light levels. The individual photodiodes have 900-$\mu$m square size and are arrayed on a 1-mm spacing grid. The photodiodes and the accompanying electronic circuitry were fabricated using a standard 1.2-micron n-well CMOS process. The use of this type of standard process allows the production of photodiodes and phototransistors as well as other numerous types of analog and digital circuitry in a single IC chip. The photodiodes themselves are produced using the n-well structure that is generally used to make resistors or as the body material for transistors. Since the anode of the diode is the p-type substrate material, which is common to every circuit on the IC chip, only the cathode is available for monitoring the photocurrent and the photodiode is constrained to operate with a reverse bias.

An analog multiplexer is designed to allow any of the elements in the array to be connected to an amplifier. In the final device, each photodiode could be supplied with its own amplifier. The multiplexer is made from 16 cells. Each cell has two CMOS switches that are controlled by the output of the address decoder cell. Each cell has a unique 4-bit address. One switch is open only when it is being addressed while the other switches are closed. This process connects the addressed diode to one amplifier while all the others are connected in parallel to the other amplifier.

This arrangement allows connecting a 4×4 array of light sources (different fluorescent probes, for example) to the photodiode array and reading out the signal levels sequentially. With some modification, a parallel reading system can be designed. Using a single photodiode detector would require mechanical motion to scan the source array. The additional switches and amplifier serve to correctly bias and capture the charge generated by the other photodiodes. The additional amplifier and switches allow the IC to be used as a single, large area (nearly 4 mm square) photodetector.

Application of the Biochip to HIV Gene Fragment Detection

The inventor performed measurements using the biochip device with 4×4-photodiode array for detection of the HIV1 gene. The signals from the photodiode microchip were directly recorded without the need of any electronic interface system or signal amplification device. The photocurrent of each sensing of the microchip was transmitted directly into a digital photometer or a strip chart recorder. The data from the photometer were linked to a personal computer (PC) via an RS-232 link. The sampling platform of the biochip contained a 4×4 array of microspots of NIR-labeled DNA on a nitrocellulose membrane.

The HIV1 gene probe is the 1 8-base oligonucleotide sequence complementary to the gag gene region. For this study, the inventor bound cDNA of specific sequences of the HIV1 virus onto the nitrocellulose membrane and hybridized them with CyS dye-labeled DNA strands having complementary sequences. The HIV1 measurements on the nitrocellulose was performed by spotting the HIV1 probe DNA in a 4×4 array onto the nitrocellulose sampling platform. The DNA was then crosslinked to the nitrocellulose using either a UV crosslinker or baked in vacuum at 80 degrees C. for two h. With nitrocellulose membranes, the DNA solutions were spotted directly onto the membranes. The spots were subsequently subjected to either UV crosslinking using a Stratalinker (Stratagene, La Jolla, Calif.) or were baked in vacuum at 80° C. for two h. The first step in membrane hybridization involved immobilization of single-stranded target nucleic acids to the selected surface of the probe. The probes were then treated with hybridization buffer to block nonspecific nucleic acid binding sites. The probe was introduced to samples containing labeled probe DNA and allowed to hybridize by reestablishing a double-stranded molecule with the complementary target sequences. After hybridization, excess unbound labeled probe was washed off, and the hybrid target sequences detected. In this work, the nitrocellulose membranes were prehybridized for one h at 37° C. in 5 mL of 6×SSC (1×SSC=15 mM Sodium citrate, 150 mM sodium chloride pH 7.0) containing 1% BSA, 0.2% SDS (sodium dodecyl sulfate). After pre-hybridization, the hybridization probe was added to a final concentration of 100 ng/ml and hybridizations performed. After hybridization the membranes were washed in 5×SSC containing 0.1% SDS at room temperature for 10–15 min to reduce the background fluorescence levels.

Hybridization occurs between complementary DNA sequences was demonstrated by the fluorescence signals detected by the biochip. Only fluorescence signals were detected on the biochip channels where hybridization of labeled DNA HIV1 gene probes with complementary bound-DNA fragments had occurred. The 4×4 array signals of the 3-dimensional plot demonstrated positive hybridization with the HIV1 probes used in this study. A reference system of negative blank samples (consisting of DNA probes which did not have the sequence of the HIV1 gene) did not show fluorescent signals. This result illustrates the usefulness of the DNA biochip for detection of the HIV gene probe.

Preparation of Oligonucleotides

The inventor synthesized desired strands of oligonucleotides and labeled them with fluorescent labels (e.g., fluorescein and Cy5 dyes) using procedures previously described (Vo-Dinh et al., 1994; Isola et al., 1998). All oligonucleotides were synthesized using an Expedite 8909 DNA synthesizer (Millipore, Bedford, Mass.). Fluorescein-labeled oligonucleotides were prepared with fluorescein CPG columns (for 3' labeling) or fluorescein phosphoramidite (for 5' labeling) using modified synthesis protocols as recommended by the manufacturers. Oligonucleotides with amino linkers were synthesized using either C3 aminolink CPG for 3' labeling or 5' amino modifier C6 (Glenn Research, Sterling, Va.) for Y labeling. All oligonucleotides were synthesized using Expedite reagents (Millipore) and were deprotected and cleaved from the glass supports using ammonium hydroxide. The deprotected oligonucleotides were concentrated by evaporating the ammonium hydroxide in a Speedvac evaporator (Savant Instruments, Farmingdale, N.Y.) and resuspended in 100 1 $\mu$l distilled $H_2O$. Further purification was performed by isopropanol precipitation of the DNA as follows: 10 $\mu$l of 3 M sodium acetate pH 7.0 and 110 $\mu$l isopropanol was added to 100 $\mu$l solution of DNA. The solution was then frozen at −70° C. Sodium acetate was used instead of ammonium acetate since the residual ammonium ions interfere with Cy5 linkage as well as with binding of DNA to solid supports through the amino linkers. The precipitate was collected by centrifugation at room temperature for 15 min and was washed three times with 50% isopropanol. Residual isopropanol was removed by vacuum drying in the Speedvac™ and the DNA resuspended in sterile distilled water at a final concentration of 10 $\mu g\,\mu l^{-1}$. These stock solutions were diluted in the appropriate buffer at a 1:10 dilution to give a DNA concentration of 1 $\mu g\,\mu l^{-1}$.

For labeling DNA with Cy5 dye (Amersham Life Sciences, Arlington Heights, Ill.), modified oligonucleotides containing alkyl amino groups were derivatized as follows (Vo-Dinh et al., 1994) 30 pmol of the DNA was dissolved in 250 $\mu$l 0.5 M sodium chloride and passed through a Sephadex G10 (1 cm diameter, 10 cm long) (Pharmacia, Piscataway, N.J.) column equilibrated with 5 mM borate buffer (pH 8.0). The void volume containing the oligonucleotide was collected and concentrated by evaporation. This was dissolved in 100 $\mu$l 0.1 M carbonate buffer (pH 9.0). Cy5 (1 mg in carbonate buffer) was added to the oligonucleotide and the conjugation reaction was performed at room temperature for 60 min with occasional mixing. The conjugated oligonucleotide was separated from the free dye using a Sephadex G10 column as described above. The fractions containing the labeled DNA were collected and concentrated using a Speedvac evaporator.

Results

Biochip Integrated Circuits

An important element in the development of the biochip involves the design and development of an IC electro-optic system for the microchip detection elements using the CMOS technology. With this technology, highly integrated biosensors are made possible partly through the capability of fabricating multiple optical sensing elements and microelectronics on a single IC. A two-dimensional array of optical detector amplifiers was integrated on a single IC chip. Such an integrated microchip system is not currently available commercially.

Two exemplary biochip IC systems based on photodiode circuitry were constructed, one system having 16 channels (4×4 array), and the other having 100 channels (10×10 array). The biochips include a large-area, n-well integrated amplifier-photodiode array that has been designed as a single, custom integrated circuit (IC), fabricated for the biochip. This IC device is coupled to the multiarray sampling platform and is designed for monitoring very low light levels. The individual photodiodes have 900 $\mu$m square size and are arrayed on a 1 mm spacing grid. The photodiodes and the accompanying electronic circuitry were fabricated using a standard 1.2$\mu$n-well CMOS process. The use of this type of standard process allows the production of photodiodes and phototransistors as well as other numerous types of analog and digital circuitry in a single IC chip. This feature is the main advantage of the CMOS technology in comparison to other detector technologies such as charge-coupled devices or charge-injection devices. The photodiodes themselves are produced using the n-well structure that is generally used to make resistors or as the body material for transistors. Since the anode of the diode is the p-type substrate material, which is common to every circuit on the IC chip, only the cathode is available for monitoring the photocurrent and the photodiode is constrained to operate with a reverse bias.

An analog multiplexer was designed that allows any of the elements in the array to be connected to an amplifier. In the final device, each photodiode could be supplied with its own amplifier. The multiplexer is made from 16 cells for the 4×4 array device. Each cell has two CMOS switches that are controlled by the output of the address decoder cell. Each cell has a unique 4-bit address. One switch is open only when it is being addressed while the other switches are closed. This process connects the addressed diode to one amplifier while all the others are connected in parallel to the other amplifier.

This arrangement allows connecting a 4×4 (or 10×10) array of light sources (different fluorescent probes, for example) to the photodiode array and reading out the signal levels sequentially. With some modification, a parallel reading system can be designed. Using a single photodiode detector would require mechanical motion to scan the source array. The additional switches and amplifier serve to correctly bias and capture the charge generated by the other photodiodes. The additional amplifier and switches allow the IC to be used as a single, large area (nearly 4 mm square) photodetector.

Illustrative Applications Involving Biochip Devices

The human immunodeficiency virus (HIV) gag gene sequence was selected as a model template to evaluate the biochip sensing system. Infection with the human immunodeficiency virus Type 1 (HIV1) results in a uniformly fatal disease. Unfortunately standard HIV serologic tests, including the enzyme-linked immunosorbent assay and the Western blot assay, are not useful in the diagnosis of HIV infection during early infancy because of the confounding presence of trazsplacentally derived maternal antibody in the infants blood. There is a need for a direct nucleic acid based test that detects the presence of HIV viral sequences. The inventor utilized synthetic DNA templates (Isola et al., 1998) from the gag gene region of HIV1 as a model system to illustrate the application of the biochip system for HIV gene detection.

The biochip device with 4×4-photodiode array was evaluated for the detection of HIV1 gene fragments. The signals from the photodiode microchip were directly recorded without the need of any electronic interface system or signal amplification device. The photocurrent of each sensing of the microchip was transmitted directly into a digital photometer or a strip chart recorder. The data from the photometer were linked to a personal computer (PC) via an RS-232 link. The sampling platform of the biochip contained a 4×4 array of microspots of NIR-labeled DNA on a nitrocellulose membrane.

To illustrate the usefulness of the biochip in hybridization applications, an 18-base oligonucleotide sequence complementary to the gag gene was used region-of the HIV1 gene (Isola et al., 1998). The inventor used various probe sequences selected in this region to design DNA probes for hybridization and detection using a novel technique based on surface-enhanced Raman scattering (Isola et al., 1998). For this study, the inventor bound cDNA of specific sequences of the HIV1 virus onto the nitrocellulose membrane used as the sampling platform, and hybridized them with Cy5 dye-labeled DNA strands having complementary sequences. The HIV1 measurements on the nitrocellulose was performed by binding the HIV1 probe DNA in a 4×4 array onto the nitrocellulose sampling platform. The DNA was then crosslinked to the nitrocellulose using either a UV crosslinker or baked in vacuum at 80° C. for 2 h. The spots were subsequently subjected to either UV crosslinking using a Stratalinker (Stratagene, La Jolla, Calif.) or were baked in vacuum at 80° C. for 2 h. The first step in membrane hybridization involved immobilization of single-stranded target nucleic acids to the selected surface of the probe. The probes were then treated with hybridization buffer to block nonspecific nucleic acid binding sites. The probe was introduced to samples containing labeled probe DNA and allowed to hybridize by reestablishing a double-stranded molecule with the complementary target sequences. After hybridization, excess unbound labeled probe was washed off, and the hybrid target sequences detected. In this work, the nitrocellulose membranes were prehybridized for 1 h at 37° C. in 5 ml of 6×SSC (1×SSC=15 mM sodium titrate, 150 mM sodium chloride pH 7.0) containing 1% BSA, 0.2% SDS (sodium dodecyl sulfate). After pre-hybridization, the hybridization probe was added to a final concentration of 100 ng ml$^{-1}$ and hybridizations performed. Following hybridization under appropriate conditions, the membranes were washed in 5×SSC containing 0.1% SDS at room temperature for 10–15 min to reduce the background fluorescence levels.

Hybridization occurs between complementary DNA sequences was demonstrated by the fluorescence signals detected by the biochip. Data showed that fluorescence signals higher than the background were detected on the biochip channels where hybridization of labeled DNA HIV1 gene probes with complementary bound-DNA fragments had occurred. The 4×4 array signals of the 3-dimensional plot demonstrated positive hybridization with the HIV1 probes used in this study. A reference system of negative blank samples (consisting of DNA probes which did not have the sequence of the HIV1 gene) showed only weak background fluorescent signals. This result is an illustration the usefulness of the DNA biochip for detection of a specific HIV gene sequence. Detection of the HIV virus itself may also require simultaneous detection of multiple gene sequence regions of the virus. It has been observed that progression of the AIDS disease causes increase in the genotype diversity in HIV viruses. It has been reported that the HIV viruses appear to defeat the immune system by producing and accumulating these gene mutations as the disease progresses (Wolinsky et al., 1996). In addition to the exemplary sequences used in this example, other sequence fragments of the HIV viruses could be used to detect particular genes or regions of the HIV genome.

Likewise, the polynucleotide probes used for hybridization applications of the biochip apparatus need not be necessarily DNA probes, nor do the particular polynucleotide targets to be detected need necessarily be DNA molecules. Because DNA:DNA, DNA:RNA, DNA:PNA, RNA:RNA, RNA:PNA, and PNA:PNA duplexes and DNA:DNA:DNA, DNA:RNA:DNA, RNA:DNA:RNA, RNA:RNA:RNA, DNA:RNA:PNA, RNA:PNA:DNA, etc. triplexes may be formed under the appropriate hybridization conditions and depending upon the degree of homology of the two (or in the case of triplexes, three) strands, the inventor contemplates that a variety of hybridization biochips may be designed which will utilize either RNAs, DNAs, or PNAs in the detection of other homologous polynucleotide molecules. The preparation, synthesis, and use of ribozyrnes, RNAs, and PNAs as polynucleotide probes are described herein in Section 4.

As discussed, it is not necessary that the bioprobes are limited only to polynucleotides or polypeptides. Clearly there are numerous additional probes that could be considered for immobilization on the disclosed biochip. For example, Erdeniz et al. (1997) report cloning-free PCR™ based allele replacement methods. Allele transfer between yeast strains is described in which the desired allele is amplified by PCR™ with a pair of adaptamers. Adaptamers are chimeric oligonucleotides that used to amplify the selected allele and differentially tag its 5' and 3' ends. Such adaptamers depending upon the desired amplification could be attached to the biochip and employed to track the amplification reaction.

Molecular imprinting is a technique used for creating selective recognition sites in synthetic polymers. A template molecule used in polymerization reactions of selected monomers. Many polymers obtained by this method show stereo and regio-specific selectivity, thus, enabling chiral separation of bioactive molecules, Mosbach (1994). It is contemplated that selected imprinted polymers could be designed to include one or more detectable labels that optionally may change their emission signal upon binding of a cognate molecule.

Cyclodextrins are well known for their utility in delivery of certain drugs particularly peptide and protein drugs. The cyclodextrins are also known for their ability to incorporate numerous types of compounds as guest molecules. Modified cyclodextrins such as those obtained by polymerization of ethylene oxide around a core of cyclodextrin have been employed as drug delivery systems. Polyethylene oxide modified cyclodextrins have been described by Topchieva et al (1998) as a new family of bouquet-like molecules with properties similar to the course cyclodextrins. Appropriately tagged cyclodextrins or modified cyclodextrins are also contemplated as having utility as bioprobes useful in connection with the disclosed biochip.

Lipiphilic polyamide dendrimers comprise another class of symmetrical macromolecules that are though to be potential drug carriers, Sakthivel et al. (1998). Because of their lipophilic properties, they have been investigated as gene transfer agents. Qin et al. (1998) have reported the use of Starburst dendrimers to increase plasmid-mediated gene transfer and efficiency. Polyamidoamine subunits assembled into Starburst dendrimers were used to augment plasmid-mediated gene transfer. Starburst dendrimers therefore may be useful in monitoring efficiency of gene transfer in vivo monitoring prolongation of allograft survival or other events in vivo where the detection of labeled tracers in biological fluids might be desirable. In addition to Starburst dendrimers, radio labeled dendrimers have been described which are macromolecular T2 contrast agents. Tagged dendrimers could be detected by choosing the appropriate bioprobe on the chip to pick up these agents and presence detected by measuring radioactivity. Bulte et al (1998) have described Dysprosium-DOTA-PAMAM dendrimers that illustrate a particular example of AT2 contrast agent. Additional probes include biotinylated Starburst dendrimers might be used in antibody pre-targeting as described by Wilbur et al. (1998).

Moreover, in addition to the illustrative embodiments described herein, the inventor contemplates the use of the biochip devices in the detection, quantitation, or identification of a variety of organisms and macromolecules of biological or medical interest. For example, the chips may be used to detect or quantitate or identify pathogens of medical interest. Such pathogens may be viral (such as EBV, HIV, FIV, parvoviruses, retroviruses, and the like), rickettsial, fungal (including organisms such as Candida and other yeast genera, dermatomycotic fungi (including Epidermophyton spp., Microsporum spp., and Trichophyton spp., and the like), systemic fungi (including Blastomyces, Histoplasma, Coccidioides, Cryptococcus, Geotrichum, Histoplasma, Sporotrichum, and the like); bacterial (such as Mycobacteria including *Mycobacterium tuberculosis,* Vibrio including *V. cholerae;* Salmonella, including *S. choleraesius, S. paratyphi, S. schottmulleri,* and *S. typhimurium;* Treponema, including *T. pallidum;* Shigella, including *S. dysenteriae* and *S. flexneri,* Serratia, including *S. marcescens;* Yersinia, including *Y pestis* and *Y. pseudotuberculosis;* Proteus, including *P. mirabilis,* Morganella, including *M. morganii;* Streptococcus, including *S. faecalis, S. pneumoniae, S. salivarius, S. pyogenes,* and *S. sanguis,* Staphylococcus, including *S. aureus;* Bacillus including *B. anthracis, B. coagulans, B. pasteurii, B. cereus* and *B. subtilis,* or other disease-causing bacteria including those of the genera Leptospira, Clostridium, Neisseria, Brucella, Francisella, Hemophilus, Corynebacterium, and the like); or eukaryotic microorganisms such as Giardia, including *G. lamblia* and *G. intestinalis;* Chlamydia, including *C. psittaci* and *C. trachomatis,* and the like.

Alternatively, the detection of particular genes, such as the p53 cancer gene (Vo-Dinh et al., 1998a; 1998b), could also be performed using a single biochip or a plurality of individual biochips.

Another area of application of biochip technology is in functional genomics analysis. Provided that a reasonable degree of base complementarity exists, two nucleic acid strands from different sources (DNA and RNA) will undergo molecular hybridization under the proper conditions. This feature allows the biochip technology to be used also in the analysis of gene expression and function. Furthermore, the biochip can be also used to monitor the extent of genetic variation between individuals and their susceptibility to diseases.

The DNA biochip system offers a unique combination of performance capabilities and analytical features of merit not available in any other DNA analysis system currently available. With its multi-channel capability, the DNA biochip technology described herein is the first system described to date based on an optical sensing microchip system having an integrated signal amplifier and data treatment on-board. The DNA biochip device allows simultaneous detection of multiple DNA targets simultaneously. The advanced biochip system offers several advantages in size, performance, fabrication, analysis and production cost due to its integrated optical sensing microchip. The small sizes of the probes (microliter to nanoliter) minimize sample requirement and reduce reagent and waste requirement. Highly integrated systems lead to a reduction in noise and an increase in signal due to the improved efficiency of sample collection and the reduction of interfaces. The capability of large-scale production using low-cost IC technology is an important advantage. The assembly process of various components is simplified by integration of several elements on a single chip.

Example 2

Biochips Employing a Phototransistor IC

An important area in biological monitoring is the sensitive diagnosis of diseases, biological species or living systems (bacteria, virus or related components) at ultratrace levels in biological samples (e.g., tissues, blood and other bodily fluids) and environmental samples (e.g., air, soil and water samples). To detect a compound in a "real life" sample, a biosensor must be able to recognize and differentiate various biochemical constituents of these systems in order to provide unambiguous identification and accurate quantification Living systems possess exquisite recognition elements (e.g., antibody, enzyme, gene probes, etc.), often referred to as bioreceptors, which allow specific identification and detection of complex chemical and biological species This example describes a biosensor based on integrated circuit (IC) microchips using DNA bioreceptors designed to detect genetic constituents in complex samples of biomedical and environmental interest. In this system, phototransistors were used which are devices that can be miniaturized and fabricated on an integrated circuit. A phototransistor was developed that was composed of 220 phototransistor cells connected in parallel. This miniaturization technology is useful not only for the polynucleotide substrates and probes described here, but also for the integrated detector system that could be employed to produce microchip biosensor devices, i.e. "biosensor-on-a-chip". The device has sensors, amplifiers, discriminators and logic circuitry on board. These highly integrated biosensors were produced using the capability of fabricating multiple optical sensing elements and microelectronics on a single IC.

Biosensors combine two important concepts that integrate "biological recognition" and "sensing." The basic principle of an optical biosensor is to detect this molecular recognition and to transform it into an optical signal using a transducer.

The biochip device involves the combination of integrated circuit elements, electro-optics excitation/detection system, and DNA-based bioreceptor probes into a self-contained and integrated microdevice. A basic DNA biochip includes: 1) excitation light source with related optics, 2) a bioprobe, 3) a sampling element with sample platform and delivery system, 4) an optical detector with associated optics and dispersive device, and 5) a signal amplification/treatment system.

Construction of the advanced biochip involves integration of several basic elements of very different natures. The basic steps include: a) selection or development of the bioreceptor, b) selection of the excitation source, c) selection or development of the transducer, and d) integration of the excitation source-bioreceptor-transducer system.

The development of the DNA biochip in this example comprises three major elements. The first element involves the development of a bioreceptor probe system: a microarray of DNA probes on nitrocellulose sampling platform. The second element is focused on the development of non-radioactive methods for optical detection: the fluorescence technique. The third element involves the development of an integrated electro-optic IC system on a single chip for biosensing: phototransistor-amplifier microchip technology.

The design of the gene probe immobilization techniques on the biosensor substrates as well as the development of integrated electro-optic systems on IC biochips using a phototransistor multiarray system was demonstrated. Measurements of fluorescent-labeled DNA probes and hybridization studies with a HIV1 sequence-specific probe on the nitrocellulose sampling platform system illustrate the analytical figures of merit of this exemplary biochip device.

Experimental and Materials
Preparation of Oligonucleotides

Strands of oligonucleotides were synthesized and labeled with fluorescent labels (e.g., fluorescein and Cy5 dyes). Oligonucleotides were synthesized using an Expedite 8909 DNA synthesizer (Millipore, Bedford, Mass.). Fluorescein-labeled oligonucleotides were prepared with fluorescein CPG columns (for 3' labeling) or fluorescein phosphoramidite (for 5' labeling) using modified synthesis protocols as recommended by the manufacturers. Oligonucleotides with amino linkers were synthesized using either $C_3$ aminolink CPG for 3' labeling or 5' amino modifier $C_6$ (Glenn Research, Sterling, Va.) for 5' labeling. All oligonucleotides were synthesized using Expedite reagents (Millipore) and were de-protected and cleaved from the glass supports using ammonium hydroxide. The de-protected oligonucleotides were concentrated by evaporating the ammonium hydroxide in a Speedvac evaporator (Savant, Farmington, N.Y.) and re-suspended in 100 µL distilled $H_2O$. Further purification was performed by isopropanol precipitation of the DNA as follows: 10 µL of 3 M sodium acetate pH 7.0 and 110 µL isopropanol was added to 100 µL solution of DNA. The solution was then frozen at −70° C. Sodium acetate was used instead of amrnonium acetate since the residual ammonium ions interfere with Cy3 and Cy5 linkage as well as with binding of DNA to solid supports through the amino linkers. The precipitate was collected by centrifugation at room temperature for 15 min and was washed 3 times with 50% isopropanol. Residual isopropanol was removed by vacuum drying in the Speedvac and the DNA resuspended in sterile distilled water at a final concentration of 10 µg/µL. These stock solutions were diluted in the appropriate buffer at a 1:10 dilution to give a DNA concentration of 1 µg/µL.

For labeling DNA with Cy5 dye (Amersham Life Sciences, Arlington Heights, Ill.), modified oligonucleotides containing alkyl amino groups were derivatized as follows: 30 pmoles of the DNA was dissolved in 250 µL 0.5 M sodium chloride and passed through a Sephadex G10 (1 cm diameter, 10 cm long) (Pharmacia, Piscataway, N.J.) column equilibrated with 5 mM borate buffer (pH=8.0). The void volume containing the oligonucleotide was collected and concentrated by evaporation. This was dissolved in 100 µL 0.1 M carbonate buffer (pH=9.0). Cy5 (1 mg in carbonate buffer) was added to the oligonucleotide and the conjugation reaction was performed at room temperature for 60 min with occasional mixing. The conjugated oligonucleotide was separated from the free dye using a Sephadex G10 column as described above. The fractions containing the labeled DNA were collected and concentrated using a Speedvac evaporator.

Immobilization of DNA Probes and the Sampling Substrates

Biologically active DNA probes can be directly or indirectly immobilized onto a transducer detection surface to ensure optimal contact and maximum detection. When immobilized onto a substrate, the gene probes are stabilized and, therefore, can be reused repetitively. In one procedure, hybridization is performed on an immobilized target or a probe molecule attached on a solid surface such as nitrocellulose, or a nylon membrane, or a glass plate. Several methods can be employed to bind DNA to different supports. One method commonly used for binding DNA to glass involves silanization of the glass surface followed by activation with carbodiimide or glutaraldehyde.

Another approach consists of immobilizing the gene probe onto a membrane and subsequently attaching the membrane to the transducer detection surface. This approach has the advantage of avoiding a need to binding the bioreceptor onto the transducer. Several types of membranes are available for DNA binding: nitrocellulose, charge-modified nylon, etc. The gene probe was bound to the membrane using ultraviolet activation. With nitrocellulose membranes, the DNA solutions were spotted directly onto the membranes. The spots were subsequently subjected to either UV crosslinking using a Stratalinker (Stratagene, La Jolla, Calif.) or were baked in vacuum at 80° C. for two hours.

Hybridization on Nitrocellulose-based Sampling Platform

The first step in membrane hybridization involved immobilization of single-stranded DNA (ss-DNA) onto the selected surface of the sensor probe (e.g., membrane or surface). The probes were then treated with hybridization buffer to block nonspecific nucleic acid binding sites. Samples containing fluorescent-labeled DNA were delivered to the sensor probe and allowed to hybridize by reestablishing a double-stranded molecule with the complementary target sequences. After hybridization, excess unbound labeled DNA was washed off, and the hybrid target sequences detected. In this work, the nitrocellulose membranes were pre-hybridized for one hour at 37° C. in 5 mL of 6×SSC (1×SSC=15 mM Sodium citrate, 150 mM sodium chloride pH 7.0) containing 1% BSA and 0.2% SDS (sodium dodecyl sulfate). After pre-hybridization, the hybridization probe was added to a final concentration of 100 ng/ml and hybridizations performed for 16 h. After hybridization the membranes were washed in 5×SSC containing 0.1% SDS at room temperature for 10–15 min and at higher temperatures if necessary to reduce the background fluorescence levels.

Instrumentation System of the Microarray Probes

In addition to the integrated phototransistor IC device described in this example, an instrumental system was developed to evaluate the performance of the gene probes. A two-dimensional multiarray detection system using a charge-coupled device (CCD) was used with the initial system. The CCD experimental set-up consisted of a laser source, optical filters, lenses, the multiprobe waveguide and the CCD detector. For this evaluation, several lasers were used: a krypton ion laser (647.1 nm) was used for the Cy5 dye-labeled DNA probe, and an argon ion laser with the 514-nm line was used for a visible fluorescein-labeled DNA probe. The laser beam was focused into a 600 µm diameter fiber and transmitted to the sample substrate. The laser radiation was passed through a laser bandpass filter to remove unwanted laser lines or background fluorescence emission from the optical fiber. The fluorescence was passed through a Raman holographic filter to remove any remaining laser light, and was focused with a 1:2 50-mm lens and 2× macro focusing teleconverter onto the surface of a CCD detector. A 514.5-nm Raman holographic filter (Kaiser) was used to pass the fluorescence and block the laser light for fluorescence measurements. A 670-nm longpass filter was used to block laser excitation and pass the Cy5 fluorescence. Several CCD systems were evaluated including those from: Photometrics, Ltd. (e.g., Model PM-512) (Tucson, Ariz.), Princeton Instrument, (e.g., Model RE-ICCD) (Princeton, N.J.) and Santa Barbara Instruments Group (e.g., Model ST-6) (Santa Barbara, Calif.).

Results

Polynucleotides Microarrays

Extensive measurements were performed to evaluate the microarrays of DNA probes. A nitrocellulose membrane was used as the substrate for its ease in handling and its efficiency to bind DNA. Multiarrays of sample spots were produced, with liquid solutions of ssDNA sequences being dispensed onto the nitrocellulose (Zeta Probe®, Bio Rad, Hercules, Calif.) using a pV830 pneumatic Picopump™ (World Precision Instruments, Sarasota, Fla.). The Picopump™ was capable of producing regular microspots with diameter size range of 500–800 µm, which can be selected to match the size of detector elements. The DNA sample was loaded into a small diameter glass capillary, which was held a few mm above the cellulose membrane. The membrane was held in place on a vacuum flask fitted with a metal mesh frit. The vacuum procedure served two important purposes. First, the vacuum applied to the membrane improves the reproducibility of the spotting by maintaining the membrane flat against the metal mesh surface. The vacuum procedure also had a shortening effect on the sample drying process, which decreased the sample spot size by preventing the spread of sample though the membrane.

The Photometrics CCD (model CH 210) detection system was used to evaluate the DNA sample arrays since this system provides a 2-dimensional image of the probe array. The results showed the image obtained using the CCD system of fluorescein-labeled DNA samples designed as a 4×4 array onto the nitrocellulose membrane. The sample was illuminated with the 514.5-nm line of the argon laser. A Kaiser 514.5-nm holographic filter was used to block the laser excitation from the CCD. The results illustrated the efficiency of the Picopump™ spotting system developed to produce DNA arrays on the nitrocellulose sampling platform. The diameter of the sample spot can be regulated by varying the sampling volumes, and can be reproduced with 5–10% relative standard deviation. The amount of sample can be estimated by the intensity of the spot. For example, one spot on the array (location 1:3) indicated a higher amount of fluorescent materials than all the other sample spot arrays.

The process of gene probe sensing using both visible and NIR (700–1000 nm spectral range) fluorescent dye labels was also evaluated. Excitation and detection in the NIR range present certain difficulties but also offer several advantages. Measurements in the NIR are less interfered by background fluorescence of the nitrocellulose substrate since very few species with NIR emission occur. An important advantage associated with NIR measurements is the availability of low-cost, miniaturized diode lasers that usually have emission lines in the red and NIR regions. The DNA probes were labeled with the Cy5 NIR dye following the procedure described above. The diode laser line of 780 nm at 9.5 mW was used for excitation, and a calibration curve for the NIR dye-labeled single-stranded DNA over a concentration range from 1 pmol/µL to 3 fmnol/µL was generated. Excitation light was provided by a pen-size 9.5-mW laser diode (780 nm) and measurement times ranged from 1 to 3 min. This calibration curve was linear over the full range of the dye concentration investigated. The limit of optical detection, based on a signal equal to three times the standard deviation of the noise, was estimated to be in the 100 attomole/µL.

Hybridization studies were conducted to demonstrate the usefulness of the DNA array probes on the nitrocellulose sampling platform. The DNA probe's role is to identify the target compounds via molecular recognition. The operation of gene probes is based on the hybridization process. Hybridization involves the joining of a single strand of nucleic acid with a homologous complementary probe sequence. Hybridization of a nucleic acid probe to DNA biotargets (e.g., gene sequences, bacteria, viral DNA) offers a very high degree of accuracy for identifying DNA sequences complementary to that of the probe. Nucleic acids strands tend to be paired to their complements in the corresponding double-stranded structure. Therefore, a single-stranded DNA molecule will seek out its complement in a complex mixture of DNA containing large numbers of other nucleic acid molecules. Hence, nucleic acid probe (i.e. gene probe) detection methods are very specific to DNA sequences. cDNAs of specific sequences of the HIV1virus were bound onto the nitrocellulose membrane and hybridized them with Cy5-labeled DNA strands having complementary sequences. The HIV1 measurement on the nitrocellulose was performed by spotting the HIV1 probe DNA onto the nitrocellulose. The HIV1 gene probe is the 18-base oligonucleotide sequence complementary to the gag gene region (Clewley, 1989). Hybridization occurrence between complementary DNA sequences was demonstrated by positive detection of the fluorescence signals. The imaging system used the Photometrics CCD. The data showed the fluorescence signal obtained with the CCD detector resulting from the hybridization of HIV1 labeled gene probe with complementary DNA bound on the nitrocellulose membrane. The 3×3 array signal of the 3-dimensional plot demonstrated positive hybridization with the HIV1 probe. A reference system consisting of an array of control DNA probes, which do not have the sequence of the HIV1 gene, did not exhibit fluorescent signals. This result illustrates the capability of the nitrocellulose membrane as the sampling platform for in-situ hybridization studies on the DNA biochip.

Evaluation of the Phototransistor Integrated Circuit System

An important element in the biochip involves the design and development of an IC electro-optic system for the microchip detection elements using the phototransistor-amplifier technology. With this technology, highly integrated biosensors are made possible partly through the capability of fabricating multiple optical sensing elements and microelectronics on a single IC. A two-dimensional array of optical detector-amplifiers was integrated on a single IC chip. Each optical detector was a phototransistor coupled to a transimpedence amplifier followed by an amplifier. This block was repeated several times on the IC chip and combined with other electronic elements such as filters and amplifiers, which were also integrated on the same IC. The operational amplifier used with the phototransistor is a two-stage, unbuffered amplifier. The circuit is very compact, occupying an area of only 185 $\mu$m×200 $\mu$m. It was designed to be useful for wide-band amplification and low-level signals. The gain-bandwidth product is 70 MHz and the amplifier is stable for gains greater than 10. Other typical characteristics include: input offset voltage less than 5 mV, dc gain of 220, positive slew rate of 80 V/$\mu$s and negative slew rate of 9 V/$\mu$s. The circuit requires 2.5 mW from a single 5-V supply. This IC chip performed the complete conversion from an optical signal to an electrical signal suitable for data digitization and capture by a computer.

The circuit was fabricated in a 2-$\mu$m, p-well complementary metal oxide semiconductor (CMOS) process and occupied an area of 160,000 square microns. Detector elements using single phototransistors are not sufficiently sensitive for trace detection. Therefore, the phototransistor was actually composed of 220 phototransistor cells connected in parallel. An individual phototransistor cell occupied 760 square microns. The transimpedence amplifier had a gain of 100 kV/A. As the phototransistors were coupled with the 10-fold amplifier gain, the resulting gain was $10^6$ V/A. The phototransistors had a conversion gain on the order of 10 $\mu$A/$\mu$W, so the entire chain had an approximate conversion gain of 10 V/$\mu$W. The exact gain generally depends on the spectral region of interest and, to some extent, on the signal level being monitored.

The above-described elements may be modified to tailor the devices to specific applications. Since the phototransistor is made from basic photocell elements, it can be connected to as many cells as needed to create the desired geometry or required number of channels to adapt the detector to a specific application. Similarly, the gain and bandwidth of the amplifiers can be adjusted using simple resistor or capacitor changes, as the application requires.

The microchips designed and fabricated were evaluated by measuring the fluorescence signal of a fluorescein-labeled DNA sample spotted onto the membrane probe. The results illustrate the linearity of the microchip detector with respect to the fluorescein-labeled DNA concentrations and demonstrate the possibility for quantitative analysis.

Evaluation of the Biochip Using Flourescent-labeled DNA Probes

In this example the inventor developed and performed measurements using an amplifier-phototransistor (APT) device with 4×4 array of phototransistors. Whereas the CCD instrument was used to obtain an image of the microarray sample spots and to record a plot of the intensity, the signals from the APT microchip were directly recorded without the need of any electronic interface system or signal amplification device. The photocurrent of each sensing element of the APT microchip was transmitted directly into a digital photometer. The data from the photometer were linked to a personal computer (PC) via an RS-232 link. The samples consisted of an array of microspots of fluorescein-labeled DNA on a nitrocellulose membrane. In the study of the probe arrays on nitrocellulose membranes described in previous sections, the inventor used the CCD system to obtain a two-dimensional image of the fluorescence signals. Since the sensing elements of the phototransistor chip provide only signal intensity and not a signal profile, the inventor devised a device to record the response of the phototransistor detection elements as the sample spots were passed over the sensing elements. In this study, a nitrocellulose membrane having a series of fluorescein-labeled DNA sample spots was placed on a glass slide connected to a linear translation stage. The measurements were made while the translation stage moved the sample arrays over the stationary phototransistor device. Light from an argon ion laser at 488 nm was transmitted via an optical fiber and focused onto a sample spot. An appropriate optical filter placed between the sample substrate and the detector array was used to reject the laser radiation. The data showed four resolved signals as the sample spots moved over an APT microchip channel. Four sample spots of 1-$\mu$L of fluorescein-labeled DNA were placed on a nitrocellulose membrane, which was translated over a detection channel of an APT biochip. As the DNA spot passed over the photodetector, a fluorescence signal is detected.

Example 3

Multifunctional Biochips

Preparation of Oligonucleotides

The inventor synthesized desired strands of oligonucleotides and labeled them with fluorescent labels (e.g., fluorescein and Cy5 dyes) using procedures previously described (Vo-Dinh et al., 1987a; 1987b; Vo-Dinh et al., 1991). All oligonucleotides were synthesized using an Expedite 8909 DNA synthesizer (Millipore, Bedford, Mass.). Fluorescein-labeled oligonucleotides were prepared with fluorescein CPG columns (for 3' labeling) or fluorescein phosphoramidite (for 5' labeling) using modified synthesis protocols as recommended by the manufacturers. Oligonucleotides with amino linkers were synthesized using either C3 aminolink CPG for 3' labeling or 5' amino modifier C6 (Glenn Research, Sterling, Va.) for 5' labeling. All oligonucleotides were synthesized using Expedite reagents (Millipore) and were de-protected and cleaved from the glass supports using ammonium hydroxide. The de-protected oligonucleotides were concentrated by evaporating the ammonium hydroxide in a Speedvac evaporator (Savant Instruments, Farmingdale, N.Y.) and resuspended in 100 $\mu$L distilled $H_2O$. Further purification was performed by isopropanol precipitation of the DNA as follows: 10 $\mu$L of 3 M sodium acetate pH 7.0 and 110 $\mu$L isopropanol was added to 100 $\mu$L solution of DNA. The solution was then frozen at −70° C. Sodium acetate was used instead of ammonium acetate since the residual ammonium ions interfere with Cy5 linkage as well as with binding of DNA to solid supports through the amino linkers. The precipitate was collected by centrifugation at room temperature for 15 min and was washed 3 times with 50% isopropanol. Residual isopropanol was removed by vacuum drying in the Speedvac and the DNA resuspended in sterile distilled water at a final concentration of 10 $\mu$g/$\mu$L. These stock solutions were diluted in the appropriate buffer at a 1:10 dilution to give a DNA concentration of 1 $\mu$g/$\mu$L.

For labeling DNA with Cy5 dye (Amersham Life Sciences, Arlington Heights, Ill.), modified oligonucleotides containing alkyl amino groups were derivatized as follows (Vo-Dinh et al., 1987a; 1987b): 30 pmoles of the DNA was dissolved in 250 $\mu$L 0.5 M sodium chloride and passed through a Sephadex G10 (1 cm diameter, 10 cm long) (Pharmacia, San Diego, Calif.) column equilibrated with 5 mM borate buffer (pH=8.0). The void volume containing the oligonucleotide was collected and concentrated by evaporation. This was dissolved in 100 $\mu$L 0.1 M carbonate buffer (pH=9.0). Cy5 (1 mg in carbonate buffer) was added to the oligonucleotide and the conjugation reaction was performed at room temperature for 60 min with occasional mixing. The conjugated oligonucleotide was separated from the free dye using a Sephadex G10 column as described above. The fractions containing the labeled DNA were collected and concentrated using a Speedvac evaporator.

Immobilization of DNA Probes

Biologically active DNA probes can be directly or indirectly immobilized onto a transducer detection surface to ensure optimal contact and maximum detection. When immobilized onto a substrate, the gene probes are stabilized and, therefore, can be reused repetitively. In the simplest procedure, hybridization is performed on an immobilized target or a probe molecule attached on a solid surface such as a nitrocellulose, a nylon membrane or a glass plate.

Several methods can be used to bind DNA to different supports. The method commonly used for binding DNA to glass involves silanization of the glass surface followed by activation with carbodiimide or glutaraldehyde. The inventor has initially used the silanization methods for binding to glass surfaces using 3-glycidoxypropyltrimethoxysilane (GOP) or aminopropyltrimethoxysilane (APTS) and attempted to covalently link DNA via amino linkers incorporated either at the 3' or 5' end of the molecule during DNA synthesis.

Another approach consists of immobilizing the gene probe onto a membrane and subsequently attaching the membrane to the transducer detection surface. This approach avoids the need of binding the bioreceptor onto the transducer and could possibly allow easier large-scale production. Several types of membranes are available for DNA binding: nitrocellulose, charge-modified nylon, etc. The gene probe is then bound to the membrane using ultraviolet activation.

The first step in membrane hybridization is immobilization of single-stranded target nucleic acids to the selected surface of the probe (membrane, waveguide, optical fiber). The probes are then treated with hybridization buffer to block nonspecific nucleic acid binding sites. The probe is introduced to samples containing labeled DNA and allowed to hybridize by reestablishing a double-stranded molecule with the complementary target sequences. After hybridization, excess unbound labeled probe is washed off, and the hybrid target sequences detected.

Experimental Methods

Arrays of DNA probes are produce on the sampling platform by spotting the DNA on the Immunodine-ABC nitrocellulose membrane using a pV 830 pneumatic Picopump (World Precision Instruments, Sarasota, Fla.). The membrane is then blocked in 5 ml of the prehybridization solution for 1 h at 37° C. The prehybridization solution consists of: 6×SSC (1×SSC=15 mM Sodium citrate, 150 mM Sodium chloride, pH 7.0), 1% bovine serum albumin (BSA), and 0.2% sodium dodecyl sulfate (SDS). The Cy5-labeled hybridization probe is added to the final concentration of 100 ng/ml. The resulting sample is incubated at 37° C. for 16 h. The membrane is then washed in 5 ml of wash solution for 15 min at room temperature using the solution containing 5×SSC, 1% Carnation non fat dry milk, and 0.02% SDS. The membrane can be kept in H2O for extended periods before introducing onto the biochip sensing system for measurements. Fluorescence from labels of the hybridized DNA is performed by the biochip using an appropriate laser beam (diode laser or 632.8 nm-He Ne, Melles Griot).

Production of Antibody Arrays on the Sampling Platform

Monoclonal antibody to wild type p53 and human blocking peptide to p53 were obtained from Santa Cruz Biotechnologies. Control goat Immunoglobulin G (IgG), and rabbit antigoat IgG were obtained from Sigma Chemical Co (St. Louis, Mo.). Labeling of the goat/mouse IgG was performed using the following protocol. A solution of IgG (11.1 mg/mL) was dissolved in sodium bicarbonate buffer (pH=9.3, 0.1) and was incubated with solution of Cy-5 (Fluorolink Cy-5 Reactive Dye Pack, Biological Detection Systems, Inc., Pittsburgh, Pa., USA) for 30 min at room temperature. Following the dye conjugation step, the labeled IgG was separated from the dye using a Sephadex G-50 column and eluting the mixture with phosphate buffered saline. Fractions eluting in the void volume of the column were collected and pooled.

Immunodyne ABC Membrane (0.45 μm pore size) for antibody immobilization was obtained from Pall Corporation (East Hills, N.Y.). Phosphate buffered saline, pH 7.4, Triton X-100 and all other reagents were obtained from Sigma Chemical Co. (St. Louis, Mo.). Water was purified using a Milli-Q system from Millipore. Immunodyne ABC membranes, used as the material for the sampling platform, were placed on a Burleigh 6000 Controller micropositioner for potting. After 5 min air-drying, the membranes were blocked for 30 min with a 0.5% casein/PBS solution and afterwards they were incubated in a petri dish with 1 mL of the antigen solution (6 g/mL CY5-labelled sheep IgG and/or 10.4 g/mL CY5-labelled IgG) with continuous agitation in a shaker for 3 min. Finally the membranes were washed twice with 10 mL of a 0.1% triton X-100 (v/v) in PBS solution during 5 min and rinsed with 10 mL of PBS for 1 min in the shaker. The membranes were stored in PBS at 4° C. Alternatively, the membranes were directly spotted with 1 g/mL, 2 g/mL, 4 g/mL and 6 g/mL CY5-IgG, to evaluate the response of the biochip in the presence of different amounts of immobilized labeled antibody.

Measurements were performed to evaluate the effectiveness of the antibody and DNA probes' binding. For example, the membranes were first evaluated using the CCD image system in order to evaluate the extent of the antigen-antibody reaction and the degree of cross-reactivity between the different antibodies. The wet membranes were placed on glass plates in the imaging platform and fluorescence was collected.

Measurements Using the Multifunctional Biochip

Measurements were performed using the biochip device with a 4×4-photodiode array for simultaneous detection of the HIV1 gene and a gene from *Mycobacterium tuberculosis* (TB) using DNA probes, as well as the IgG protein and the cancer p53 antigen using antibody probes. The signals from the photodiode microchip were directly recorded without the need of any electronic interface system or signal amplification device. The photocurrent of each sensing of the microchip was transmitted directly into a digital photometer or a strip chart recorder. The data from the photometer were linked to a personal computer (PC) via an RS-232 link. The sampling platform of the biochip contained a 4×4 array of microspots of NIR-labeled DNA and antigens on a membrane sampling substrate.

The HIV1 gene probe is the 18-base oligonucleotide sequence complementary to the gag gene region (Isola et al., 1998). The inventor has used the TB4 sequence as the probe in previous study (Isola et al., 1996). For this study, the inventor bound cDNA of specific sequences of the HIV1 virus and the TB bacterium onto the membrane/sampling platform and hybridized them with Cy5 dye-labeled DNA strands having complementary sequences. The HIV1 measurements on the nitrocellulose was performed by spotting the HIV1 probe DNA in a 4×4 array onto the nitrocellulose sampling platform. The DNA was then crosslinked to the nitrocellulose using either a UV crosslinker or baked in vacuum at 80° C. for two hours.

Several procedures can be used to evaluate the biochip. With one procedure using nitrocellulose membrane platform, the DNA solutions were spotted directly onto the membranes. The spots were subsequently subjected to either UV crosslinking using a Stratalinker (Stratagene, La Jolla, Calif.) or were baked in vacuum at 80° C. for two hours. The first step in membrane hybridization involved immobilization of single-stranded target nucleic acids to the selected surface of the probe. The probes were then treated with hybridization buffer to block nonspecific nucleic acid binding sites. The probe was introduced to samples containing labeled probe DNA and allowed to hybridize by reestablishing a double-stranded molecule with the complementary target sequences. After hybridization, excess unbound labeled probe was washed off, and the hybrid target sequences detected. In this work, the nitrocellulose membranes were pre-hybridized for one hour at 37° C. in 5 mL of 6×SSC (1×SSC=15 mM Sodiun citrate, 150 mM sodium chloride pH 7.0) containing 1% BSA, 0.2% SDS (sodium dodecyl sulfate). After pre-hybridization, the hybridization probe was added to a final concentration of 100 ng/ml and hybridizations performed. After hybridization the membranes were washed in 5×SSC containing 0.1% SDS at room temperature for 10–15 min to reduce the background fluorescence levels.

Figure 4:
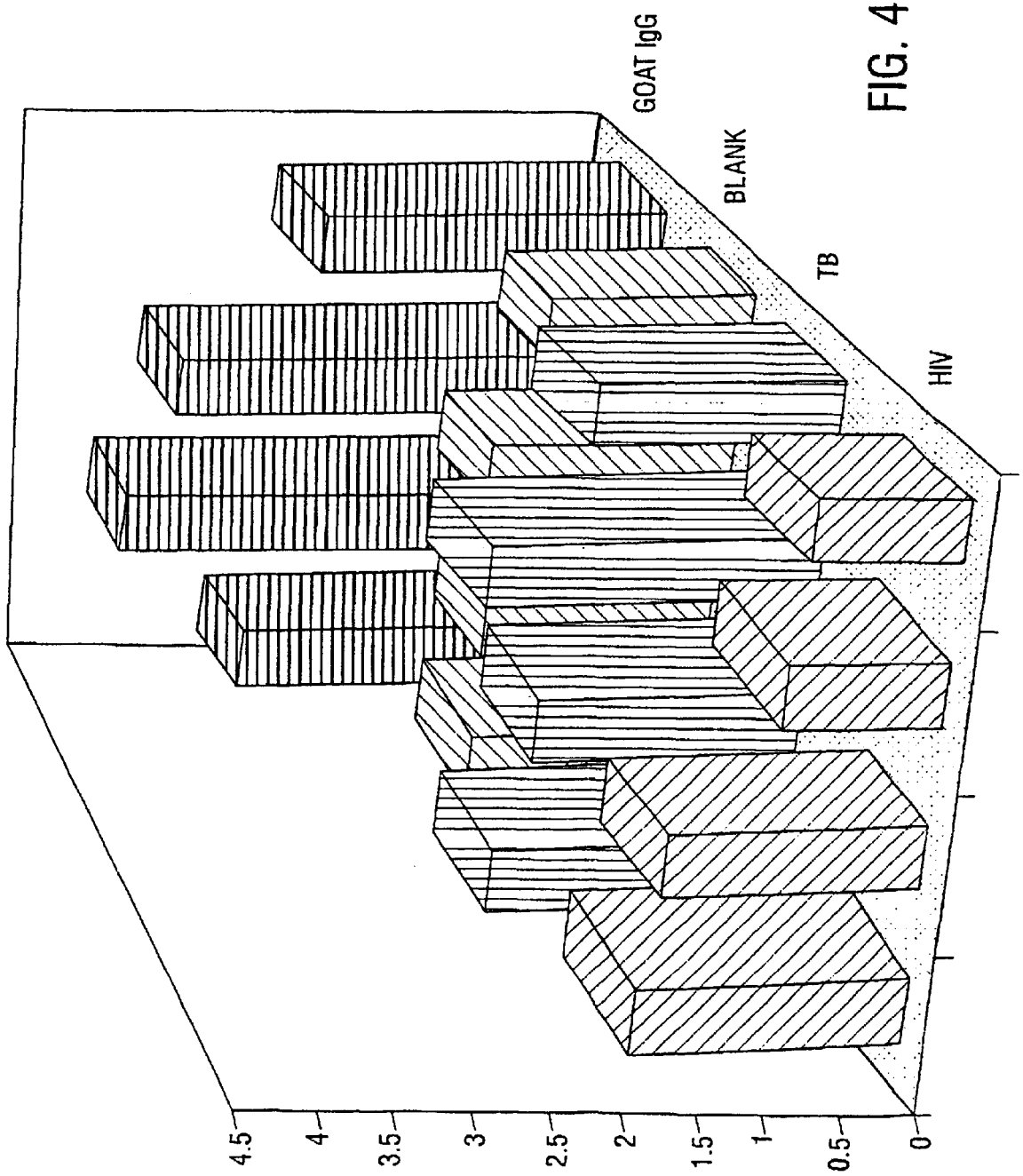
FIG. 4 illustrates the simultaneous detection of HIV, TB and Goat IgG protein using HIV DNA probe (4 channels corresponding to the first row of the biochip), TB DNA probe (second row), and antibody probe for Goat IgG (fourth row). The blank signals (which correspond to DNA that is not complementary to the probes, or antigens not targeted by the antibody probes) are shown in the third row for comparison.

Hybridization occurs between complementary DNA sequences and binding antibody-antigen was demonstrated by the fluorescence signals detected by the biochip. FIG. 4 shows that only fluorescence signals were detected on the biochip channels where hybridization of labeled DNA HIV1 (TB) gene probes with complementary bound-DNA fragments had occurred. This figure shows the simultaneous detection of HIV, TB and Goat IgG protein using HIV DNA probe (4 channels corresponding to the first row of the biochip), TB DNA probe (second row), and antibody probe for Goat IgG (fourth row). The blank signals (which correspond to DNA that is not complementary to the probes, or antigens not targeted by the antibody probes) are shown in the third row for comparison. The results demonstrate the use of the multifunctional biochip to detect more than one type of macromolecule on a single chip device.

Example 4

Capture Probe Techniques Using the AMB System

Figure 5:
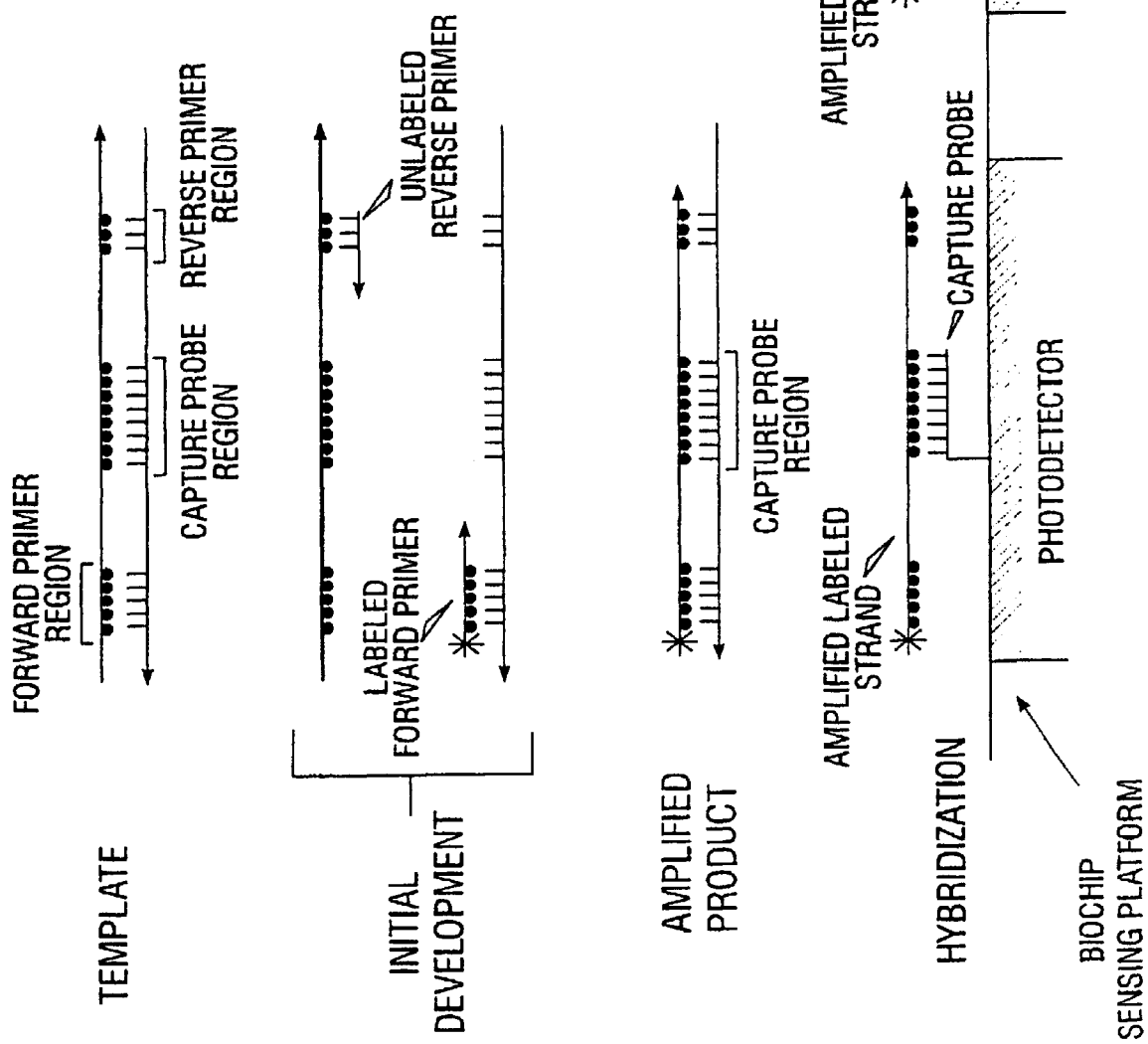
FIG. 5 illustrates one possible use of the AMB device utilizing a capture probe configuration.

In an illustrative embodiment (shown schematically in FIG. 5), capture probes are bound onto the sampling platform of the biochip in arrays matching the photodetectors. The probes can be bound directly onto the detectors surface or onto a substrate placed over the detectors. The forward primer is labeled with a fluorescent dye and used as primer for PCR™ amplification of the DNA target sequence. The bound capture target is hybridized with the total PCR™ product. The two primers have no complementarity with the bound capture probe sequence. Only the target sequence hybridizes with the capture probe sequence. Positive hybridization produces the fluorescence signal of the labels.

This method involves using a fluorescence-labeled DNA sequence as a primer in PCR™ amplification of the target DNA followed by hybridization to a capture probe sequence. Crystal Fast Violet (CFV) dye can be used as a fluorescence label. This dye can be excited using 510nm excitation light to emit a broad fluorescence from 600 nm to 680 nm. The capture probe, which is complementary to an internal sequence of the amplified product, is bound to the sampling platform of the biochip. Such a platform can be made of glass, silica, or plastic material such as polystyrene. Small wells can be etched onto the sampling platform to match the locations of the sensing arrays. After hybridization of the capture probe with the CFV-labeled sequence, the polystyrene wells are subjected to stringency washes to remove nonspecific binding of the sequences. The fluorescence signals from the CFV label are finally detected. This method takes advantage of the PCR method to amplify the target DNA as well as the use of the amplified target DNA with a fluorescent label. Schematic representations of the target DNA template and the capture probe method of detection are presented in FIG. 8.

Preparation of Buffers and Reagents

All buffers and reagents were molecular biology grade (DNAse and RNAse free) and were sterilized by autoclaving. Only sterilized plastic ware (microcentrifuge tubes, pipette tips etc.,) were used for all procedures.

Synthesis of Oligonucleotides

All the oligonucleotides used in this study were synthesized using an Expedite 8909 nucleic acid synthesizer (Millipore). Expedite reagents were used providing faster synthesis, and de-protection times. The controlled pore glass (CPG) containing the synthetic oligonucleotides was immersed in 1 mL of 30% ammonium hydroxide (Sigma Chemical Co., St. Louis, Mo., USA). This mixture was incubated at room temperature for 2 h. to cleave the nucleic acids from the glass support. The mixture was further incubated at 55° C. for 30 min to remove the dimethyltrityl protective groups on the nucleotides. Ammonium hydroxide was removed by vacuum evaporation and the oligonucleotides were re-suspended in sterile distilled water at a concentration of 10 $\mu g/\mu L$.

Labelling of Primers

Crystal fast violet-labeled oligonucleotide primers were prepared using the following procedure. Approximately 10 micrograms of the oligonucleotides was dried down by vacuum evaporation in a microcentrifuge tube. Then 50 $\mu L$ of 0.2 M imidazole (1,3-diaza-2,4-cyclopentadiene) at pH 8.0, and 50 $\mu L$ of 50 mM 1-ethyl-3-(dimethylamino)propyl carbodiimide (EDC) in 2-(N-morpholino)ethanesulfonic acid (MES) buffer (pH 8.0) were added and incubated at 50° C. for 3 h. This treatment resulted in the production of 5'-phosphorimidazolides. One hundred microliters of a saturated solution of CFV in sterile distilled water was added and incubated for 18 hours at 50° C. The un-reacted CFV was removed by gel filtration using a Sephadex G10 (Pharmacia) column equilibrated with 0.1 M borate buffer (pH 8.0). The void volume containing the CFV labeled DNA was collected and concentrated by vacuum evaporation. This product was re-suspended in distilled water and sodium acetate was added to a final concentration of 0.3 M. An equal volume of isopropanol was added to precipitate the DNA. Complete precipitation was achieved by freezing the mixture at −80° C. The precipitate was then collected by centrifugation at room temperature in a microfuge for 10 min at 10,000×g. The product was finally washed in 50% isopropanol several times to remove any traces of unbound CFV.

Polymerase Chain Reaction (PCR) Procedure

Polymerase chain reaction amplification of target template DNA was performed in 50 $\mu L$ aliquots using a Coy thermal cycler as follows: the amplification reactions were performed in 100 mM Tris-HCl (pH 8.3), containing 50 mM KCl, 1.5 mM $MgCl_2$, 0.01% gelatin with 10 ng of purified template DNA, 20 $\mu M$ of each of the two primers, and 3 $\mu M$ of each of the four deoxynucleoside triphosphates [deoxyadenine triphosphate (dATP), deoxycytosine triphosphate (dCTP), deoxyguanine triphosphate (dGTP) and deoxythymine triphosphate (dTTP)]. Amplifications were performed with an initial heating step of 95° C. for 5 min to denature the template. The ensuing cycling process included denaturation for 30 sec at 94° C., annealing for 30 sec at 50° C., and extension for 30 sec. at 72° C. A total of thirty cycles was performed. Ten microliters of the reaction was electrophoresed on 1.5% agarose gel in Tris-borate buffer (44.5 mM Tris, 4.5 mM borate, pH 8.3). The gels were stained with ethidium bromide (0.5 μg/mL) and DNA bands were photographed with a UV trans-illuminator (310 nm) using standard methods. PCR was also performed with a CFV-labeled forward primer. After PCR with CFV-labeled primer, 15 μL of the amplification mixture was removed for electrophoretic detection of the product and 15 μL 20×SSC (0.3 M sodium citrate, pH 7.0, containing 3.0 M sodium chloride) was added. This process resulted in bringing the amplified target DNA to a final concentration of 5×SSC, suitable for hybridization. This solution was heated to boiling to dissociate double-stranded DNA and was used directly for the hybridization.

Binding of the Capture Probe to Solid Surface of the Biochip

Capture probe sequences were synthesized with a 6-carbon 5'-amino linker, which was necessary for anchoring the capture probe to the solid support of the biochip's sampling platform. They were purified as described above and re-suspended in 0.1-M carbonate buffer (pH 9.0) at a final concentration of 1 g/L. The purified capture probe solution was spotted onto N-oxysuccinimide (NOS)-derivatized polystyrene plates (DNA-BIND from Corning-Costar) and incubated at 37° C. for one hour. Unbound DNA was removed by washing several times in phosphate buffered saline.

Hybridization

The unreacted sites on the DNA-BIND plate were blocked by adding 200 μL of 3% BSA (bovine serum albumin) in 0.1-M carbonate buffer (pH 9.0) and incubating at 37° C. for 30 min. The double-stranded PCR™ amplifier probe sequence was denatured by boiling in water for 5 min and rapidly chilling on ice to prevent DNA strand reassociation. The resulting PCR reaction mixture was directly used as the probe. One hundred microliters of the denatured probe DNA at a concentration of 100 ng/mL in hybridization solution (5×SSC containing 1.0% Carnation non-fat dry milk, 0.02% sodium dodecyl sulfate) was added to each well and hybridizations were performed at 5° C. below the $T_m$ for one hour. The $T_m$ (melting temperature) value of the capture probe sequence under the salt conditions used was 42° C.

Example 5

DNA Beacon Techniques Using the Biosensor

A recent method based on molecular beacons has to provide a rapid, quantitative measurement for the biochip. Molecular beacons, first reported by Tyagi and Kramer (1996), consist of oligonucleotide probes that are complementary to a target nucleic acid (e.g., rRNA) and that incorporate a fluorescent molecule and a quenching molecule. They are designed to report the presence of the target sequence with fluorescence. They exploit the principle of fluorescence resonance energy transfer (FRET) between the fluorescent molecule and the quenching molecule to generate a fluorescent signal when target nucleic acids as hybridized in solutions. The fluorescence remains quenched in the absence of a complementary sequence.

Figure 6A:
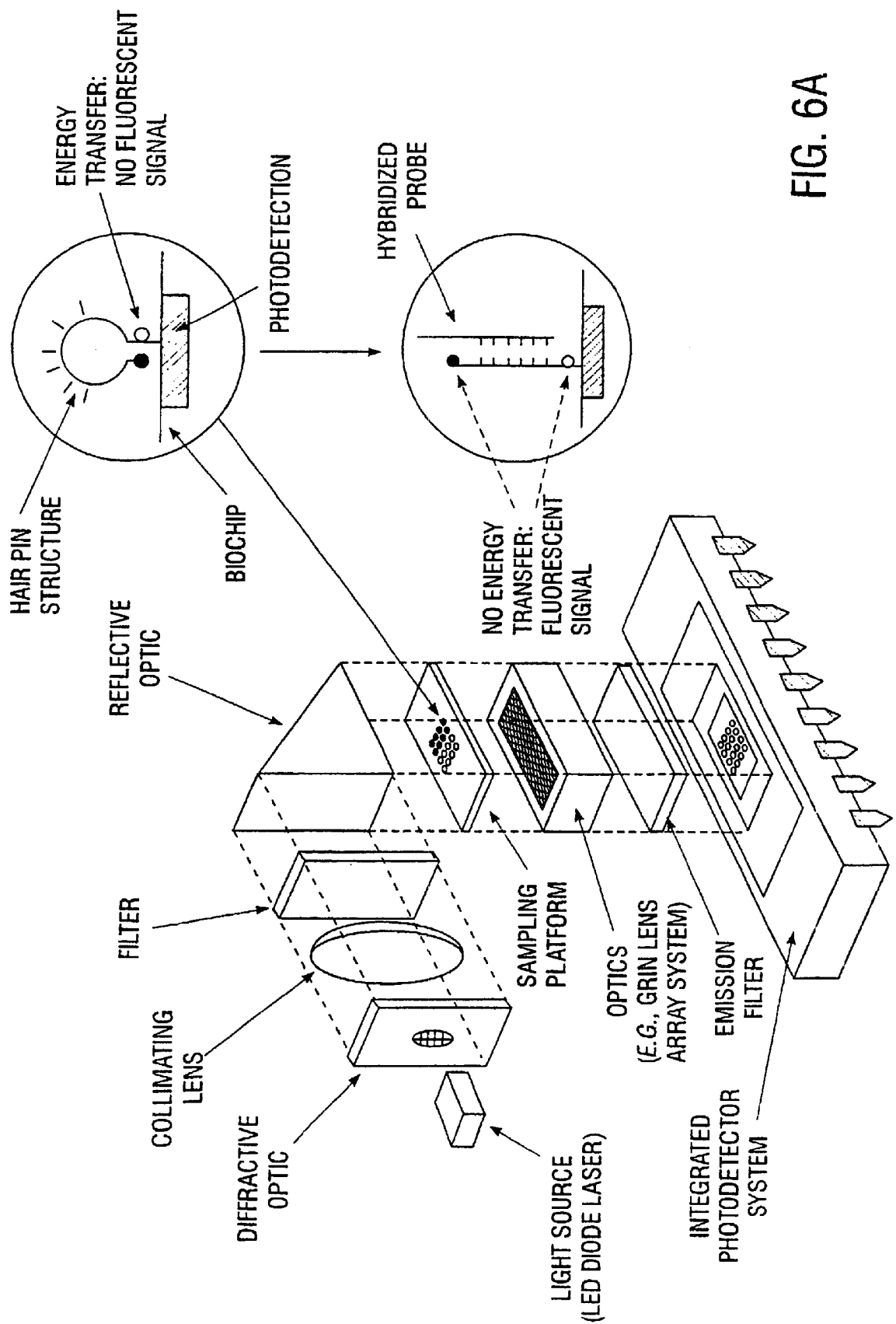
FIG. 6A illustrates one embodiment of the AMB device utilizing a molecular beacon detection system.
Figure 6B:
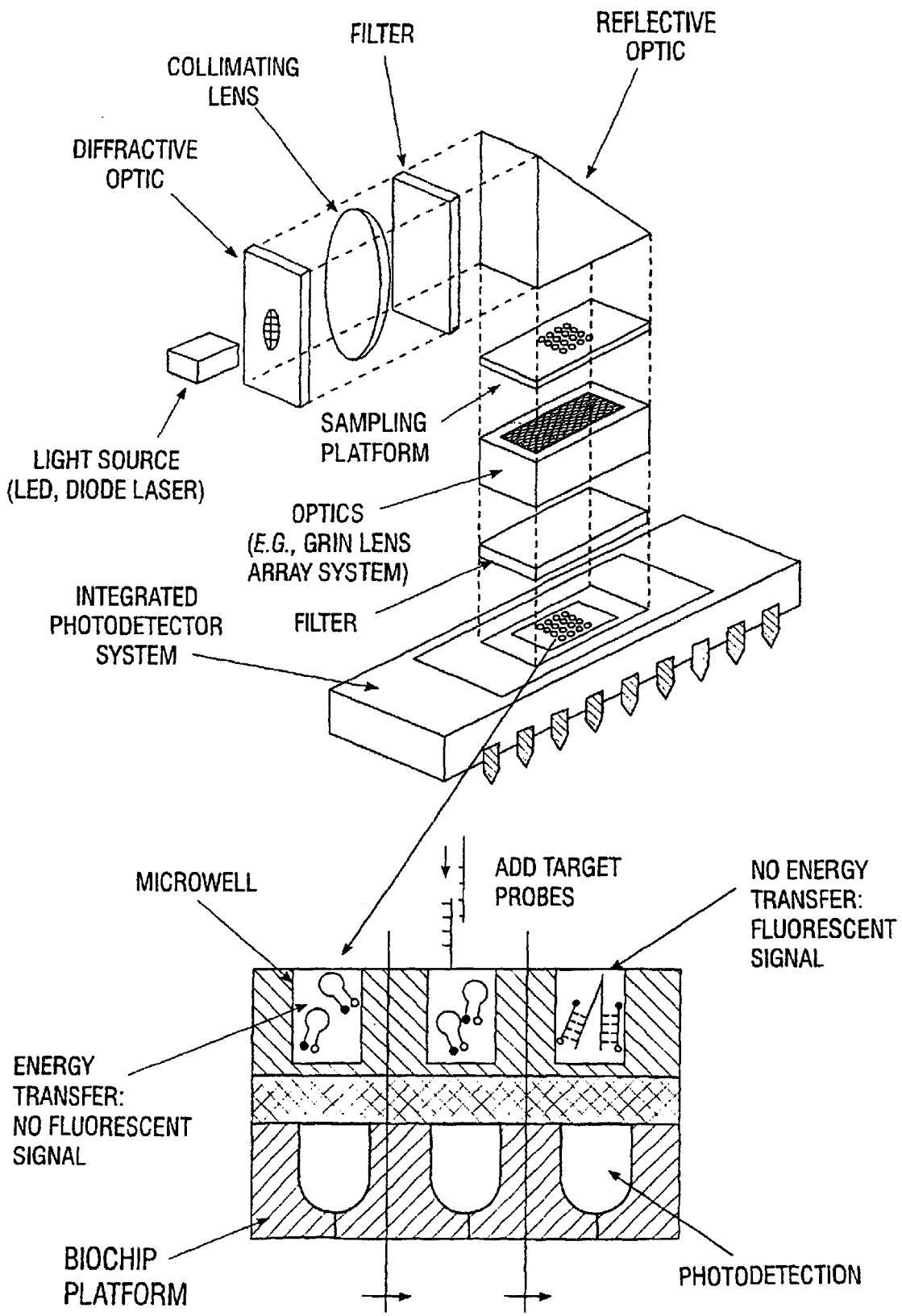
FIG. 6B illustrates another embodiment of the AMB device utilizing homogeneous association of molecular beacons.

Molecular DNA beacons consist of stem loop structures (hairpin). FIG. 6A and FIG. 6B illustrate their operation principle. A molecular beacon hybridizes to its target region via the complementary sequence contained in the loop of the probe, thereby physically separating the fluorescent molecule attached to the 5'-end from the quenching molecule attached to the 3'-end. Alternatively, molecular beacons create an intermolecular stem structure ensuring the quenching of the fluorescent signal by close juxtaposition of both the 5'-(bound to fluorescent molecule) and the 3'-end (bound to quencher).

Molecular beacons can be used for the detection of nucleic acids in solution obtained directly from environmental samples by simple extraction protocols or after amplification by the PCR™. It may also be possible to detect nucleic acids in intact cells. Recently, Schofield et al. (1997) redesigned three existing rRNA targeted oligonucleotide probes to be used as molecular beacons to quantify microbial populations in the rumen. Molecular beacons are synthesized with a sulfhydryl group covalently linked to the 5' phosphate via a $(CH_2)_6$ spacer and with a primary amino acid group linked to the 3' hydroxyl via a $(CH_2)_7$ spacer. This synthesis step is followed by two consecutive coupling reactions to covalently link a quencher to the 3'-amino group and a fluorophor to the 5' sulfhydryl groups. Probe synthesis may be performed by technique using cDNAs.

For example, the human immnunodeficiency virus (HIV) gag gene sequence can be used as a model. Infection with the human immunodeficiency virus Type 1 (HIV1) results in a uniformly fatal disease. Unfortunately standard HIV serologic tests, including the enzyme-linked immunosorbent assay and the Western blot assay, are not useful in the diagnosis of HIV infection during early infancy because of the confounding presence of trans-placentally derived maternal antibody in the infants blood. There is a need for a direct nucleic acid based test that detects the presence of HIV viral sequences. For example, a molecular beacon probe targeted to the HIV1 can be designed as follows. The middle potion of probe region has 20-base oligonucleotide sequence complementary to the gag gene region of the HIV1: e.g., ATAGTGGATCTTGAAATTTA (SEQ ID NO:1). This middle region has two 6-nucleotide-long arm sequences, each from each side: e.g., CGATTCA and GCTAAGT. A fluorophor molecule is attached to the end of one arm, and the corresponding quencher at the other end. Several fluorophor-quencher systems may be used: EDANS [5-(2'aminoethyl)aminonaphthalene-1-sulfonic acid] and DABCYL [4-(4'-dimethylaminophenylazo)benzoic acid]. Under normal conditions (when the target DNA) is not present), the two arm regions are hybridized to each other since they have complementary sequences, thus forming a stemmed loop which bring the fluorophor-quencher molecules in close proximity. Therefore, even under excitation, the fluorophor molecules' fluorescence is quenched and no fluorescence signal is detected. When the target sequences (containing a sequence of the gag region of the HIV1, 5'-TATCACCTAGAACTTTAAAT-3'; SEQ ID NO:2) are introduced in to the sampling areas, then hybridization occurs between the target and probe sequences, inducing a conformation change that separates the arm sequences and move the quencher molecule from the fluorophor. This process will produce an increase in fluorescence signal from the fluorophor molecules. Instead of using a fluorophor-quencher system (anthracene and perylene), on can use an energy-transfer spectral shift (ETSS) system. Such a system consists of two fluorophor molecules (donor and acceptor molecules).

Two sampling platforms embodiments are possible for the molecular beacon techniques. In one embodiment the probes are bound to the sampling platform of the biochip (FIG. 6A). In the other embodiment, the probes are free in solution contained in the micro-cavity of the biochip, thus allowing homogenous assays (FIG. 6B).

Example 6

Combination with DNA Amplification Systems

Figure 7:
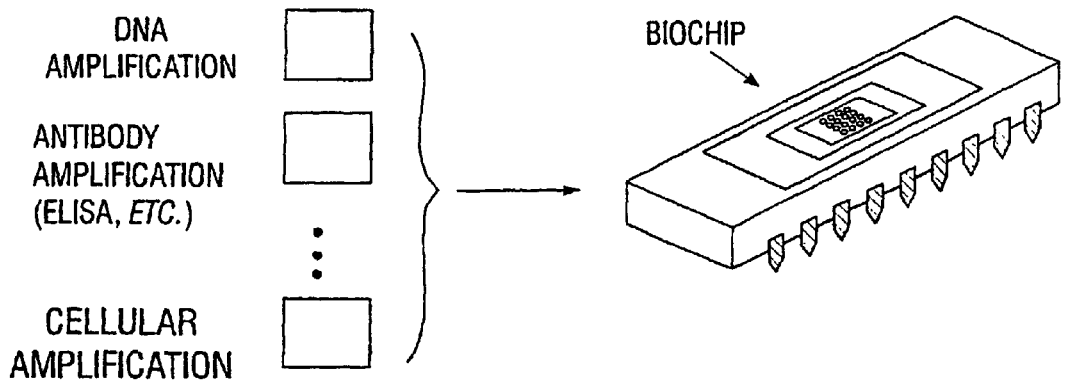
FIG. 7 illustrates an embodiment of the present invention that utilizes combination nucleic acid amplification and detection on a single chip.

Polymerase chain reaction (PCR™) is used to detect and amplify low levels of target sequence from a mixture of nucleic acids. With a theoretical detection limit of a single target molecule, PCR™ is often the method of choice- when detecting extremely low levels of nucleic acids. The main disadvantage of PCR™ lies in the variability of the amplification process. Despite creative adaptations of PCR™ for quantitative detection of nucleic acids, the method remains at best semi-quantitative in all but optimal conditions. Thus, despite the significant advantage provided by an extreme detection limit, current PCR™ technology precludes its use in the determination of microbial abundance (FIG. 7).

Example 7

High-throughput Screening AMB System

Figure 8:
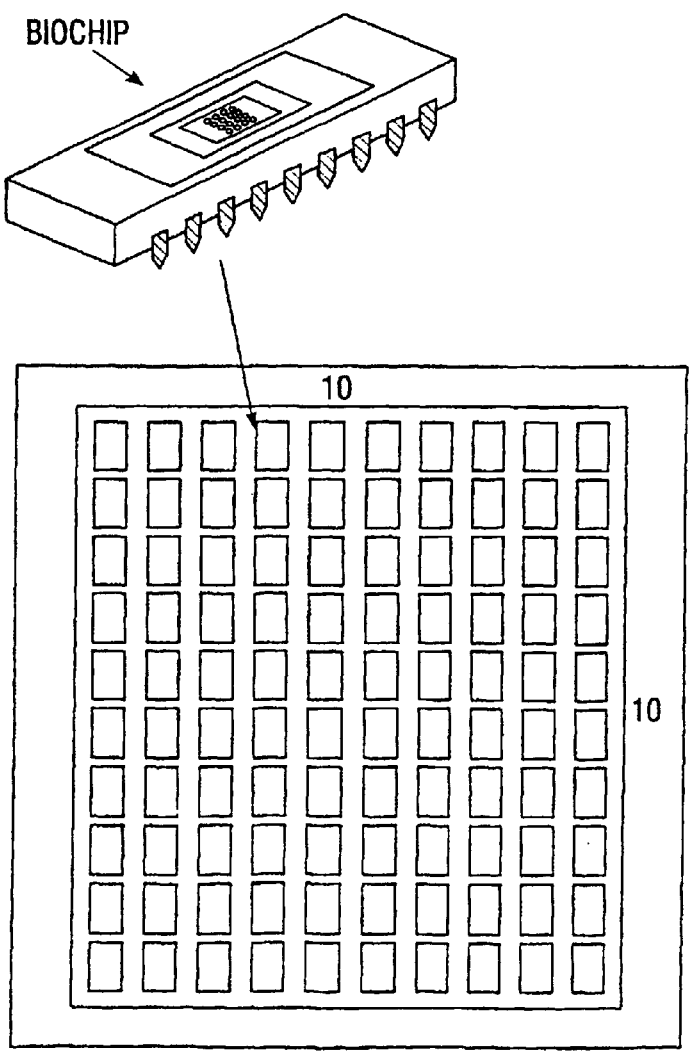
FIG. 8 illustrates schematically the integration of multiple AMB devices for high throughput screening of large numbers of samples. Shown is a 10×10 array of biochips that can provide 10,000 ($10^4$) sensing channels.

Integration of multiple biochips (for example 10×10 will provide 10,000 ($10^4$) sensing channels for high throughput screening (FIG. 8). With its multi-channel capability, the AMB technology is the only current system that allows simultaneous detection of multiple medical targets (up to 100 channels) simultaneously using antibody, DNA, as well as other bioreceptors (proteins, cells, biomimetic systems).

This is the first development of an integrated IC system having multifunctional bioprobes in a single device. The AMB system offers a unique combination of performance capabilities and analytical features of merit not available in any other blood analysis system currently available. The present biochip also offers several advantages in size, performance, fabrication, analysis and production cost. The small sizes of the probes (microliter to nanoliter) minimize sample amount requirement and reduce reagent and waste requirement. Highly integrated systems lead to a reduction in noise and an increase in signal due to the improved efficiency of sample collection and the reduction of interfaces. The capability of large-scale production using low-cost IC technology is an important advantage. The assembly process of various components is made simple by integration of several elements on a single chip. For medical applications or drug screening, this cost advantage will allows the preparation of extremely low cost, disposable biochips that can be used for rapid high-throughput screening, environmental monitoring, or in-home medical diagnostics of diseases without the need of sending samples to a laboratory for analysis.

Example 8

Other Types of Bioreceptors

In addition to the use of antibody and DNA probes, other types of bioreceptors can be used in the AMB system. These include: enzymes, proteins, cells or cell components, biomimetic probes such as: "molecular imprint" antibodies, DNA-based adaptamers, peptides nucleic acids (PNA); cyclodextrins; non-protein protein-like molecules, dendrimers, etc.

A variety of proteins may be used as bioreceptors. For instance, layers of protein films in which avidin or streptavidin is used as a linking agent, are widely used for diagnostics (Edmiston and Saavedra, 1998).

Example 9

Molecular Imprint Technology and the AMB

Molecular imprint technology is a rapidly emerging field in which synthetic polymers, produced in the presence of a guest molecule, or "print molecule", will provide the specific binding sites after the print molecule is removed (Wulff et al., 1973; Mosbach, 1994). The print molecule is generally the analyte of interest or a closely-related analog. The molecular imprint polymers (MIP) provide specific binding sites since the polymerization process results in the formation of a rigid binding pocket in which only the analyte of interest can fit. The MIPS are often known as "plastic antibodies" since many of the properties that control binding may be similar for both receptor systems.

The various steps involved in the development of the polymer imprint method are as follows: First, the print molecule is mixed with the functional monomers used to make the conducting polymers. Print molecule can be a chemical, a biological species (proteins, bacteria, virus, etc.). Functional monomers are polymerizable chemical units that possess specific chemical functionalities. The monomer may bind to the print molecule non-covalently or covalently. The particular functional monomer (or combination of monomers) used to produce the conducting polymer depends on the desired electric conduction properties and on the chemical properties of the analyte. For instance, it is important to use a functional monomer that forms strong bonds (e.g., hydrogen bond or electrostatic bonds) with the analyte molecule.

After selection of the monomer, association and binding of the monomer(s) to the print molecule is performed. The "print/mold system" is polymerized using excess co-monomer, or cross-linking agent. After polymerization, the print molecule is chemically cleaved (e.g., hydrolyzed), or extracted from the polymer, thus leaving an imprint" of the print molecule on the conducting polymer. The removal method depends on the nature of binding of the print molecules to the polymer. The imprint is the covalently attached onto the biochip's sampling platform (similar as with an actual antibody). The measurements with the biochip are performed using similar procedures as with antibodies described above.

The oligonucleotide primers are designed to hybridize to regions of DNA that flank a specific target gene sequence. The primers are then extended across the target sequence by using thermostable *Thermus aquaticus* (Taq) polymerase in the presence of free deoxynucleoside triphosphates. Completion of this extension process leads to duplication of the initial target gene sequence. This process can be repeated many times and leads to an exponential increase in the target gene sequence of interest. The biochip technology developed in this work can take advantage of the PCR™ power derived both from the specificity of the reaction and its high gain amplification. Direct detection of appropriately labeled nucleic acid probes, i.e. without PCR™, can be performed rapidly without the delay times involved in the heating and annealing cycles. With PCR™, which requires several minutes, the sensitivity of the assay can be increased drastically. For instance, repetition of the melting, annealing and extension process over 20 cycles leads to a million-fold increase in the copy number of the original DNA. The biochip can be further developed to include an integrated platform for PCR™ or with other amplification techniques.

REFERENCES

The following references, to the extent that they provide exemplary procedural or other details supplementary to those set forth herein, are specifically incorporated herein by reference.

U.S. patent application Ser. No. 08/979,672, filed Nov. 26, 1997.
U.S. patent application Ser. No. 09/236,758, filed Jan. 25, 1999.
U.S. Pat. No. 4,196,265, issued Apr. 1, 1980.
U.S. Pat. No. 4,237,224, issued Dec. 2, 1980.
U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,883,750, issued Nov. 28, 1989.
U.S. Pat. No. 4,965,188, issued Oct. 23, 1990.
U.S. Pat. No. 4,987,071, issued Jan. 22, 1991.
U.S. Pat. No. 5,176,995, issued Jan. 5, 1993.
U.S. Pat. No. 5,631,359, issued May 20, 1997.
U.S. Pat. No. 5,700,922, issued Dec. 23, 1997.
Eur. Pat. Appl. Publ. No. 320308.
Eur. Pat. Appl. Publ. No.329822.
Eur. Pat. Appl. Publ. No. 360257.
Intl. Pat. Appl. Publ. No. PCT/US87/00880.
Intl. Pat. Appl. Publ. No. PCT/US89/01025.
Intl. Pat. Appl. Publ. No. PCT/US98/25294.
Intl. Pat. Appl. Publ. No. WO 88/10315.
Intl. Pat. Appl. Publ. No. WO 89/06700.
Affyetrix web site: http://www.affymetrix.com; Jul. 23, 1997.
Ahluwalia, De Rossi, Ristori, Schirone, Serra, "A comparative study of protein immobilization techniques for optical immunosensors," *Biosensors and Bioelectronics*, 7:207–214, 1991.
Alarie et al, "Intensified charge coupled device-based fiberoptic monitor for rapid remote surface-enhanced Raman scattering sensing," *Appl. Spectrosc.*, 46:1608–1612, 1992.
Alvarez-Icaza and Bilitewski, "Mass production of biosensors," *Anal. Chem.*, 65:525A–533A, 1993.
Anis, Wright, Rogers, Thompson, Valdes, Eldefrawi, "A fiber-optic immunosensor for detecting parathion," *Anal. Lett.*, 25:627–635, 1992.
Armitage et al., "Peptide nucleic acid-DNA duplexes: long range hole migration from an internally linked anthraquinone," *Proc. Natl. Acad. Sci. USA*, 94(23) :12320–12325, 1997.
Aubert, Oguey, Vuillcumier, "Monolithic Optical Position Encoder with On-Chip Photodiodes," *IEEE J. Solid State Circuits*, 23(2):465–73, 1988.
Barnard and Walt, "Optical immunosensors using controlled-release polymers," In: *Biosensors and Chemical Sensors, Optimizing Performance Through Polymeric Materials*, Edelman and Wang, Eds., American Chemical Society Symposium Series, 487, ACS, Washington, pp 310–320, 1992.
Bhatia, Shriver-Lake, Prior, Georger, Calvert, Bredehorst, Ligler, "Use of thio-terminal silanes and heterobifunctional crosslinkers for immobilization of antibodies on silica surfaces," *Anal. Biochem.*, 178:408–413, 1989.
Blackburn, Talley, Booth, Durfor, Martin, Napper, Rees, "Potentiometric biosensor employing catalytic antibodies as the molecular recognition element," *Anal. Chem.*, 62:2211–2216, 1990.
Blanchard, Taylor, Busey, Williamson, "Regeneration of immunosorbent surfaces used in clinical, industrial and environmental biosensors. Role of covalent and non-covalent interactions," *J. Immunol. Method*, 130:263–275, 1990.
Boffa, Carpaneto, Allfrey, "Isolation of active genes containing CAG repeats by DNA strand invasion by a peptide nucleic acid," *Proc. Natl. Acad Sci. USA*, 92(6) :1901–1905, 1995.
Bulte et al., "Dysprosium-DOTA-PAMAM dendrimers as macromolecular T2 contast agents. Preparation and relaxometry," *Invest. Radiol.*, 33(11):841–845, 1998.
Carlsson et al., "Screening for genetic mutations," *Nature*, 380(6571):207, 1996.
Christensen et al., "Solid-phase synthesis of peptide nucleic acids," *J. Pept. Sci.*, 1(3):175–183, 1995.
Clewley, "The polymerase chain reaction, a review of the practical limitations for human immunodeficiency virus diagnosis," *J. Virol. Methods*, 25(2):179–187,1989.
Collins and Olive, "Reaction conditions and kinetics of self-cleavage of a ribozyme derived from Neurospora VS RNA," *Biochem.*, 32(11):2795–2799, 1993.
Corey, "Peptide nucleic acids: expanding the scope of nucleic acid recognition," *Trends Biotechnol.*, 15(6) :224–229, 1997.
Darnell, Lodish. Baltimore. In: *Molecular Cell Biology*, 2nd Ed. Scientific American Books, New York, 1990.
Downs, "Prospects for Nucleic-Acid biosensors," *Biochem. Soc. Trans.*, 19:39–43, 1991.
Dueholm et al., *J. Org. Chem.*, 59:5767–5773, 1994.
Edmiston and Saavedra,*J. Am. Chem. Soc.*, 120:1665–1671, 1998.
Eggers et al., "A microchip for quantitative detection of molecules utilizing luminescent and radioisotope reporter groups," *Biotechniques*, 17:516–523, 1994.
Egholm et al., "PNA hybridizes to complementary oligonucleotides obeying the Watson-Crick hydrogen-bonding rules, *Nature*, 365(6446):566–568, 1993.
Erdeniz et al, "Cloning-free PCR-based allele replacement methods," *Genome Res.*, 7(12):1174–1183, 1997.
Fodor, Read, Pirrung, Stryer, Lu, Solas, "Light directed, spatially addressable parallel chemical synthesis," *Science*, 251:767–769, 1991.
Footer, Engholm, Kron, Coull, Matsudaira, "Biochemical evidence that a D-loop is part of a four-stranded PNA-DNA bundle. Nickel-mediated cleavage of duplex DNA by a Gly-Gly-His bis-PNA," *Biochemistry*, 35(33) :10673–10679, 1996.
Frohman, M. A., In: *PCR Protocols: A Guide to Methods and Applications*, Academic Press, New York, 1990.
Gambacorti-Passerini et al., "In vitro transcription and translation inhibition by anti-promyelocytic leukemia (PML)/ retinoic acid receptor alpha and anti-PML peptide nucleic acid," *Blood*, 88(4):1411–1417, 1996.
Geiger, Allen, Strader, In: *VLSI Design Techniques for Analog and Digital Circuits*, McGraw-Hill Publishing Co., New York, 1990.
Goding, In: *Monoclonal Antibodies: Principles and Practice*, 2nd Edition, Academic Press, Orlando, Fla., pp. 60–74, 1986.
Good and Nielsen, "Progress in developing PNA as a gene-targeted drug," *Antisense Nucleic Acid Drug Dev.*, 7(4):431–437, 1997.
Graham et al., "Gene probe assay on a fibre-optic evanescent wave biosensor," *Biosensors and Bioelectronics*, 7:487–493, 1992.

Griffith et al., *J. Am. Chem. Soc.*, 117:831–832, 1995.

Guerrier-Takada et al., "The RNA moiety of ribonuclease P is the catalytic subunit of the enzyme," *Cell,* 35(3 Pt 2):849, 1983.

Haaima, Lohse, Buchardt, Nielsen, *Angew. Chem., Int. Ed. Engl.,* 35:1939–1942, 1996.

Hampel and Tritz, "RNA catalytic properties of the minimum (–)sTRSV sequence," *Biochem.,* 28(12):4929, 1989.

Hampel et al., "'Hairpin' catalytic RNA model: evidence for helices and sequence requirement for substrate RNA," *Nucl. Acids Res.,* 18(2):299, 1990.

Hanvey et al., "Antisense and antigene properties of peptide nucleic acids," *Science,* 258(5087):1481–1485, 1992.

Harlow and Lane, *In: Antibodies: A Laboratory Manual,* Cold Spring Harbor Laboratory, Cold Spring Harbor, N.Y., 1988.

Haynes, Stura, Hilvert, Wilson, "Routes to catalysis: structure of a catalytic antibody and comparison with its natural counterpart," *Science,* 263:646–652, 1994.

Hill, Urwin, Crampton, "A comparison of non-radioactive labeling and detection systems with synthetic oligonucleotide probes for the species identification of mosquitoes in the Anopheles gambiae complex," *Am. J. Trop. Med Hyg.,* 44(6):609–622, 1991.

Hyrup and Nielsen, "Peptide nucleic acids (PNA): synthesis, properties and potential applications," *Bioorg. Med. Chem.,* 4(1):5–23, 1996.

Isola et al., "Development of a genosensor for *Mycobacterium tuberculosis,*" *In: Biomedical Sensing, Imaging and Tracking Technologies,* Liebermann et al. Eds., SPIE Publishers, Bellingham, Wash., 2676:228–240, 1996.

Isola et al., "Surface-enhanced Raman gene probe for HIV detection," *Anal. Chem.,* 70:1352–1356, 1998.

Kaiser and Kezdy, "Amphiphilic secondary structure design of peptide hormones," *Science,* 223(4633):249–255, 1984.

Koch et al., *Tetrahedron Lett.,* 36:6933–6936, 1995.

Kremsky et al., *Tetrahedron Lett.,* 37:4313–4316, 1996.

Kuby, *Immunology 2nd Edition,* W. H. Freeman and Company, N.Y., 1994.

Kumar et al., "Monitoring oligonucleotide hybridization using light-addressable potentiometric and evanescent wave fluorescence sensing," *Materials Science and Engineering,* C1:187–192, 1994.

Kung, Panfili, Sheldon, King, Nagainis, Gomez, Ross, Briggs, Zuk, "Picogram quantitation of total DNA using DNA-binding proteins in a silicon sensor-based system," *Anal. Biochem.,* 187:220–227, 1990.

Kunkel et al., "Rapid and efficient site-specific mutagenesis without phenotypic selection," *Methods Enzymol.,* 154:367–382, 1987.

Kwoh et al, "Transcription-based amplification system and detection of amplified human immunodeficiency virus type 1 with a bead-based sandwich hybridization format," *Proc. Natl. Acad. Sci. USA,* 86(4):1 173–1177, 1989.

Landsdorp et al., "Heterogeneity in telomere length of human chromosomes," *Hum. Mol. Genet.,* 5(5):685–691, 1996.

Lee and Thompson, "Fibre optic biosensor assay of Newcastle Disease Virus," *Defense Research Establishment Suffield, Canada, Suffield Report* No. 580, pp. 1–36, 1993.

Lerner, Benkovic, Schultz, "At the crossroads of chemistry and immunology: catalytic antibodies," *Science,* 252:659–667, 1991.

Lowe, "Biosensors," *Phil. Trans. R. Soc. Lond,* B324:487–496, 1989.

Maloy, *In: Experimental Techniques in Bacterial Genetics,* Jones and Bartlett Publishers, Boston, Mass., 1990.

McGall et al., "Light-directed synthesis of high-density oligonucleotide arrays using semiconductor photoresists," *Proc. Natl. Acad. Sci. USA,* 93(24):13555–13560, 1997.

Michael, "Mutagenesis by incorporation of a phosphorylated oligo during PCR amplification," *Biotechniques,* 16(3):410–412, 1994.

Mosbach, "Molecular imprinting", *Trends Biochem. Sci.,* 19(1):9–14, 1994.

Mrksich and Whitesides, "Patterning self-assembled monolayers using microcontact printing: a new technology for biosensors," *Trends Biotechnol.,* 13:228–235, 1995.

Nanogen web site: http://www.nanogen.com.

Neilsen, *In: Perspectives in Drug Discovery and Design* 4, Escom Science Publishers, pp. 76–84, 1996.

Nielsen, Egholm, Berg, and Buchardt, "Sequence-selective recognition of DNA by strand displacement with a thymine-substituted polyamide," *Science,* 254, 1497–1500, 1991.

North, "Immunosensors: antibody based biosensors," *Trends Biotechnol.,* 3:180–186, 1985.

Norton, Waggenspack, Varnum, Corey, "Targeting peptide nucleic acid-protein conjugates to structural features within duplex DNA," *Bioorg. Med. Chem.,* 3(4):437–445, 1995.

Ogert, Brown, Singh, Shriver-Lake, Ligler, "Detection of *Clostridium botulinum* toxin A using a fibre optic based biosensor," *Anal. Biochem.,* 205:306–312, 1992.

Ohara et al., "One-sided polymerase chain reaction: the amplification of cDNA," *Proc. Natl. Acad. Sci. USA,* 86(15):5673–5677, 1989.

Orum, Nielsen, Jorgensen, Larsson, Stanley, Koch, "Sequence-specific purification of nucleic acids by PNA-controlled hybrid selection," *BioTechniques,* 19(3):472–480, 1995.

Pardridge, Boado, Kang, "Vector-mediated delivery of a polyamide ("peptide") nucleic acid analogue through the blood-brain barrier in vivo," *Proc. Natl. Acad. Sci. USA,* 92(12):5592–5596, 1995.

Perrotta and Been, "Cleavage of oligoribonucleotides by a ribozyme derived from the hepatitis delta virus RNA sequence," *Biochem.,* 31(1):16–21, 1992.

Perry-O'Keefe, Yao, Coull, Fuchs, Egholm, Peptide nucleic acid pre-gel hybridization: an alternative to southern hybridization," *Proc. Natl. Acad Sci. USA,* 93:14670–14675, 1996.

Petersen, Jensen, Egholm, Nielsen, Buchardt, *Bioorg. Med Chem. Lett.,* 5:1119–1124, 1995.

Piunno, Krull, Hudson, Damha, Cohen, "Fiber optic biosensor for fluorimetric detection of DNA hybridization," *Anal. Chim. Acta,* 288:205–214, 1994.

Prokop and Bajpai, "Recombinant DNA Technology I," Conference on Progress in Recombinant DNA Technology Applications, Potosi, MI, Jun. 3–8, 1990, *Ann. N. Y Acad Sci.,* 646:1–383, 1991.

Qin et al., "Efficient transfer of genes into murine cardiac grafts by Starburst polyamidoamine dendrimers," *Hum. Gene Ther.,* 9(4):553–560, 1998.

Rechnitz and Ho, "Biosensors based on cell and tissue material," *J. Biotechnol.,* 15:201–218, 1990.

Roe, "Biosensor development," *Pharm. Res.,* 9:835–844, 1992.

Rook, "Immunity to viruses, bacteria and fungi," *In: Immunology,* I. Roitt, J. Brostoff and D. Male (Eds.), Gower Medical Publishing, London, pp. 16.1–16.15, 1989.

Rossi et al., *AIDS Res. Hum. Retrovir.,* 8:183, 1992.

Rusckowski et al., "Pretargeting using peptide nucleic acid," *Cancer,* 80(12 Suppl.):2699–2705, 1997.

Sadik, John, Wallace, Barnett, Clarke, Laing, "Pulsed amperometric detection of thaumatin using antibody-containing poly(pyrrole) electrodes," *Analyst,* 119:1997–2000, 1994.

Saiki et al., "Prime-directed enzymatic amplification of DNA with a themostatable DNA polymerase," *Science,* 239:487–491, 1988.

Saiki, Scharf, Faloona, Mullis, Horn, Erlich, Annheim, "Enzymatic amplification of β-globin genomic sequences and restriction site analysis for diagnosis of sickle cell anemia," *Science,* 230:1350–1354, 1985.

Sakthivel et al., "Synthesis and physicochemical properties of lipophilic polyamide dendrimers," *Pharm. Res.,* 15(5):776–782, 1998.

Sambrook et al., *In: Molecular Cloning: A Laboratory Manual,* Cold Spring Harbor Laboratory Press, Second Edition, Cold Spring Harbor, N.Y., 1989.

Saville and Collins, "A site-specific self-cleavage reaction performed by a novel RNA in Neurospora mitochondria," *Cell,* 61:685–696, 1990.

Saville and Collins, "RNA-mediated ligation of self-cleavage products of a Neurospora mitochondrial plasmid transcript," *Proc. Natl. Acad Sci. USA,* 88(19):8826–8830, 1991.

Sayler and Layton, "Environmental application of nucleic-acid hybridization," *Annu. Rev. Microbiol.,* 44:625–648, 1990.

Scheller, Schubert, Pfeiffer, Hintsche, Dransfeld, Renneberg, Wollenberger, Riedel, Pavlova, Kuhn, Müller, Tan, Hoffmann, Moritz, "Research and development of biosensors," *Analyst (Lond.),* 114:653–662, 1989.

Schena et al., "Quantitative monitoring of gene expression patterns with a complementary DNA microarray," *Science,* 270:467–470, 1995.

Schofield et al., *Appl. Env. Microb.,* 63:1143, 1997.

Seeger et al., "PNA-mediated purification of PCR amplifiable human genomic DNA from whole blood," *Biotechniques,* 23(3):512–517, 1997.

Segal, *In: Biochemical Calculations,* 2nd Edition, John Wiley and Sons, New York, 1976.

Shoemaker, Lashkari, Deval, Morris, Mittman, and Davis, "Quantitative phenotypic analysis of yeast deletion mutants using a highly parallel molecular bar-coding strategy," *Nat Genet.,* 14(4):450–456, 1996.

Smith, Dawson, Gannon, "The 16S/23S ribosomal RNA spacer region as a target for DNA probes to identify potential biological warfare threats," *In: Proc. 1993 ERDEC Scientific Conference on Chemical Defense Research,* November 16–19, D. A. Berg, J. D. Williams Jr. and P. J. Reeves (eds.) Report No. ERDEC-SP-024, August, pp. 603–608, 1994.

Steffan and Atlas, "Polymerase chain reaction: applications in environmental microbiology," *Ann. Rev. Microbiol.,* 45:137–161, 1991.

Stetsenko, Lubyako, Potapov, Azhikina, Sverdlov, *Tetrahedron Lett.,* 37:3571–3574, 1996.

Stevenson et al., "Synchronous luminescence: a new detection technique for multiple probes used for DNA sequencing," *Biotechniques,* 16:1104–1110, 1994.

Thiede, Bayerdorffer, Blasczyk, Wittig, Neubauer, "Simple and sensitive detection of mutations in the ras proto-oncogenes using PNA-mediated PCR clamping," *Nucleic Acids Res.,* 24(5):983–984, 1996.

Thomson et al., *Tetrahedron,* 51:6179–6194, 1995.

Tomic et al., "A rapid and simple method for introducing specific mutations into any position of DNA leaving all other positions unaltered," *Nucl. Acids Res.,* 18(6):1656, 1990.

Topchieva et al., "Novel derivatives of cyclodextrins, modified with poly(ethylene oxide) and their complexation properties," *Bioconjug. Chem.,* 9(6):676–682, 1998.

Tromberg et al., "Fiber-optic chemical sensors for competitive binding fluoroimmunoassay," *Anal. Chem.,* 59(8):1226–30, 1987.

Turner, "Molecules which recognize antigen," *In: Immunology,* Roitt, Brostoff and Male, (Eds.), Gower Medical Publishing, London, pp. 5.1–5.11, 1989.

Tyagi and Kramer, "Molecular beacons: probes that fluoresce upon hybridization," *Nat. Biotechnol.,* 14(3):303–308, 1996.

Ulmann, Will, Breipohi, Langner, Ryte, *Angew. Chem., Int. Ed. Engl.,* 35:2632–2635, 1996.

Upender et al., "Megaprimer method for in vitro mutagenesis using parallel templates," *Biotechniques,* 18(1):29–30; 32, 1995.

Van Emon and Lopez-Avila, "Immunochemical methods for environmental analysis," *Anal. Chem.,* 64:79A–88A, 1992.

Vo-Dinh et al., "Development of a Biochip for Gene Detection," *Proceedings of SPIE Conference on Biomedical Sensing and Tracking Technologies,* San Jose, Calif., Jan. 26–29, 1998a.

Vo-Dinh et al., "Development of a multiarray biosensor for DNA diagnostics," *Instrumentation Science & Technology,* in press, 1998b.

Vo-Dinh et al., "Fiber optic Fluoroimmunosensors," in *Fiber Optic Chemical Sensors and Biosensors,* Wolfbeis (Ed.), CRC Press, Boca Raton, Fla., 1991.

Vo-Dinh et al., "Surface-enhanced Raman gene probes," *Anal. Chem.,* 66:3379–3383, 1994.

Vo-Dinh et al., *Appl. Spectr.,* 41:605.1 987a.

Vo-Dinh et al., "Antibody-based fiberoptics biosensor for the carcinogen benzo[a]pyrene," *Appl. Spectrosc.,* 5:735–738, 1987b.

Vogelstein and Kinzler, "p53 function and dysfunction," *Cell,* 70:523–526, 1992.

Walker et al., "Isothermal in vitro amplification of DNA by a restriction enzyme/DNA polymerase system," *Proc. Natl. Acad Sci. USA,* 89(1):392–396, 1992.

Wang, Stacy, Binder, Marin-Padilla, Sharpe, Speck, "Disruption of the Cbfa2 gene causes necrosis and hemorrhaging in the central nervous system and blocks definitive hematopoiesis," *Proc. Natl. Acad Sci. USA,* 93:3444–3449, 1996a.

Wang, Stacy, Miller, Lewis, Gu, Huang, Bushweller, Bories, Alt, Ryan, Liu, Wynshaw-Boris, Binder, Marin-Padilla, Sharpe, Speck, "The Cbfβ subunit is essential for CBFα2 (AML1) function in vivo," *Cell,* 87:697–708, 1996b.

Watson, J. D. et al., *Molecular Biology of the Gene,* 4th Ed., W. A. Benjamin, Inc., Menlo Park, Calif., 1987.

Webb and Hurskainen, *J. Biomol. Screen,* 1:119–121, 1996.

Wijesuriya, Anderson, Ligler, "A rapid and sensitive immunoassay for bacterial cells," *In. Proc. 1993 ERDEC Scientific Conference on Chemical Defense Research,* November 16–19, Berg, Williams and Reeves, (Eds.), Report No. ERDEC-SP-024, August, pp. 671–677, 1994.

Wilbur et al., "Biotin reagents for antibody pretargeting. 3. Synthesis, radioiodination and evaluation of biotinylated starburst dendrimers," *Bioconjug. Chem.,* 9(6):813–825, 1998.

Wingard, "Biosensor trends," *Ann. N. Y. Acad Sci.,* 613:44–53, 1990.

Wolinsky et al., "Adaptive evolution of human immnodeficiency virus-type 1 during the natural course of infection," *Science,* 272(5261):537–542, 1996.

Woolf et al., "Specificity of antisense oligonucleotides in vivo," *Proc. Natl. Acad Sci. USA,* 89(16):7305–7309, 1992.

Wu, and Dean, "Functional significance of loops in the receptor binding domain of Bacillus thuringiensis CryIIIA δ-endotoxin," *J. Mol. Biol.,* 255:628–640, 1996.

Wulff, G. et al., *Tetrhedron Lett.,* 44:4329, 1973.

Zull, Reed-Mundell, Lee, Vezenov, Ziats, Anderson, Sukenik, "Problems and approaches in covalent attachment of peptides and proteins to organic surfaces for biosensor applications," *J. Indust. Microbiol.,* 13:137–143, 1994.

All of the methods and apparatus disclosed and claimed herein can be made and executed without undue experimentation in light of the present disclosure. While the compositions and methods of this invention have been described in terms of preferred embodiments, it will be apparent to those of skill in the art that variations may be applied to the methods, apparatus, and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An integrated biosensor system for the simultaneous detection of a plurality of different types of targets, said system comprising:
    at least one sampling platform, said sampling platform including a plurality of receptors for binding to said targets, said plurality of receptors including at least one protein receptor and at least one nucleic acid receptor;
    at least one excitation source of electromagnetic radiation at a first frequency for irradiating said receptors, wherein electromagnetic radiation at a second frequency different from said first frequency is emitted in response to said irradiating when at least one of said plurality of different types of targets are bound to said plurality of receptor probes, and
    an integrated circuit detector system having a plurality of detection channels for detecting electromagnetic radiation at said second frequency, said detection channels each including at least one detector.

2. The integrated biosensor system of claim 1, wherein said sampling platform comprises a solid support.

3. The integrated biosensor system of claim 1, wherein said plurality of targets include at least one selected from the group consisting of a bacterium, a fungus, a virus, and an eukaryotic microorganism.

4. The integrated biosensor system claim 1, wherein said plurality of targets include at least one selected from the group consisting of polynucleotides, polypeptides and peptides.

5. The integrated biosensor system claim 2, wherein said solid support comprises at least one selected from the group consisting of a substrate, a filter, and a membrane.

6. The integrated biosensor system of claim 2, wherein said solid support prevents transmission of certain wavelengths of said electromagnetic signals.

7. The integrated biosensor system of claim 2, wherein said solid support further comprises an optical filter or a lens.

8. The integrated biosensor system of claim 1, wherein each said plurality of receptors include at least one selected from the group consisting of a biomimetic, a cell receptor and an intact biological cell.

9. The integrated biosensor system of claim 8, wherein said plurality of receptors include at least one selected from the group consisting of a chemical receptor, a bioreceptor and a biopolymer.

10. The integrated biosensor system of claim 8, wherein said plurality of receptors include at least one biomimetic material, said biomimetic material comprising at least one selected from the group consisting of a molecular imprint material and a cyclodextrin probe.

11. The integrated biosensor system of claim 1, wherein said at least one excitation source of electromagnetic radiation comprises at least one selected from the group consisting of a light emitting diode, a diode array, a laser and a laser array.

12. The integrated biosensor system of claim 11, wherein said excitation source is disposed on-chip.

13. The integrated biosensor system of claim 11, wherein said excitation source is disposed off-chip.

14. The integrated biosensor system of claim 1, wherein said detection channels include a photodetector.

15. The integrated biosensor system of claim 14, wherein said photodetector is at least one selected from the group consisting of a photodiode, an avalanche photodiode and a phototransistor.

16. The integrated biosensor system of claim 1, further comprising an on-chip signal amplification system or an on-chip signal processing system.

17. The integrated biosensor system of claim 16, wherein said on-chip signal amplification system or said on-chip signal processing system further comprises a microprocessor or an amplifier.

18. The integrated biosensor system of claim 1, wherein said detection channels further comprise a transimpedence amplifier or a low-pass filter.

19. The integrated biosensor system of claim 1, wherein said plurality of receptors are tagged with a label that responds to incident electromagnetic radiation by emitting or absorbing distinct electromagnetic responses, each response having a different frequency.

20. The integrated biosensor system of claim 19, wherein said electromagnetic responses are at least one selected from the group consisting of luminescence scattering, infrared absorption and ultraviolet absorption.

21. The integrated biosensor system of claim 1, wherein said plurality of receptors respond to electromagnetic irradiation by radiating a luminous signal.

22. The integrated biosensor system of claim 21, wherein said luminous signal is in the visible or near-infrared region of the electromagnetic spectrum.

23. The integrated biosensor system of claim 4, wherein said polynucleotides comprises at least one selected from the group consisting of DNA, PNA and RNA.

24. The integrated biosensor system of claim 1, wherein the detection channels further comprises an amplifier.

25. The integrated biosensor system of claim 1, wherein said detection channels include optical detectors and amplifier, said optical detectors and amplifiers being integrated on a single circuit.

26. The integrated biosensor system of claim 1, wherein the plurality of detection channels comprises an array of n-well amplifier photodiodes.

27. A method for the simultaneous detection of a plurality of different types of targets in a sample, said method comprising the steps of:

contacting said integrated biosensor system of claim 1 with said sample, wherein binding events occur at respective ones of said plurality of receptors when at least one of said plurality of different types of targets are present in said sample;

irradiating at least a portion of said plurality of receptors with light or other electromagnetic radiation at a first frequency, wherein electromagnetic radiation at a second frequency different from said first frequency is emitted in response to said irradiating when at least one of said plurality of different types of targets are bound to said plurality of receptor probes, measuring said electromagnetic radiation at a second frequency, and, detecting simultaneously the presence or absence of said plurality of different types of targets in said sample.

28. A method for detecting a plurality of different pathogens in a sample, comprising the steps of:

contacting said integrated biosensor system of claim 1 with said sample, wherein one or more of said plurality of receptors is specific for each of said pathogens, wherein binding events occur at respective ones of said plurality of receptors when at least one of said plurality of different pathogens are present in said sample;

irradiating at least a portion of said plurality of receptors, wherein electromagnetic radiation at a second frequency different from said first frequency is emitted in response to said irradiating when at least one of said pathogens are bound to said plurality of receptor probes;

measuring said electromagnetic radiation at a second frequency, and, detecting the presence or absence of said plurality of pathogens in said sample.

\* \* \* \* \*